United States Patent
Mahajan et al.

(10) Patent No.: US 7,312,066 B2
(45) Date of Patent: Dec. 25, 2007

(54) NUCLEIC ACID MOLECULES ENCODING NRC INTERACTING FACTOR-1 (NIF-1)

(75) Inventors: Muktar A. Mahajan, New York, NY (US); Herbert H. Samuels, New Rochelle, NY (US)

(73) Assignee: New York University, New York, NY (US)

( * ) Notice: Subject to any disclaimer, the term of this patent is extended or adjusted under 35 U.S.C. 154(b) by 283 days.

(21) Appl. No.: 10/645,250

(22) Filed: Aug. 20, 2003

(65) Prior Publication Data

US 2004/0175720 A1 Sep. 9, 2004

Related U.S. Application Data

(60) Provisional application No. 60/405,752, filed on Aug. 23, 2002.

(51) Int. Cl.
| | |
|---|---|
| C07H 21/04 | (2006.01) |
| C12N 15/00 | (2006.01) |
| C12N 1/21 | (2006.01) |
| C12N 1/15 | (2006.01) |
| C12N 5/10 | (2006.01) |

(52) U.S. Cl. ............................. 435/252.31; 435/254.11; 435/320.1; 435/325; 536/23.1; 536/23.5

(58) Field of Classification Search ...................... None
See application file for complete search history.

(56) References Cited

U.S. PATENT DOCUMENTS

| 4,788,222 | A | 11/1988 | Rice et al. | |
|---|---|---|---|---|
| 6,335,194 | B1 | 1/2002 | Bennett et al. | |
| 6,783,969 | B1 * | 8/2004 | Tang et al. | 435/219 |

OTHER PUBLICATIONS

Anzick et al., "AIB1, A Steroid Receptor Coactivator Amplified in Breast and Ovarian Cancer," *Science* 277:965-968 (1997).
Aranda et al., "Nuclear Hormone Receptors and Gene Expression," *Physiol. Rev.* 81:1269-1304 (2001).
Aravind, "The BED Finger, A Novel DNA-Binding Domain in Chromatin-Boundary-Element-Binding Proteins and Transposases," *Trends Biochem. Sci.* 25:421-423 (2000).
Blanco et al., "The Histone Acetylase PCAF is a Nuclear Receptor Coactivator," *Genes Dev.* 12:1638-1651 (1998).
Caira et al., "Cloning and Characterization of RAP250, A Novel Nuclear Receptor Coactivator," *J. Biol. Chem.* 275:5308-5317 (2000).
Chakravarti et al., "Role of CBP/P300 in Nuclear Receptor Signalling," *Nature* 383:99-103 (1996).
Chen et al., "Regulation of Transcription by a Protein Methyltransferase," *Science* 284:2174-2177 (1999).
Darimont et al., "Structure and Specificity of Nuclear Receptor-Coactivator Interactions," *Genes Dev.* 12:3343-3356 (1998).
Elbashir et al., "RNA Interference is Mediated by 21- and 22-Nucleotide RNAs," *Gene Dev.* 15(2):188-200 (2001).
Feng et al., "Hormone-Dependent Coactivator Binding to a Hydrophobic Cleft on Nuclear Receptors," *Science* 280:1747-1749 (1998).
Fondell et al., "Ligand Induction of a Transcriptionally Active Thyroid Hormone Receptor Coactivator Complex," *Proc. Natl. Acad. Sci. USA* 93:8329-8333 (1996).
Forman et al., "Half-Site Spacing and Orientation Determines Whether Thyroid Hormone and Retinoic Acid Receptors and Related Factors Bind to DNA Response Elements as Monomers, Homodimers, or Heterodimers," *Mol. Endocrinol.* 6:429-442 (1992).
Genbank Accession No. AAM54490 (Sep. 10, 2002).
Genbank Accession No. AF245115 (Jun. 24, 2000).
Genbank Accession No. AF309071 (Sep. 10, 2002).
Genbank Accession No. AF395833 (Sep. 16, 2002).
Genbank Accession No. AY079168 (Sep. 15, 2002).
Genbank Accession No. bankit447054 (Feb. 14, 2002).
Genbank Accession No. U27196 (May 31, 1996).
Genbank Accession No. XP_215941 (Jan. 28, 2003).
Gyuris et al., "Cdi1, A Human G1 and S Phase Protein Phosphatase that Associates with Cdk2," *Cell* 75:791-803 (1993).
Hadzic et al., "A 10-Amino-Acid Sequence in the N-Terminal A/B Domain of Thyroid Hormone Receptor a is Essential for Transcriptional Activation and Interaction with the General Transcription Factor TFIIB," *Mol. Cell. Biol.* 15:4507-4517 (1995).
Hanstein et al., "p300 is a Component of an Estrogen Receptor Coactivator Complex," *Proc. Natl. Acad. Sci. USA* 93:11540-11545 (1996).
Harlow et al., *Antibodies: A Laboratory Manual*, Cold Springs Harbor Laboratory, New York (1988) (Table of Contents only).
Hart et al., "Evidence for an Antagonistic Relationship Between the Boundary Element-Associated Factor BEAF and the Transcription Factor DREF," *Chromosoma* 108:375-383 (1999).
Heery et al., "A Signature Motif in Transcriptional Co-Activators Mediates Binding to Nuclear Receptors," *Nature* 387:733-736 (1997).
Iwasaki et al., "Identification and Characterization of RRM-Containing Coactivator Activator (CoAA) as TRBP-Interacting Protein, and its Splice Variant as a Coactivator Modulator (CoAM)," *J. Biol. Chem.* 276:33375-33383 (2001).

(Continued)

*Primary Examiner*—Celine Qian
*Assistant Examiner*—Jennifer Dunston
(74) *Attorney, Agent, or Firm*—Nixon Peabody LLP

(57) ABSTRACT

The present invention relates to isolated human and rat nucleic acid molecules encoding a protein or polypeptide that modulates transcriptional activation in a cell with or without collaboration with a nuclear hormone receptor transcriptional co-activator. The present invention also relates to the proteins or polypeptides encoded by those nucleic acid molecules, and antibodies against such proteins or polypeptides. The present invention also relates to a variety of uses for the nucleic acid molecules, proteins or polypeptides, and the related antibodies of the present invention, including methods of: regulating cellular proliferation, differentiation, and development; modulating the activity of a transcriptional co-activator complex and a transcription factor in cells; regulating hormone receptor activity and endocrine function in cells; and treating diabetes and insulin resistance in a subject.

6 Claims, 16 Drawing Sheets

OTHER PUBLICATIONS

Jung et al., "Molecular Coning and Characterization of CAPER, A Novel Coactivator of Activating Protein-1 and Estrogen Receptor," *J. Biol. Chem.* 277:1229-1234 (2002).

Kamei et al., "A CBP Integrator Complex Mediates Transcriptional Activation and AP-1 Inhibition by Nuclear Receptors," *Cell* 85:403-414 (1996).

Ko et al., "Thyroid Hormone Receptor-Binding Protein, an LXXLL Motif-Containing Protein, Functions as a General Coactivator," *Proc. Natl. Acad. Sci. USA* 97:6212-6217 (2000).

Lee et al., "A Nuclear Factor, ASC-2, as a Cancer-Amplified Transcriptional Coactivator Essential for Ligand-Dependent Transactivation by Nuclear Receptors in vivo," *J. Biol. Chem.* 274:34283-34293 (1999).

Li et al., "NRIF3 is a Novel Coactivator Mediating Functional Specificity of Nuclear Hormone Receptors," *Mol. Cell. Biol.* 19:7191-7202 (1999).

Lill et al., "Binding and Modulation of p53 by p300/CBP Coactivators," *Nature* 387:823-827 (1997).

Mahajan & Samuels, "Nuclear Hormone Receptor Coregulator: Role in Hormone Action, Metabolism, Growth, and Development," *Endocrine Reviews* 26(4):583-597 (2005).

Mahajan et al., "A New Family of Nuclear Receptor Coregulators That Integrate Nuclear Receptor Signaling through CREB-Binding Protein," *Mol. Cell Biol.* 20(14):5048-5063 (2000).

Mahajan et al., "NRC-Interacting Factor 1 Is a Novel Cotransducer That Interacts with and Regulates the Activity of the Nuclear Hormone Receptor Coactivator NRC," *Mol. Cell. Biol.* 22(19):6883-6894 (2002).

Mahajan et al., "The Nuclear Hormone Receptor Coactivator NRC Is a Pleiotropic Modulator Affecting Growth, Development, Apoptosis, Reproduction, and Wound Repair," *Mol. Cell. Biol.* 24(11):4994-5004 (2004).

Matzke et al., "RNA-Based Silencing Strategies in Plants," *Curr. Opin. Genet. Dev.* 11(2):221-227 (2001).

McInerney et al., "Determinants of Coactivator LXXLL Motif Specificity in Nuclear Receptor Transcriptional Activation," *Genes Dev.* 12:3357-3368 (1998).

McKenna et al., "Nuclear Receptor Coregulators: Cellular and Molecular Biology," *Endocr. Rev.* 20:321-344 (1999).

Montgomery et al, "RNA as a Target of Double-Stranded RNA-Mediated Genetic Interference in *Caenorhabditis elegans,*" *Proc. Natl. Acad. Sci. USA* 95: 15502-15507 (1998).

Neumann et al., "Gene Transfer into Mouse Lyoma Cells by Electroporation in High Electric Fields," *EMBO J.* 1: 841-45 (1982).

Park et al., "Signal-Induced Transcriptional Activation by Dif Requires the dTRAP80 Mediator Module," *Mol. Cell. Biol.* 23(4):1358-1367 (2003).

Perkins et al., "Regulation of NF-kappaB by Cyclin-Dependent Kinases Associated With the p300 Coactivator," *Science* 275:523-527 (1997).

Puigserver et al., "A Cold-Inducible Coactivator of Nuclear Receptors Linked to Adaptive Thermogenesis," *Cell* 92:829-839 (1998).

Schapira et al., "In Silico Discovery of Novel Retinoic Acid Receptor Agonist Structures," *BMC Structural Biology* 1:1 (2001).

Schapira et al., "Rational Discovery of Novel Nuclear Hormone Receptor Antagonists," *PNAS* 97(3):1008-1013 (2000).

Tabara et al., "RNAi in *C. elegans*: Soaking in the Genome Sequence," *Science* 282:430-431 (1998).

Timmons & Fire, "Specific Interference by Ingested dsRNA," *Nature* 395:854-855 (1998).

Torchia et al., "The Transcriptional Co-Activator p/CIP Binds CBP and Mediates Nuclear-Receptor Function," *Nature* 387:677-684 (1997).

Tuschl, "RNA Interference and Small Interfering RNAs," *Chembiochem* 2: 239-245 (2001).

Wang et al., "Methylation of Histone H4 at Arginine 3 Facilitating Transcriptional Activation by Nuclear Hormone Receptor," *Science* 293:853-857 (2001).

Wong et al., "Electric Field Mediated Gene Transfer," *Biochem. Biophys. Res. Commun.* 107(2):584-7 (1982).

Yang et al., "A p300/CBP-Associated Factor that Competes with the Adenoviral Oncoprotein E1A," *Nature* 382:319-324 (1996).

Zamore et al., "RNAi: Double Stranded RNA Directs the ATP-Dependent Cleavage of mRNA at 21 to 23 Nucleotide Intervals," *Cell* 101:25-33 (2000).

Zhang et al., "Two Contact Regions Between Stat1 and CBP/p300 in Interferon Gamma Signaling," *Proc. Natl. Acad. Sci. USA* 93:15092-15096 (1996).

Zhu et al., "Cloning and Characterization of PIMT, A Protein With a Methyltransferase Domain, Which Interacts With and Enhances Nuclear Receptor Coactivator PRIP Function," *Proc. Natl. Acad. Sci. USA* 98:10380-10385 (2001).

Zhu et al., "Isolation and Characterization of Peroxisome Proliferator-Activated Receptor (PPAR) Interacting Protein (PRIP) as a Coactivator for PPAR," *J. Biol. Chem.* 275:13510-13516 (2000).

* cited by examiner

```
                                              *SSQTLRPAVRQPADQ
MEENEVESSSDAAPGPGRPEEPSESGLGVGTSEAVSADSSDAAAAPGQAEADDSGVGQSS    60
DRGSRSQEEVSESSSSADPLPNSYLPDSSSVSHGPVAGVTGGPPALVHSSALPDPNMLVS   120
DCTASSSDLGSAIDKIIESTIGPDLIQNCITVTSAEDGGAETTRYLILQGPDDGAPMTSP   180
MSSSTLAHSLAAIEALADGPTSTSTCLEAQGGPSSPVQLPPASGAEEPDLQSLEAMMEVV   240
VVQQFKCKMCQYRSSTKATLLRHMRERHFRPVAAAAAAGKKGRLRKWSTSTKSQEEEGP    300
EEEDDDDIVDAGAIDDLEEDSDYNPAEDEPRGRQLRLQRPTPSTPRPRRRPGRPRKLPRL   360
EISDLPDGVEGEPLVSSQSGQSPPEPQDPEAPSSSGPGHLVAMGKVSRTPVEAGVSQSDA   420
ENAAPSCPDEHDTLPRRRGRPSRRFLGKKYRKYYYKSPKPLLRPFLCRICGSRFLSHEDL   480
RFHVNSHEAGDPQLFKCLQCSYRSRRWSSLKEHMFNHVGSKPYKCDECSYTSVYRKDVIR   540
HAAVHSRDRKKRPDPTPKLSSFPCPVCGRVYPMQKRLTQHMKTHSTEKPHMCDKCGKSFK   600
KRYTFKMHLLTHIQAVANRRFKCEFCEFVCEDKKALLNHQLSHVSDKPFKCSFCPYRTFR   660
EDFLLSHVAVKHTGAKPFACEYCHFSTRHKKNLRLHVRCRHASSFEEWGRRHPEEPPSRR   720
RPFFSLQQIEELKQQHSAAPGPPPSSPGPPEIPPEATTFQSSEAPSLLCSDTLGGATIIY   780
QQGAEESTAMATQTALDLLLNMSAQRELGGTALQVAVVKSEDVEAGLASPGGQPSPEGAT   840
PQVVTLHVAEPGGGAAAESQLGPPDLPQITLAPGPFGGTGYSVITAPPMEEGTSAPGTPY   900
SEEPAGEAAQAVVVSDTLKEAGTHYIMATDGTQLHHIELTADGSISFPSPDALASGAKWP   960
LLQCGGLPRDGPEPPSPAKTHCVGDSQSSASSPPATSKALGLAVPPSPPSAATAASKKFS  1020
CKICAEAFPGRAEMESHKRAHAGPGAFKCPDCPFSARQWPEVRAHMAQHSSLRPHQCSQC  1080
SFASKNKKDLRRHMLTHTKEKPFACHLCGQRFNRNGHLKFHIQRLHSPDGRKSGTPTARA  1140
PTQTPTQTIILNSDDETLATLHTALQSSHGVLGPERLQQALSQEHIIVAQEQTVTNQEEA  1200
AYIQEITTADGQTVQHLVTSDNQVQYIISQDGVQHLLPQEYVVVPEGHHIQVQEGQITHI  1260
QYEQGAPFLQESQIQYVPVSPGQQLVTQAQLEAAAHSAVTAVADAAMAQAQGLFGTDETV  1320
PEHIQQLQHQGIEYDVITLADD*                                       1342
```

FIG. 1A

```
              zn3                        zn4
         592 CDKCGKSFKKRYTFKMHLLTH   CEFVCEDKKALLNHQLSH
Human NIF-1  ....................   ..................
Chick NIF    ....................   .DY.......V.......
Rat NIF      ....................   ..................

zn5                        zn6
         CKICAEAFPGRAEMESHKRAH   CHLCGQRFNRNGHLKFHIQRLH
Human NIF-1  .....................  ......................
Chick NIF    LQDLHSHVYRESRNGESQESH   .QI..............M....
Rat NIF      ..V.S................   ..V...............I...

LXXLL
         ATQTALDLLLNMSAQREL
Human NIF-1  .................
Chick NIF    ........T........
Rat NIF      .................

Leu zipper-like
         LNSDDETLATLHTALQSSHGVL
Human NIF-1  ......................
Chick NIF    ...ED....Q....GQA.....
Rat NIF      ...EEE.......F..N..T..
```

FIG. 1B

SEQUENCE LISTING

<160> NUMBER OF SEQ ID NOS: 14

<210> SEQ ID NO 1
<211> LENGTH: 4439
<212> TYPE: DNA
<213> ORGANISM: Human

<400> SEQUENCE: 1

```
gacctcgtcg atgccggagt cagagaggaa cgtggctacg aaagcctcgg agtgaagttc      60 ccagaccta cgccccgctg tcaggcagcc cgccgatcag atggaggaga acgaggtgga      120
gagcagcagc gacgcggccc ctgggcctgg ccggcccgag gagccctctg agagcggcct     180
gggtgtgggc acctcagaag ccgtgtccgc cgacagcagc gacgccgcgg ccgccccggg     240
gcaggcagag gccgatgact ctggcgtggg gcaaagctcg gaccgcggca gccgttctca     300
ggaggaggta tctgagagca gctcgagcgc agacccctg cctaatagct acctccctga      360
ttcatcgtct gtgtctcatg ggccagtggc aggggtgaca ggcggtcccc cagcacttgt     420
gcactctagt gcactcccag accccaacat gctggtgtcc gactgcacag cttcctcctc     480
ggacctgggc tcggccatcg acaagatcat cgagtccacc atcgggcccg acctcatcca     540
gaactgcatc actgtgacca gtgctgagga tggcggggcc gagaccacac ggtacctgat     600
cctacagggc ccagatgatg agcccccat gacatcacca atgtccagtt ccaccttggc      660
ccacagccta gcagccattg aggccctggc agatggcccc acatccacat ccacatgcct     720
ggaggcacag ggtgggccca gctccccggt gcagctgccc ccagcctccg gtgccgaaga     780
gccggacctg cagagcctgg aggccatgat ggaggtggtg gtggtgcagc agttcaaatg     840
```

```
caagatgtgc cagtaccgga gcagcaccaa ggccacactg ctgcgccaca tgcgggaacg      900
ccacttccgt ccagtagcag cagccgcagc agcagctggt aaaaaaggac gtctacggaa      960
gtggagcacc tccaccaaga gccaagagga gagggaccag aggaggaggag acgatgatga     1020
cattgtagac gctggagcca ttgatgacct ggaggaggat agcgactata atccagctga     1080
ggatgagccc cgaggccggc agcttcggct ccagcgcccc accccagta ccccaaggcc      1140
ccgaaggaga cctggccggc cccggaagct gccccgcctg agatctcag acctcccaga      1200
tggtgtggaa ggagagcctc tagtgagttc ccagagtgga cagagccctc cagagccaca     1260
ggatcccgag ctcccagct cctcaggccc aggacacctg gtggccatgg gcaaggtgag      1320
caggacccct gtggaagctg gtgtgagcca gtcagatgca gagaacgcag ccccctcctg     1380
cccggatgag catgacactc tgccccggcg ccgaggtcga ccttccaggc gcttcctagg     1440
caagaaatac cgcaagtact attacaagtc gcccaaacca cttttgaggc ccttcctgtg     1500
ccgcatctgt ggttctcgct ttctgtccca cgaggacctg cgcttccacg tcaactccca     1560
tgaggctggc gatccccagc tcttcaagtg cctgcagtgc agctatcgtt cccgccgctg     1620
gtcctcgctc aaggagcaca tgttcaacca cgtgggcagc aagccctaca agtgtgacga     1680
gtgcagctac accagtgtct accggaagga cgtcattcgg cacgccgctg tgcacagccg     1740
ggaccggaag aagaggccag atccgactcc aaagctgagc tctttcccct gccctgtgtg     1800
tggccgtgtg tacccatgc agaaaagact cacgcagcac atgaagacgc acagcactga      1860
gaagcccac atgtgtgaca agtgtggaaa gtcctttaag aagcgctaca ccttcaaaat      1920
gcacctgctc acgcacatcc aggctgttgc caaccgcagg ttcaagtgtg agttctgtga     1980
gtttgtttgt gaagacaaga aggcactgct gaaccaccag ttgtcccacg tcagtgacaa     2040
gcccttcaaa tgcagctttt gtccctaccg caccttccga gaggacttct gctgtccca     2100
tgtggctgtc aagcacacag gggccaagcc cttcgcctgt gagtactgcc acttcagcac     2160
acggcacaag aagaacctgc gcctgcacgt acggtgccga cacgcaagca gcttcgagga     2220
atggggggagg cgccacccctg aggagccccc ctcccgccgt cgcccccttct tctctctgca     2280
gcagattgag gagctgaagc agcagcacag tgcggcccct ggaccacctc ccagttcccc     2340
aggacctcct gagataccccc cagaggcgac aactttccag tcatctgagg ctccctcatt     2400
gctctgttct gacaccctgg gcggcgccac catcatctac cagcaaggag ctgaggagtc     2460
gacagcgatg gccacgcaga cagccttgga tcttctgctg aacatgagtg ctcagcggga     2520
actggggggc acagccctgc aggtggctgt ggtgaagtcg aagatgtgg aagcagggtt      2580
agcatccct ggtgggcagc cctcccctga aggtgccact ccacaggtgg tcaccctcca      2640
cgtggcagag ccagggggcg gtgcagcagc cgagagccag ctaggccctc ctgacctacc     2700
gcagatcacc ctggcacctg gtccatttgg tgggactggc tacagtgtca tcacagcacc     2760
ccctatggag gagggaacat cagctcctgg cacaccttac agcgaggagc ccgcaggaga     2820
ggcagcccag gctgtggttg tgagtgacac cctaaaagaa gctggcaccc actacatcat     2880
ggctactgat ggtacccagt tgcaccacat tgagctcacc gcagatggct ccatctcctt     2940
cccaagtcca gatgctctgg cctctggtgc caaatggccc ctgctgcagt gtggggact      3000
gcccagagac ggccctgagc cccatctcc agccaagacc cactgcgtag gggactccca     3060
gagctctgcc tcctcacctc ctgcaaccag caaagccctg gcctggcag tgccccgtc      3120
accgccatct gcagccactg ctgcatcaaa gaagttttcc tgcaagatct gtgccgaggc     3180
```

```
cttccctggc cgagctgaga tggagagtca caagcgggcc cacgctgggc ctggtgcctt   3240
caagtgcccc gactgcccct tcagtgcccg ccagtggccc gaggtccggg cgcacatggc   3300
acagcactca agcctacggc cccaccagtg tagccagtgc agctttgcct ccaagaacaa   3360
gaaggacctg cgtcggcaca tgctgactca cacaaaggag aagcctttg catgccacct    3420 ctgcgggcag cgtttcaacc gtaacgggca cctcaagttc cacatccagc ggctgcacag   3480
tcctgatggg aggaagtcag gaaccnctac agcccgggcc cctacccaga ccccaaccca   3540
gaccatcatc ctgaacagtg atgacgaaac actggccacc ctgcacactg cactccagtc   3600
cagtcacggg gtcctgggcc agagcggct acagcaggca ctgagccagg aacacatcat    3660
cgttgcccag aacagacag tgaccaatca ggaggaagcc gcctacatcc aagagatcac    3720
cacggcagat ggccagaccg tacagcacct ggtgacctcc gacaaccagg tgcagtatat   3780
catctcccag gatggtgtcc agcacctgct cccccaggaa tatgttgtgg tccctgaagg   3840
ccatcacatc caggtacagg agggccagat cacacacatc cagtatgaac aaggagcccc   3900
gttccttcag gagtcccaga tccagtatgt gcctgtgtcc ccaggccagc agcttgtcac   3960
acaggctcaa cttgaggctg cagcacactc agctgtcaca gcagtggctg atgctgccat   4020
ggcccaagcc cagggcctgt ttggtacaga cgagacagtg cccgaacaca ttcaacagct   4080
gcagcaccag ggcatcgagt acgacgtcat caccctggcc gatgactgag ccccgagggc   4140
ccaacacaga tcatggattt cggccagct ctcctggggg taggggccca ccaggactca    4200
cctccctctt catttaggat ctccagatac tggatagcca gcatcctctc attcccaggg   4260
agccagacct gtgctgttgg ggttagggc agccatgggc cccagccagg acatgctggg    4320
tgccccagcc tgcaggcagg ctttgggaga gaaatttatt tttgtttggg tggacccact   4380
ggcctgtcag tctcaataaa gggaccggag tccagtcctg aacagcttaa aaaaaaaaa    4439
```

<210> SEQ ID NO 2
<211> LENGTH: 1357
<212> TYPE: PRT
<213> ORGANISM: Human

<400> SEQUENCE: 2

```
Ser Ser Gln Thr Leu Arg Pro Ala Val Arg Gln Pro Ala Asp Gln Met
  1               5                  10                  15

Glu Glu Asn Glu Val Glu Ser Ser Asp Ala Ala Pro Gly Pro Gly
             20                  25                  30

Arg Pro Glu Glu Pro Ser Glu Ser Gly Leu Gly Val Gly Thr Ser Glu
         35                  40                  45

Ala Val Ser Ala Asp Ser Ser Asp Ala Ala Ala Pro Gly Gln Ala
     50                  55                  60

Glu Ala Asp Asp Ser Gly Val Gly Gln Ser Ser Asp Arg Gly Ser Arg
 65                  70                  75                  80

Ser Gln Glu Glu Val Ser Glu Ser Ser Ser Ala Asp Pro Leu Pro
                 85                  90                  95

Asn Ser Tyr Leu Pro Asp Ser Ser Val Ser His Gly Pro Val Ala
            100                 105                 110

Gly Val Thr Gly Gly Pro Pro Ala Leu Val His Ser Ala Leu Pro
        115                 120                 125

Asp Pro Asn Met Leu Val Ser Asp Cys Thr Ala Ser Ser Ser Asp Leu
    130                 135                 140

Gly Ser Ala Ile Asp Lys Ile Ile Glu Ser Thr Ile Gly Pro Asp Leu
145                 150                 155                 160
```

-continued

```
Ile Gln Asn Cys Ile Thr Val Thr Ser Ala Glu Asp Gly Gly Ala Glu
            165                 170                 175

Thr Thr Arg Tyr Leu Ile Leu Gln Gly Pro Asp Asp Gly Ala Pro Met
        180                 185                 190

Thr Ser Pro Met Ser Ser Ser Thr Leu Ala His Ser Leu Ala Ala Ile
    195                 200                 205

Glu Ala Leu Ala Asp Gly Pro Thr Ser Thr Ser Thr Cys Leu Glu Ala
    210                 215                 220

Gln Gly Gly Pro Ser Ser Pro Val Gln Leu Pro Pro Ala Ser Gly Ala
225                 230                 235                 240

Glu Glu Pro Asp Leu Gln Ser Leu Glu Ala Met Met Glu Val Val Val
            245                 250                 255

Val Gln Gln Phe Lys Cys Lys Met Cys Gln Tyr Arg Ser Ser Thr Lys
            260                 265                 270

Ala Thr Leu Leu Arg His Met Arg Glu Arg His Phe Arg Pro Val Ala
        275                 280                 285

Ala Ala Ala Ala Ala Gly Lys Lys Gly Arg Leu Arg Lys Trp Ser
    290                 295                 300

Thr Ser Thr Lys Ser Gln Glu Glu Gly Pro Glu Glu Asp Asp
305                 310                 315                 320

Asp Asp Ile Val Asp Ala Gly Ala Ile Asp Leu Glu Glu Asp Ser
            325                 330                 335

Asp Tyr Asn Pro Ala Glu Asp Glu Pro Arg Gly Arg Gln Leu Arg Leu
            340                 345                 350

Gln Arg Pro Thr Pro Ser Thr Pro Arg Pro Arg Arg Pro Gly Arg
        355                 360                 365

Pro Arg Lys Leu Pro Arg Leu Glu Ile Ser Asp Leu Pro Asp Gly Val
        370                 375                 380

Glu Gly Glu Pro Leu Val Ser Ser Gln Ser Gly Gln Ser Pro Pro Glu
385                 390                 395                 400

Pro Gln Asp Pro Glu Ala Pro Ser Ser Ser Gly Pro Gly His Leu Val
            405                 410                 415

Ala Met Gly Lys Val Ser Arg Thr Pro Val Glu Ala Gly Val Ser Gln
            420                 425                 430

Ser Asp Ala Glu Asn Ala Ala Pro Ser Cys Pro Asp Glu His Asp Thr
        435                 440                 445

Leu Pro Arg Arg Arg Gly Arg Pro Ser Arg Arg Phe Leu Gly Lys Lys
    450                 455                 460

Tyr Arg Lys Tyr Tyr Tyr Lys Ser Pro Lys Pro Leu Leu Arg Pro Phe
465                 470                 475                 480

Leu Cys Arg Ile Cys Gly Ser Arg Phe Leu Ser His Glu Asp Leu Arg
            485                 490                 495

Phe His Val Asn Ser His Glu Ala Gly Asp Pro Gln Leu Phe Lys Cys
            500                 505                 510

Leu Gln Cys Ser Tyr Arg Ser Arg Arg Trp Ser Ser Leu Lys Glu His
    515                 520                 525

Met Phe Asn His Val Gly Ser Lys Pro Tyr Lys Cys Asp Glu Cys Ser
    530                 535                 540

Tyr Thr Ser Val Tyr Arg Lys Asp Val Ile Arg His Ala Ala Val His
545                 550                 555                 560

Ser Arg Asp Arg Lys Lys Arg Pro Asp Pro Thr Pro Lys Leu Ser Ser
            565                 570                 575
```

```
Phe Pro Cys Pro Val Cys Gly Arg Val Tyr Pro Met Gln Lys Arg Leu
            580                 585                 590

Thr Gln His Met Lys Thr His Ser Thr Glu Lys Pro His Met Cys Asp
        595                 600                 605

Lys Cys Gly Lys Ser Phe Lys Lys Arg Tyr Thr Phe Lys Met His Leu
    610                 615                 620

Leu Thr His Ile Gln Ala Val Ala Asn Arg Arg Phe Lys Cys Glu Phe
625                 630                 635                 640

Cys Glu Phe Val Cys Glu Asp Lys Lys Ala Leu Leu Asn His Gln Leu
                645                 650                 655

Ser His Val Ser Asp Lys Pro Phe Lys Cys Ser Phe Cys Pro Tyr Arg
            660                 665                 670

Thr Phe Arg Glu Asp Phe Leu Leu Ser His Val Ala Val Lys His Thr
        675                 680                 685

Gly Ala Lys Pro Phe Ala Cys Glu Tyr Cys His Phe Ser Thr Arg His
    690                 695                 700

Lys Lys Asn Leu Arg Leu His Val Arg Cys Arg His Ala Ser Ser Phe
705                 710                 715                 720

Glu Glu Trp Gly Arg Arg His Pro Glu Glu Pro Ser Arg Arg Arg
                725                 730                 735

Pro Phe Phe Ser Leu Gln Gln Ile Glu Glu Leu Lys Gln Gln His Ser
            740                 745                 750

Ala Ala Pro Gly Pro Pro Ser Ser Pro Gly Pro Pro Glu Ile Pro
        755                 760                 765

Pro Glu Ala Thr Thr Phe Gln Ser Ser Glu Ala Pro Ser Leu Leu Cys
    770                 775                 780

Ser Asp Thr Leu Gly Gly Ala Thr Ile Ile Tyr Gln Gln Gly Ala Glu
785                 790                 795                 800

Glu Ser Thr Ala Met Ala Thr Gln Thr Ala Leu Asp Leu Leu Leu Asn
                805                 810                 815

Met Ser Ala Gln Arg Glu Leu Gly Gly Thr Ala Leu Gln Val Ala Val
            820                 825                 830

Val Lys Ser Glu Asp Val Glu Ala Gly Leu Ala Ser Pro Gly Gly Gln
        835                 840                 845

Pro Ser Pro Glu Gly Ala Thr Pro Gln Val Val Thr Leu His Val Ala
    850                 855                 860

Glu Pro Gly Gly Gly Ala Ala Ala Glu Ser Gln Leu Gly Pro Pro Asp
865                 870                 875                 880

Leu Pro Gln Ile Thr Leu Ala Pro Gly Pro Phe Gly Gly Thr Gly Tyr
                885                 890                 895

Ser Val Ile Thr Ala Pro Pro Met Glu Glu Gly Thr Ser Ala Pro Gly
            900                 905                 910

Thr Pro Tyr Ser Glu Glu Pro Ala Gly Glu Ala Gln Ala Val Val
        915                 920                 925

Val Ser Asp Thr Leu Lys Glu Ala Gly Thr His Tyr Ile Met Ala Thr
    930                 935                 940

Asp Gly Thr Gln Leu His Ile Glu Leu Thr Ala Asp Gly Ser Ile
945                 950                 955                 960

Ser Phe Pro Ser Pro Asp Ala Leu Ala Ser Gly Ala Lys Trp Pro Leu
                965                 970                 975

Leu Gln Cys Gly Gly Leu Pro Arg Asp Gly Pro Glu Pro Ser Pro
            980                 985                 990

Ala Lys Thr His Cys Val Gly Asp Ser Gln Ser Ser Ala Ser Ser Pro
```

-continued

```
            995                 1000                1005

Pro Ala Thr Ser Lys Ala Leu Gly Leu Ala Val Pro Pro Ser Pro Pro
    1010                1015                1020

Ser Ala Ala Thr Ala Ala Ser Lys Lys Phe Ser Cys Lys Ile Cys Ala
1025                1030                1035                1040

Glu Ala Phe Pro Gly Arg Ala Glu Met Glu Ser His Lys Arg Ala His
                1045                1050                1055

Ala Gly Pro Gly Ala Phe Lys Cys Pro Asp Cys Pro Phe Ser Ala Arg
                1060                1065                1070

Gln Trp Pro Glu Val Arg Ala His Met Ala Gln His Ser Ser Leu Arg
            1075                1080                1085

Pro His Gln Cys Ser Gln Cys Ser Phe Ala Ser Lys Asn Lys Lys Asp
1090                1095                1100

Leu Arg Arg His Met Leu Thr His Thr Lys Glu Lys Pro Phe Ala Cys
1105                1110                1115                1120

His Leu Cys Gly Gln Arg Phe Asn Arg Asn Gly His Leu Lys Phe His
                1125                1130                1135

Ile Gln Arg Leu His Ser Pro Asp Gly Arg Lys Ser Gly Thr Pro Thr
            1140                1145                1150

Ala Arg Ala Pro Thr Gln Thr Pro Thr Gln Thr Ile Ile Leu Asn Ser
            1155                1160                1165

Asp Asp Glu Thr Leu Ala Thr Leu His Thr Ala Leu Gln Ser Ser His
    1170                1175                1180

Gly Val Leu Gly Pro Glu Arg Leu Gln Gln Ala Leu Ser Gln Glu His
1185                1190                1195                1200

Ile Ile Val Ala Gln Glu Gln Thr Val Thr Asn Gln Glu Glu Ala Ala
                1205                1210                1215

Tyr Ile Gln Glu Ile Thr Thr Ala Asp Gly Gln Thr Val Gln His Leu
                1220                1225                1230

Val Thr Ser Asp Asn Gln Val Gln Tyr Ile Ile Ser Gln Asp Gly Val
            1235                1240                1245

Gln His Leu Leu Pro Gln Glu Tyr Val Val Pro Glu Gly His His
    1250                1255                1260

Ile Gln Val Gln Glu Gly Gln Ile Thr His Ile Gln Tyr Glu Gln Gly
1265                1270                1275                1280

Ala Pro Phe Leu Gln Glu Ser Gln Ile Gln Tyr Val Pro Val Ser Pro
                1285                1290                1295

Gly Gln Gln Leu Val Thr Gln Ala Gln Leu Glu Ala Ala His Ser
                1300                1305                1310

Ala Val Thr Ala Val Ala Asp Ala Ala Met Ala Gln Ala Gln Gly Leu
            1315                1320                1325

Phe Gly Thr Asp Glu Thr Val Pro Glu His Ile Gln Gln Leu Gln His
            1330                1335                1340

Gln Gly Ile Glu Tyr Asp Val Ile Thr Leu Ala Asp Asp
1345                1350                1355

<210> SEQ ID NO 3
<211> LENGTH: 1342
<212> TYPE: PRT
<213> ORGANISM: Human

<400> SEQUENCE: 3

Met Glu Glu Asn Glu Val Glu Ser Ser Ser Asp Ala Ala Pro Gly Pro
  1               5                   10                  15
```

```
Gly Arg Pro Glu Glu Pro Ser Glu Ser Gly Leu Gly Val Gly Thr Ser
            20              25                  30
Glu Ala Val Ser Ala Asp Ser Ser Asp Ala Ala Ala Pro Gly Gln
        35                  40                  45
Ala Glu Ala Asp Asp Ser Gly Val Gly Gln Ser Asp Arg Gly Ser
    50                  55                  60
Arg Ser Gln Glu Glu Val Ser Glu Ser Ser Ser Ala Asp Pro Leu
65              70                  75                  80
Pro Asn Ser Tyr Leu Pro Asp Ser Ser Val Ser His Gly Pro Val
            85                  90                  95
Ala Gly Val Thr Gly Gly Pro Pro Ala Leu Val His Ser Ser Ala Leu
            100             105                 110
Pro Asp Pro Asn Met Leu Val Ser Asp Cys Thr Ala Ser Ser Ser Asp
        115                 120                 125
Leu Gly Ser Ala Ile Asp Lys Ile Ile Glu Ser Thr Ile Gly Pro Asp
    130                 135                 140
Leu Ile Gln Asn Cys Ile Thr Val Thr Ser Ala Glu Asp Gly Gly Ala
145             150                 155                 160
Glu Thr Thr Arg Tyr Leu Ile Leu Gln Gly Pro Asp Asp Gly Ala Pro
            165                 170                 175
Met Thr Ser Pro Met Ser Ser Ser Thr Leu Ala His Ser Leu Ala Ala
            180                 185                 190
Ile Glu Ala Leu Ala Asp Gly Pro Thr Ser Thr Ser Thr Cys Leu Glu
        195                 200                 205
Ala Gln Gly Gly Pro Ser Ser Pro Val Gln Leu Pro Pro Ala Ser Gly
    210                 215                 220
Ala Glu Glu Pro Asp Leu Gln Ser Leu Glu Ala Met Met Glu Val Val
225             230                 235                 240
Val Val Gln Gln Phe Lys Cys Lys Met Cys Gln Tyr Arg Ser Ser Thr
            245                 250                 255
Lys Ala Thr Leu Leu Arg His Met Arg Glu Arg His Phe Arg Pro Val
            260                 265                 270
Ala Ala Ala Ala Ala Ala Gly Lys Lys Gly Arg Leu Arg Lys Trp
        275                 280                 285
Ser Thr Ser Thr Lys Ser Gln Glu Glu Glu Gly Pro Glu Glu Glu Asp
    290                 295                 300
Asp Asp Asp Ile Val Asp Ala Gly Ala Ile Asp Asp Leu Glu Glu Asp
305             310                 315                 320
Ser Asp Tyr Asn Pro Ala Glu Asp Glu Pro Arg Gly Arg Gln Leu Arg
            325                 330                 335
Leu Gln Arg Pro Thr Pro Ser Thr Pro Arg Pro Arg Arg Pro Gly
        340                 345                 350
Arg Pro Arg Lys Leu Pro Arg Leu Glu Ile Ser Asp Leu Pro Asp Gly
        355                 360                 365
Val Glu Gly Glu Pro Leu Val Ser Ser Gln Ser Gly Gln Ser Pro Pro
    370                 375                 380
Glu Pro Gln Asp Pro Glu Ala Pro Ser Ser Ser Gly Pro Gly His Leu
385             390                 395                 400
Val Ala Met Gly Lys Val Ser Arg Thr Pro Val Glu Ala Gly Val Ser
            405                 410                 415
Gln Ser Asp Ala Glu Asn Ala Ala Pro Ser Cys Pro Asp Glu His Asp
            420                 425                 430
Thr Leu Pro Arg Arg Arg Gly Arg Pro Ser Arg Arg Phe Leu Gly Lys
```

-continued

```
            435                 440                 445
Lys Tyr Arg Lys Tyr Tyr Lys Ser Pro Lys Pro Leu Leu Arg Pro
            450                 455                 460

Phe Leu Cys Arg Ile Cys Gly Ser Arg Phe Leu Ser His Glu Asp Leu
465                 470                 475                 480

Arg Phe His Val Asn Ser His Glu Ala Gly Asp Pro Gln Leu Phe Lys
                485                 490                 495

Cys Leu Gln Cys Ser Tyr Arg Ser Arg Trp Ser Ser Leu Lys Glu
                500                 505                 510

His Met Phe Asn His Val Gly Ser Lys Pro Tyr Lys Cys Asp Glu Cys
            515                 520                 525

Ser Tyr Thr Ser Val Tyr Arg Lys Asp Val Ile Arg His Ala Ala Val
        530                 535                 540

His Ser Arg Asp Arg Lys Lys Arg Pro Asp Pro Thr Pro Lys Leu Ser
545                 550                 555                 560

Ser Phe Pro Cys Pro Val Cys Gly Arg Val Tyr Pro Met Gln Lys Arg
                565                 570                 575

Leu Thr Gln His Met Lys Thr His Ser Thr Glu Lys Pro His Met Cys
                580                 585                 590

Asp Lys Cys Gly Lys Ser Phe Lys Lys Arg Tyr Thr Phe Lys Met His
                595                 600                 605

Leu Leu Thr His Ile Gln Ala Val Ala Asn Arg Arg Phe Lys Cys Glu
            610                 615                 620

Phe Cys Glu Phe Val Cys Glu Asp Lys Lys Ala Leu Leu Asn His Gln
625                 630                 635                 640

Leu Ser His Val Ser Asp Lys Pro Phe Lys Cys Ser Phe Cys Pro Tyr
                645                 650                 655

Arg Thr Phe Arg Glu Asp Phe Leu Leu Ser His Val Ala Val Lys His
                660                 665                 670

Thr Gly Ala Lys Pro Phe Ala Cys Glu Tyr Cys His Phe Ser Thr Arg
            675                 680                 685

His Lys Lys Asn Leu Arg Leu His Val Arg Cys Arg His Ala Ser Ser
            690                 695                 700

Phe Glu Glu Trp Gly Arg Arg His Pro Glu Glu Pro Pro Ser Arg Arg
705                 710                 715                 720

Arg Pro Phe Phe Ser Leu Gln Gln Ile Glu Glu Leu Lys Gln Gln His
                725                 730                 735

Ser Ala Ala Pro Gly Pro Pro Ser Ser Pro Gly Pro Pro Glu Ile
                740                 745                 750

Pro Pro Glu Ala Thr Thr Phe Gln Ser Ser Glu Ala Pro Ser Leu Leu
                755                 760                 765

Cys Ser Asp Thr Leu Gly Gly Ala Thr Ile Ile Tyr Gln Gln Gly Ala
770                 775                 780

Glu Glu Ser Thr Ala Met Ala Thr Gln Thr Ala Leu Asp Leu Leu Leu
785                 790                 795                 800

Asn Met Ser Ala Gln Arg Glu Leu Gly Gly Thr Ala Leu Gln Val Ala
                805                 810                 815

Val Val Lys Ser Glu Asp Val Glu Ala Gly Leu Ala Ser Pro Gly Gly
                820                 825                 830

Gln Pro Ser Pro Glu Gly Ala Thr Pro Gln Val Val Thr Leu His Val
                835                 840                 845

Ala Glu Pro Gly Gly Gly Ala Ala Glu Ser Gln Leu Gly Pro Pro
            850                 855                 860
```

-continued

```
Asp Leu Pro Gln Ile Thr Leu Ala Pro Gly Pro Phe Gly Thr Gly
865                 870                 875                 880

Tyr Ser Val Ile Thr Ala Pro Pro Met Glu Glu Gly Thr Ser Ala Pro
            885                 890                 895

Gly Thr Pro Tyr Ser Glu Glu Pro Ala Gly Glu Ala Ala Gln Ala Val
            900                 905                 910

Val Val Ser Asp Thr Leu Lys Glu Ala Gly Thr His Tyr Ile Met Ala
            915                 920                 925

Thr Asp Gly Thr Gln Leu His His Ile Glu Leu Thr Ala Asp Gly Ser
        930                 935                 940

Ile Ser Phe Pro Ser Pro Asp Ala Leu Ala Ser Gly Ala Lys Trp Pro
945                 950                 955                 960

Leu Leu Gln Cys Gly Gly Leu Pro Arg Asp Gly Pro Glu Pro Pro Ser
            965                 970                 975

Pro Ala Lys Thr His Cys Val Gly Asp Ser Gln Ser Ser Ala Ser Ser
            980                 985                 990

Pro Pro Ala Thr Ser Lys Ala Leu Gly Leu Ala Val Pro Pro Ser Pro
        995                 1000                1005

Pro Ser Ala Ala Thr Ala Ala Ser Lys Lys Phe Ser Cys Lys Ile Cys
1010                1015                1020

Ala Glu Ala Phe Pro Gly Arg Ala Glu Met Glu Ser His Lys Arg Ala
1025                1030                1035                1040

His Ala Gly Pro Gly Ala Phe Lys Cys Pro Asp Cys Pro Phe Ser Ala
            1045                1050                1055

Arg Gln Trp Pro Glu Val Arg Ala His Met Ala Gln His Ser Ser Leu
            1060                1065                1070

Arg Pro His Gln Cys Ser Gln Cys Ser Phe Ala Ser Lys Asn Lys Lys
            1075                1080                1085

Asp Leu Arg Arg His Met Leu Thr His Thr Lys Glu Lys Pro Phe Ala
            1090                1095                1100

Cys His Leu Cys Gly Gln Arg Phe Asn Arg Asn Gly His Leu Lys Phe
1105                1110                1115                1120

His Ile Gln Arg Leu His Ser Pro Asp Gly Arg Lys Ser Gly Thr Pro
            1125                1130                1135

Thr Ala Arg Ala Pro Thr Gln Thr Pro Thr Gln Thr Ile Ile Leu Asn
            1140                1145                1150

Ser Asp Asp Glu Thr Leu Ala Thr Leu His Thr Ala Leu Gln Ser Ser
            1155                1160                1165

His Gly Val Leu Gly Pro Glu Arg Leu Gln Gln Ala Leu Ser Gln Glu
            1170                1175                1180

His Ile Ile Val Ala Gln Glu Gln Thr Val Thr Asn Gln Glu Glu Ala
1185                1190                1195                1200

Ala Tyr Ile Gln Glu Ile Thr Thr Ala Asp Gly Gln Thr Val Gln His
            1205                1210                1215

Leu Val Thr Ser Asp Asn Gln Val Gln Tyr Ile Ile Ser Gln Asp Gly
            1220                1225                1230

Val Gln His Leu Leu Pro Gln Glu Tyr Val Val Pro Glu Gly His
            1235                1240                1245

His Ile Gln Val Gln Glu Gly Gln Ile Thr His Ile Gln Tyr Glu Gln
            1250                1255                1260

Gly Ala Pro Phe Leu Gln Glu Ser Gln Ile Gln Tyr Val Pro Val Ser
1265                1270                1275                1280
```

-continued

```
Pro Gly Gln Gln Leu Val Thr Gln Ala Gln Leu Glu Ala Ala His
            1285                1290                1295

Ser Ala Val Thr Ala Val Ala Asp Ala Ala Met Ala Gln Ala Gln Gly
        1300                1305                1310

Leu Phe Gly Thr Asp Glu Thr Val Pro Glu His Ile Gln Gln Leu Gln
        1315                1320                1325

His Gln Gly Ile Glu Tyr Asp Val Ile Thr Leu Ala Asp Asp
    1330                1335                1340

<210> SEQ ID NO 4
<211> LENGTH: 4339
<212> TYPE: DNA
<213> ORGANISM: Human

<400> SEQUENCE: 4
```

| | | | | | |
|---|---|---|---|---|---|
| atggaggaga | acgaggtgga | gagcagcagc | gacgcggccc | ctgggcctgg | ccggcccgag | 60 |
| gagccctctg | agagcggcct | gggtgtgggc | acctcagaag | ccgtgtccgc | cgacagcagc | 120 |
| gacgccgcgg | ccgccccggg | gcaggcagag | gccgatgact | ctggcgtggg | gcaaagctcg | 180 |
| gaccgcggca | gccgttctca | ggaggaggta | tctgagagca | gctcgagcgc | agaccccctg | 240 |
| cctaatagct | acctccctga | ttcatcgtct | gtgtctcatg | ggccagtggc | agggtgaca | 300 |
| ggcggtcccc | cagcacttgt | gcactctagt | gcactcccag | accccaacat | gctggtgtcc | 360 |
| gactgcacag | cttcctcctc | ggacctgggc | tcggccatcg | acaagatcat | cgagtccacc | 420 |
| atcgggcccg | acctcatcca | gaactgcatc | actgtgacca | gtgctgagga | tggcggggcc | 480 |
| gagaccacac | ggtacctgat | cctacagggc | ccagatgatg | agccccccat | gacatcacca | 540 |
| atgtccagtt | ccaccttggc | ccacagccta | gcagccattg | aggccctggc | agatggcccc | 600 |
| acatccacat | ccacatgcct | ggaggcacag | ggtgggccca | gctccccggt | gcagctgccc | 660 |
| ccagcctccg | gtgccgaaga | gccggacctg | cagagcctgg | aggccatgat | ggaggtggtg | 720 |
| gtggtgcagc | agttcaaatg | caagatgtgc | cagtaccgga | gcagcaccaa | ggccacactg | 780 |
| ctgcgccaca | tgcgggaacg | ccacttccgt | ccagtagcag | cagccgcagc | agcagctggt | 840 |
| aaaaaaggac | gtctacggaa | gtggagcacc | tccaccaaga | gccaagagga | agagggacca | 900 |
| gaggaggagg | acgatgatga | cattgtagac | gctggagcca | ttgatgacct | ggaggaggat | 960 |
| agcgactata | atccagctga | ggatgagccc | cgaggccggc | agcttcggct | ccagcgcccc | 1020 |
| acccccagta | ccccaaggcc | ccgaaggaga | cctggccggc | cccggaagct | gccccgcctg | 1080 |
| gagatctcag | acctcccaga | tggtgtggaa | ggagagcctc | tagtgagttc | ccagagtgga | 1140 |
| cagagccctc | cagagccaca | ggatcccgag | gctcccagct | cctcaggccc | aggacacctg | 1200 |
| gtggccatgg | gcaaggtgag | caggaccccct | gtggaagctg | tgtgagcca | gtcagatgca | 1260 |
| gagaacgcag | ccccctcctg | cccggatgag | catgacactc | tgccccggcg | ccgaggtcga | 1320 |
| ccttccaggc | gcttcctagg | caagaaatac | cgcaagtact | attacaagtc | gcccaaacca | 1380 |
| cttttgaggc | ccttcctgtg | ccgcatctgt | ggttctcgct | ttctgtccca | cgaggacctg | 1440 |
| cgcttccacg | tcaactccca | tgaggctggc | gatcccagc | tcttcaagtg | cctgcagtgc | 1500 |
| agctatcgtt | cccgccgctg | gtcctcgctc | aaggagcaca | tgttcaacca | cgtgggcagc | 1560 |
| aagccctaca | gtgtgacga | gtgcagctac | accagtgtct | accggaagga | cgtcattcgg | 1620 |
| cacgccgctg | tgcacagccg | ggaccggaag | aagaggccag | atccgactcc | aaagctgagc | 1680 |
| tctttccccct | gccctgtgtg | tggccgtgtg | taccccatgc | agaaaagact | cacgcagcac | 1740 |
| atgaagacgc | acagcactga | gaagccccac | atgtgtgaca | gtgtggaaa | gtcctttaag | 1800 |

```
aagcgctaca ccttcaaaat gcacctgctc acgcacatcc aggctgttgc caaccgcagg    1860
ttcaagtgtg agttctgtga gtttgtttgt gaagacaaga aggcactgct gaaccaccag    1920
ttgtcccacg tcagtgacaa gcccttcaaa tgcagctttt gtccctaccg caccttccga    1980
gaggacttct tgctgtccca tgtggctgtc aagcacacag gggccaagcc cttcgcctgt    2040
gagtactgcc acttcagcac acggcacaag aagaacctgc gcctgcacgt acggtgccga    2100
cacgcaagca gcttcgagga atggggggagg cgccaccctg aggagccccc ctcccgccgt    2160
cgccccttct tctctctgca gcagattgag gagctgaagc agcagcacag tgcgccccct    2220
ggaccacctc ccagttcccc aggacctcct gagataccccc cagaggcgac aactttccag    2280
tcatctgagg ctccctcatt gctctgttct gacaccctgg gcggcgccac catcatctac    2340
cagcaaggag ctgaggagtc gacagcgatg gccacgcaga cagccttgga tcttctgctg    2400
aacatgagtg ctcagcggga actgggggggc acagccctgc aggtggctgt ggtgaagtcg    2460
gaagatgtgg aagcagggtt agcatcccct ggtgggcagc cctcccctga aggtgccact    2520
ccacaggtgg tcaccctcca cgtggcagag ccagggggcg gtgcagcagc cgagagccag    2580
ctaggccctc ctgacctacc gcagatcacc ctggcacctg gtccatttgg tgggactggc    2640
tacagtgtca tcacagcacc ccctatggag gagggaacat cagctcctgg cacaccttac    2700
agcgaggagc ccgcaggaga ggcagcccag gctgtggttg tgagtgacac cctaaaagaa    2760
gctggcaccc actacatcat ggctactgat ggtacccagt tgcaccacat tgagctcacc    2820
gcagatggct ccatctcctt cccaagtcca gatgctctgg cctctggtgc caaatggccc    2880
ctgctgcagt gtgggggact gcccagagac ggccctgagc cccatctccc agccaagacc    2940
cactgcgtag gggactccca gagctctgcc tcctcacctc ctgcaaccag caaagccctg    3000
ggcctggcag tgccccccgtc accgccatct gcagccactg ctgcatcaaa gaagttttcc    3060
tgcaagatct gtgccgaggc cttccctggc cgagctgaga tggagagtca caagcgggcc    3120
cacgctgggc ctggtgcctt caagtgcccc gactgcccct tcagtgcccg ccagtggccc    3180
gaggtccggg cgcacatggc acagcactca agcctacggc cccaccagtg tagccagtgc    3240
agctttgcct ccaagaacaa gaaggacctg cgtcggcaca tgctgactca cacaaaggag    3300
aagccttttg catgccacct ctgcgggcag cgtttcaacc gtaacgggca cctcaagttc    3360
cacatccagc ggctgcacag tcctgatggg aggaagtcag gaaccccctac agcccgggcc    3420 cctacccaga ccccaacccca gaccatcatc ctgaacagtg atgacgaaac actggccacc    3480
ctgcacactg cactccagtc cagtcacggg gtcctgggcc cagagcggct acagcaggca    3540
ctgagccagg aacacatcat cgttgcccag gaacagacag tgaccaatca ggaggaagcc    3600
gcctacatcc aagagatcac cacggcagat ggccagaccg tacagcacct ggtgacctcc    3660
gacaaccagg tgcagtatat catctcccag gatggtgtcc agcacctgct cccccaggaa    3720
tatgttgtgg tccctgaagg ccatcacatc caggtacagg agggccagat cacacacatc    3780
cagtatgaac aaggagcccc gttccttcag gagtcccaga tccagtatgt gcctgtgtcc    3840
ccaggccagc agcttgtcac acaggctcaa cttgaggctg cagcacactc agctgtcaca    3900
gcagtggctg atgctgccat ggcccaagcc cagggcctgt ttggtacaga cgagacagtg    3960
cccgaacaca ttcaacagct gcagcaccag ggcatcgagt acgacgtcat caccctggcc    4020
gatgactgag ccccgagggc ccaacacaga tcatggattt gcggccagct ctcctggggg    4080
tagggggcca ccaggactca cctccctctt catttaggat ctccagatac tggatagcca    4140
```

-continued

| | | | |
|---|---|---|---|
| gcatcctctc attcccaggg agccagacct gtgctgttgg ggttagggc agccatgggc | | | 4200 |
| cccagccagg acatgctggg tgccccagcc tgcaggcagg ctttgggaga gaaatttatt | | | 4260 |
| tttgtttggg tggacccact ggcctgtcag tctcaataaa gggaccggag tccagtcctg | | | 4320 |
| aacagcttaa aaaaaaaaa | | | 4339 |

<210> SEQ ID NO 5
<211> LENGTH: 2662
<212> TYPE: DNA
<213> ORGANISM: Human

<400> SEQUENCE: 5

| | | | |
|---|---|---|---|
| atggaggaga cgaggtggga gagcagcagc gacgcggccc ctgggcctgg ccggcccgag | | | 60 |
| gagccctctg agagcggcct gggtgtgggc acctcagaag ccgtgtccgc cgacagcagc | | | 120 |
| gacgccgcgg ccgccccggg gcaggcagag gccgatgact ctggcgtggg gcaaagctcg | | | 180 |
| gaccgcggca gccgttctca ggaggagta tctgagagca gctcgagcgc agacccctg | | | 240 |
| cctaatagct acctccctga ttcatcgtct gtgtctcatg gccagtggc agggtgaca | | | 300 |
| ggcggtcccc cagcacttgt gcactctagt gcactccag accccaacat gctggtgtcc | | | 360 |
| gactgcacag cttcctcctc ggacctgggc tcggccatcg acaagatcat cgagtccacc | | | 420 |
| atcgggcccg acctcatcca gaactgcatc actgtgacca gtgctgagga tggcggggcc | | | 480 |
| gagaccacac ggtacctgat cctacagggc ccagatgatg agcccccat gacatcacca | | | 540 |
| atgtccagtt cccccagttc cccaggacct cctgagatac cccagaggc gacaactttc | | | 600 |
| cagtcatctg aggctccctc attgctctgt tctgacaccc tgggcggcgc caccatcatc | | | 660 |
| taccagcaag gagctgagga gtcgacagcg atggccacgc agacagcctt ggatcttctg | | | 720 |
| ctgaacatga gtgctcagcg ggaactgggg gcacagccc tgcaggtggc tgtggtgaag | | | 780 |
| tcggaagatg tggaagcagg gttagcatcc cctggtgggc agccctcccc tgaaggtgcc | | | 840 |
| actccacagg tggtcaccct ccacgtggca gagccagggg gcggtgcagc agccgagagc | | | 900 |
| cagctaggcc ctcctgacct accgcagatc accctggcac ctggtccatt tggtgggact | | | 960 |
| ggctacagtg tcatcacagc accccctatg gaggagggaa catcagctcc tggcacacct | | | 1020 |
| tacagcgagg agcccgcagg agaggcagcc caggctgtgg ttgtgagtga caccctaaaa | | | 1080 |
| gaagctggca cccactacat catggctact gatggtaccc agttgcacca cattgagctc | | | 1140 |
| accgcagatg gctccatctc cttcccaagt ccagatgctc tggcctctgg tgccaaatgg | | | 1200 |
| cccctgctgc agtgtgggg actgcccaga gacgccctg agccccatc tccagccaag | | | 1260 |
| acccactgcg tagggactc ccagagctct gcctcctcac ctcctgcaac cagcaaagcc | | | 1320 |
| ctgggcctgg cagtgccccc gtcaccgcca tctgcagcca ctgctgcatc aaagaagttt | | | 1380 |
| tcctgcaaga tctgtgccga ggccttccct ggccgagctg agatggagag tcacaagcgg | | | 1440 |
| gcccacgctg ggcctggtgc cttcaagtgc cccgactgcc ccttcagtgc cgccagtgg | | | 1500 |
| cccgaggtcc gggcgcacat ggcacagcac tcaagcctac ggccccacca gtgtagccag | | | 1560 |
| tgcagctttg cctccaagaa caagaaggac ctgcgtcggc acatgctgac tcacacaaag | | | 1620 |
| gagaagcctt ttgcatgcca cctctgcggg cagcgtttca accgtaacgg gcacctcaag | | | 1680 |
| ttccacatcc agcggctgca cagtcctgat ggaggaagt caggaacccc tacagcccgg | | | 1740 |
| gcccctaccc agaccccaac ccagaccatc atcctgaaca gtgatgacga aacactggcc | | | 1800 |
| accctgcaca ctgcactcca gtccagtcac ggggtcctgg gcccagagcg gctacagcag | | | 1860 |
| gcactgagcc aggaacacat catcgttgcc caggaacaga cagtgaccaa tcaggaggaa | | | 1920 |

-continued

```
gccgcctaca tccaagagat caccacggca gatggccaga ccgtacagca cctggtgacc   1980
tccgacaacc aggtgcagta tatcatctcc caggatggtg tccagcacct gctccccag    2040 gaatatgttg tggtccctga aggccatcac atccaggtac aggagggcca gatcacacac   2100
atccagtatg aacaaggagc cccgttcctt caggagtccc agatccagta tgtgcctgtg   2160
tccccaggcc agcagcttgt cacacaggct caacttgagg ctgcagcaca ctcagctgtc   2220
acagcagtgg ctgatgctgc catggcccaa gcccagggcc tgtttggtac agacgagaca   2280
gtgcccgaac acattcaaca gctgcagcac agggcatcg agtacgacgt catcaccctg   2340
gccgatgact gagccccgag ggcccaacac agatcatgga tttgcggcca gctctcctgg   2400
gggtaggggg ccaccaggac tcacctccct cttcatttag gatctccaga tactggatag   2460
ccagcatcct ctcattccca gggagccaga cctgtgctgt tggggttagg ggcagccatg   2520
ggccccagcc aggacatgct gggtgcccca gcctgcaggc aggctttggg agagaaattt   2580
atttttgttt gggtggaccc actggcctgt cagtctcaat aaagggaccg gagtccagtc   2640
ctgaacagct taaaaaaaaa aa                                             2662
```

<210> SEQ ID NO 6
<211> LENGTH: 783
<212> TYPE: PRT
<213> ORGANISM: Human

<400> SEQUENCE: 6

```
Met Glu Glu Asn Glu Val Glu Ser Ser Ser Asp Ala Ala Pro Gly Pro
 1               5                  10                  15

Gly Arg Pro Glu Glu Pro Ser Glu Ser Gly Leu Gly Val Gly Thr Ser
             20                  25                  30

Glu Ala Val Ser Ala Asp Ser Ser Asp Ala Ala Ala Pro Gly Gln
         35                  40                  45

Ala Glu Ala Asp Asp Ser Gly Val Gly Gln Ser Ser Asp Arg Gly Ser
     50                  55                  60

Arg Ser Gln Glu Glu Val Ser Glu Ser Ser Ser Ala Asp Pro Leu
 65                  70                  75                  80

Pro Asn Ser Tyr Leu Pro Asp Ser Ser Val Ser His Gly Pro Val
                 85                  90                  95

Ala Gly Val Thr Gly Gly Pro Pro Ala Leu Val His Ser Ser Ala Leu
            100                 105                 110

Pro Asp Pro Asn Met Leu Val Ser Asp Cys Thr Ala Ser Ser Ser Asp
        115                 120                 125

Leu Gly Ser Ala Ile Asp Lys Ile Ile Glu Ser Thr Ile Gly Pro Asp
    130                 135                 140

Leu Ile Gln Asn Cys Ile Thr Val Thr Ser Ala Glu Asp Gly Ala
145                 150                 155                 160

Glu Thr Thr Arg Tyr Leu Ile Leu Gln Gly Pro Asp Asp Gly Ala Pro
                165                 170                 175

Met Thr Ser Pro Met Ser Ser Pro Ser Ser Pro Gly Pro Pro Glu
            180                 185                 190

Ile Pro Pro Glu Ala Thr Thr Phe Gln Ser Ser Glu Ala Pro Ser Leu
        195                 200                 205

Leu Cys Ser Asp Thr Leu Gly Gly Ala Thr Ile Ile Tyr Gln Gln Gly
    210                 215                 220

Ala Glu Glu Ser Thr Ala Met Ala Thr Gln Thr Ala Leu Asp Leu Leu
225                 230                 235                 240
```

-continued

```
Leu Asn Met Ser Ala Gln Arg Glu Leu Gly Gly Thr Ala Leu Gln Val
                245                 250                 255

Ala Val Val Lys Ser Glu Asp Val Glu Ala Gly Leu Ala Ser Pro Gly
            260                 265                 270

Gly Gln Pro Ser Pro Glu Gly Ala Thr Pro Gln Val Val Thr Leu His
        275                 280                 285

Val Ala Glu Pro Gly Gly Ala Ala Ala Glu Ser Gln Leu Gly Pro
    290                 295                 300

Pro Asp Leu Pro Gln Ile Thr Leu Ala Pro Gly Pro Phe Gly Gly Thr
305                 310                 315                 320

Gly Tyr Ser Val Ile Thr Ala Pro Pro Met Glu Glu Gly Thr Ser Ala
                325                 330                 335

Pro Gly Thr Pro Tyr Ser Glu Glu Pro Ala Gly Glu Ala Ala Gln Ala
            340                 345                 350

Val Val Val Ser Asp Thr Leu Lys Glu Ala Gly Thr His Tyr Ile Met
        355                 360                 365

Ala Thr Asp Gly Thr Gln Leu His His Ile Glu Leu Thr Ala Asp Gly
    370                 375                 380

Ser Ile Ser Phe Pro Ser Pro Asp Ala Leu Ala Ser Gly Ala Lys Trp
385                 390                 395                 400

Pro Leu Leu Gln Cys Gly Gly Leu Pro Arg Asp Gly Pro Glu Pro Pro
                405                 410                 415

Ser Pro Ala Lys Thr His Cys Val Gly Asp Ser Gln Ser Ser Ala Ser
            420                 425                 430

Ser Pro Pro Ala Thr Ser Lys Ala Leu Gly Leu Ala Val Pro Pro Ser
        435                 440                 445

Pro Pro Ser Ala Ala Thr Ala Ala Ser Lys Lys Phe Ser Cys Lys Ile
    450                 455                 460

Cys Ala Glu Ala Phe Pro Gly Arg Ala Glu Met Glu Ser His Lys Arg
465                 470                 475                 480

Ala His Ala Gly Pro Gly Ala Phe Lys Cys Pro Asp Cys Pro Phe Ser
                485                 490                 495

Ala Arg Gln Trp Pro Glu Val Arg Ala His Met Ala Gln His Ser Ser
            500                 505                 510

Leu Arg Pro His Gln Cys Ser Gln Cys Ser Phe Ala Ser Lys Asn Lys
        515                 520                 525

Lys Asp Leu Arg Arg His Met Leu Thr His Thr Lys Glu Lys Pro Phe
    530                 535                 540

Ala Cys His Leu Cys Gly Gln Arg Phe Asn Arg Asn Gly His Leu Lys
545                 550                 555                 560

Phe His Ile Gln Arg Leu His Ser Pro Asp Gly Arg Lys Ser Gly Thr
                565                 570                 575

Pro Thr Ala Arg Ala Pro Thr Gln Thr Pro Thr Gln Thr Ile Ile Leu
            580                 585                 590

Asn Ser Asp Asp Glu Thr Leu Ala Thr Leu His Thr Ala Leu Gln Ser
        595                 600                 605

Ser His Gly Val Leu Gly Pro Glu Arg Leu Gln Gln Ala Leu Ser Gln
    610                 615                 620

Glu His Ile Ile Val Ala Gln Glu Gln Thr Val Thr Asn Gln Glu Glu
625                 630                 635                 640

Ala Ala Tyr Ile Gln Glu Ile Thr Thr Ala Asp Gly Gln Thr Val Gln
                645                 650                 655
```

```
His Leu Val Thr Ser Asp Asn Gln Val Gln Tyr Ile Ile Ser Gln Asp
              660                 665                 670

Gly Val Gln His Leu Leu Pro Gln Glu Tyr Val Val Pro Glu Gly
        675                 680                 685

His His Ile Gln Val Gln Glu Gly Gln Ile Thr His Ile Gln Tyr Glu
        690                 695                 700

Gln Gly Ala Pro Phe Leu Gln Glu Ser Gln Ile Gln Tyr Val Pro Val
705                 710                 715                 720

Ser Pro Gly Gln Gln Leu Val Thr Gln Ala Gln Leu Glu Ala Ala Ala
                725                 730                 735

His Ser Ala Val Thr Ala Val Ala Asp Ala Ala Met Ala Gln Ala Gln
                740                 745                 750

Gly Leu Phe Gly Thr Asp Glu Thr Val Pro Glu His Ile Gln Gln Leu
            755                 760                 765

Gln His Gln Gly Ile Glu Tyr Asp Val Ile Thr Leu Ala Asp Asp
        770                 775                 780

<210> SEQ ID NO 7
<211> LENGTH: 2778
<212> TYPE: DNA
<213> ORGANISM: Rat
<220> FEATURE:
<221> NAME/KEY: unsure
<222> LOCATION: (2557)
<223> OTHER INFORMATION: N at position 2557 is unknown

<400> SEQUENCE: 7
atgttcaacc acgtgggcag caaaccctac aagtgtgacg aatgcagcta caccagtgtc      60
taccgcaagg atgttattcg gcatgcggcc gtgcacagcc aggaccgaaa gaagaggccg     120
gatccgaccc caaagctgag ctctttccct tgcccagtgt gtggccgtgt ataccccatg     180
cagaagagac taacacagca catgaagact cacagtacgg agaagccaca catgtgcgat     240
aagtgtggaa agtcctttaa gaagcggtac accttcaaaa tgcacttgct cacacacatc     300
caggctgttg ccaaccgcag attcaagtgt gagttctgcg agtttgtttg tgaggacaag     360
aaagcactgt tgaaccacca gctgtcccat gttagcgaca agcccttcaa atgcagcttt     420
tgtccctatc gcaccttccg tgaggacttc ctgctgtctc atgtggctgt gaagcacaca     480
ggagccaagc ccttcgcctg tgagtactgc cacttcagca ctcgccacaa gaagaacctg     540
cgcctgcatg tacggtgccg acatgcgaac agctttgagg agtgggggcg gcgccaccct     600
gaggagcctc catcccgtcg ccgccccatc ttctctttgc aacagataga aagctgaag      660 cagcagcaca gtgcggcccc tggccctccc ctcagttcag caggccccga ggcccccaa      720 gaaccagcac ctttccagtc acctgagact cccccactac tctgtcctga tgccctaggt     780
ggtgccacaa tcatctacca gcaaggcgct gaggagtcca ctgcaatggc cactcagaca     840
gccttggatc tactgttgaa catgagcgcc caacgagagc tgggggccac agccttgcag     900
gtggctgtgg tgaagtcaga ggacgtggag gcagagttga catctactgc taggcagcct     960
tcctctgaag acaccactcc acgggtggtg acacttcatg tggcagagtc agggagcagt    1020
gtggcagctg agagccagct aggcccgtct gacctacagc agattgcctt gccacctggg    1080
ccattcagtg gggccagcta cagtgtcatc acagcacccc ccgtggaggg gagggcatca    1140
gcttccggcc caccttacag ggaagaacct ccaggagagg cagcccaggc tgtggttgtg    1200
aacgacactc tcaaggaagc tggcacccac tatatcatgg cagctgatgg gacccagttg    1260
caccacattg agctgactgc agatggctcc atctccttcc caagcccaga tactctggcc    1320
```

-continued

```
cctggaacca agtggcccct gctgcagtgt ggagggccac ctagagatgg tcctgaggtt    1380
ctgtctccaa cgaagaccca ccatacggga ggctcccagg gctcttccac cccacccct    1440
gcaaccagcc atgccctagg cctgctagta ccccactccc caccgtctgc agcagcttca    1500
tcaacaaaga agttctcctg caaggtgtgc tcagaggcct tccctagccg tgcagagatg    1560
gagagtcaca agcgggccca tgctgggcct gctgccttca agtgccctga ctgcccttc    1620
agtgctcgcc aatgcccga ggtccgggct cacatggcac agcactccag tctgaggccc    1680
caccagtgca atcagtgtag cttcgcctcc aagaacaaga aggacctcag gcggcacatg    1740
ctgacacaca ccaatgagaa gcctttctca tgccacgtct gtgggcagcg tttcaacagg    1800
aacgggcacc tcaaattcca catccagcgg ctacatagca tcgatggtag aaagactggg    1860
acttctacag cccgagcccc agcccagacc atcatcctca atagtgaaga ggagacactg    1920
gccacactgc acactgcctt ccagtcgaat cacgggactc tggggacaga gaggctacag    1980
caggcactga gccaggagca tatcattgtg gcccaggaac agacagtggc caatcaggag    2040
gaagctacct acatccagga aatcacggca gatggccaga cggtacagca tctggtgacc    2100
tcagacaacc aggttcagta tatcatctct caggatggtg tccagcactt gctgcctcag    2160
gagtacgttg tggtccctga tggccatcac atccaggttc aggagggcca gatcacacac    2220
attcagtatg agcaaggcac cccattccta caggagtccc agatccagta tgtacctgta    2280
tcccccagcc agcagcttgt cacccaggct cagcttgaag ctgcagcaca ttctgctgtt    2340
acagtggctg atgctgccat ggcccaagcc cagggcctgt ttggcactga ggaggcagtg    2400
ccggaacaca ttcaacagct gcagcatcag ggcatcgagt acgacgtcat caccctctcg    2460
gatgactgag cctcaaaggc ccaacgctga tcgtggatat cggggccagc tctcctggag    2520
actagggact ttcctgtcct acttagggcc tccaganact ggacagttag tgtcccttga    2580
ctccaaagga gccagacctg tgctcttggg gggcagccaa gggctccagc caggacatgc    2640
tgggtgtgtc agcctgctgg caggctttgg gagagaaatt tatttttgtt ttgatggacc    2700
cactggctcc tgtctcaata aagggaccag agtccagctc ttgccaaaaa aaaaaaaaa    2760
aaaaaaaaaa aaaaaaaa                                                   2778
```

<210> SEQ ID NO 8
<211> LENGTH: 822
<212> TYPE: PRT
<213> ORGANISM: Rat

<400> SEQUENCE: 8

```
Met Phe Asn His Val Gly Ser Lys Pro Tyr Lys Cys Asp Glu Cys Ser
  1               5                  10                  15

Tyr Thr Ser Val Tyr Arg Lys Asp Val Ile Arg His Ala Ala Val His
             20                  25                  30

Ser Gln Asp Arg Lys Lys Arg Pro Asp Pro Thr Pro Lys Leu Ser Ser
         35                  40                  45

Phe Pro Cys Pro Val Cys Gly Arg Val Tyr Pro Met Gln Lys Arg Leu
     50                  55                  60

Thr Gln His Met Lys Thr His Ser Thr Glu Lys Pro His Met Cys Asp
 65                  70                  75                  80

Lys Cys Gly Lys Ser Phe Lys Lys Arg Tyr Thr Phe Lys Met His Leu
                 85                  90                  95

Leu Thr His Ile Gln Ala Val Ala Asn Arg Arg Phe Lys Cys Glu Phe
            100                 105                 110
```

```
Cys Glu Phe Val Cys Glu Asp Lys Lys Ala Leu Leu Asn His Gln Leu
        115                 120                 125
Ser His Val Ser Asp Lys Pro Phe Lys Cys Ser Phe Cys Pro Tyr Arg
        130                 135                 140
Thr Phe Arg Glu Asp Phe Leu Leu Ser His Val Ala Val Lys His Thr
145                 150                 155                 160
Gly Ala Lys Pro Phe Ala Cys Glu Tyr Cys His Phe Ser Thr Arg His
                165                 170                 175
Lys Lys Asn Leu Arg Leu His Val Arg Cys Arg His Ala Asn Ser Phe
            180                 185                 190
Glu Glu Trp Gly Arg Arg His Pro Glu Glu Pro Ser Arg Arg Arg
        195                 200                 205
Pro Ile Phe Ser Leu Gln Gln Ile Glu Lys Leu Lys Gln Gln His Ser
        210                 215                 220
Ala Ala Pro Gly Pro Pro Leu Ser Ser Ala Gly Pro Glu Ala Pro Gln
225                 230                 235                 240
Glu Pro Ala Pro Phe Gln Ser Pro Glu Thr Pro Pro Leu Leu Cys Pro
                245                 250                 255
Asp Ala Leu Gly Gly Ala Thr Ile Ile Tyr Gln Gln Gly Ala Glu Glu
            260                 265                 270
Ser Thr Ala Met Ala Thr Gln Thr Ala Leu Asp Leu Leu Asn Met
        275                 280                 285
Ser Ala Gln Arg Glu Leu Gly Ala Thr Ala Leu Gln Val Ala Val Val
        290                 295                 300
Lys Ser Glu Asp Val Glu Ala Glu Leu Thr Ser Thr Ala Arg Gln Pro
305                 310                 315                 320
Ser Ser Glu Asp Thr Thr Pro Arg Val Val Thr Leu His Val Ala Glu
                325                 330                 335
Ser Gly Ser Ser Val Ala Ala Glu Ser Gln Leu Gly Pro Ser Asp Leu
            340                 345                 350
Gln Gln Ile Ala Leu Pro Pro Gly Pro Phe Ser Gly Ala Ser Tyr Ser
        355                 360                 365
Val Ile Thr Ala Pro Pro Val Glu Gly Arg Ala Ser Ala Ser Gly Pro
        370                 375                 380
Pro Tyr Arg Glu Glu Pro Pro Gly Glu Ala Ala Gln Ala Val Val Val
385                 390                 395                 400
Asn Asp Thr Leu Lys Glu Ala Gly Thr His Tyr Ile Met Ala Ala Asp
                405                 410                 415
Gly Thr Gln Leu His His Ile Glu Leu Thr Ala Asp Gly Ser Ile Ser
            420                 425                 430
Phe Pro Ser Pro Asp Thr Leu Ala Pro Gly Thr Lys Trp Pro Leu Leu
        435                 440                 445
Gln Cys Gly Gly Pro Pro Arg Asp Gly Pro Glu Val Leu Ser Pro Thr
        450                 455                 460
Lys Thr His His Thr Gly Gly Ser Gln Gly Ser Ser Thr Pro Pro Pro
465                 470                 475                 480
Ala Thr Ser His Ala Leu Gly Leu Leu Val Pro His Ser Pro Pro Ser
                485                 490                 495
Ala Ala Ala Ser Ser Thr Lys Lys Phe Ser Cys Lys Val Cys Ser Glu
            500                 505                 510
Ala Phe Pro Ser Arg Ala Glu Met Glu Ser His Lys Arg Ala His Ala
        515                 520                 525
```

```
Gly Pro Ala Ala Phe Lys Cys Pro Asp Cys Pro Phe Ser Ala Arg Gln
    530                 535                 540

Trp Pro Glu Val Arg Ala His Met Ala Gln His Ser Ser Leu Arg Pro
545                 550                 555                 560

His Gln Cys Asn Gln Cys Ser Phe Ala Ser Lys Asn Lys Lys Asp Leu
                565                 570                 575

Arg Arg His Met Leu Thr His Thr Asn Glu Lys Pro Phe Ser Cys His
            580                 585                 590

Val Cys Gly Gln Arg Phe Asn Arg Asn Gly His Leu Lys Phe His Ile
        595                 600                 605

Gln Arg Leu His Ser Ile Asp Gly Arg Lys Thr Gly Thr Ser Thr Ala
    610                 615                 620

Arg Ala Pro Ala Gln Thr Ile Ile Leu Asn Ser Glu Glu Thr Leu
625                 630                 635                 640

Ala Thr Leu His Thr Ala Phe Gln Ser Asn His Gly Thr Leu Gly Thr
                645                 650                 655

Glu Arg Leu Gln Gln Ala Leu Ser Gln Glu His Ile Ile Val Ala Gln
            660                 665                 670

Glu Gln Thr Val Ala Asn Gln Glu Glu Ala Thr Tyr Ile Gln Glu Ile
        675                 680                 685

Thr Ala Asp Gly Gln Thr Val Gln His Leu Val Thr Ser Asp Asn Gln
    690                 695                 700

Val Gln Tyr Ile Ile Ser Gln Asp Gly Val Gln His Leu Leu Pro Gln
705                 710                 715                 720

Glu Tyr Val Val Pro Asp Gly His His Ile Gln Val Gln Glu Gly
                725                 730                 735

Gln Ile Thr His Ile Gln Tyr Glu Gln Gly Thr Pro Phe Leu Gln Glu
            740                 745                 750

Ser Gln Ile Gln Tyr Val Pro Val Ser Pro Ser Gln Gln Leu Val Thr
        755                 760                 765

Gln Ala Gln Leu Glu Ala Ala His Ser Ala Val Thr Val Ala Asp
    770                 775                 780

Ala Ala Met Ala Gln Ala Gln Gly Leu Phe Gly Thr Glu Glu Ala Val
785                 790                 795                 800

Pro Glu His Ile Gln Gln Leu Gln His Gln Gly Ile Glu Tyr Asp Val
                805                 810                 815

Ile Thr Leu Ser Asp Asp
            820

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 9

Leu Val Asn Leu Leu
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 10
```

```
Ala Val Asn Ala Ala
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:  Peptide

<400> SEQUENCE: 11

Leu Asp Leu Leu Leu
 1               5

<210> SEQ ID NO 12
<211> LENGTH: 122
<212> TYPE: PRT
<213> ORGANISM: Human

<400> SEQUENCE: 12

Cys Asp Lys Cys Gly Lys Ser Phe Lys Lys Arg Tyr Thr Phe Lys Met
 1               5                  10                  15

His Leu Leu Thr His Cys Glu Phe Val Cys Glu Asp Lys Lys Ala Leu
             20                  25                  30

Leu Asn His Gln Leu Ser His Ala Thr Gln Thr Ala Leu Asp Leu Leu
         35                  40                  45

Leu Asn Met Ser Ala Gln Arg Glu Leu Cys Lys Ile Cys Ala Glu Ala
     50                  55                  60

Phe Pro Gly Arg Ala Glu Met Glu Ser His Lys Arg Ala His Cys His
 65                  70                  75                  80

Leu Cys Gly Gln Arg Phe Asn Arg Asn Gly His Leu Lys Phe His Ile
                 85                  90                  95

Gln Arg Leu His Leu Asn Ser Asp Asp Glu Thr Leu Ala Thr Leu His
             100                 105                 110

Thr Ala Leu Gln Ser Ser His Gly Val Leu
         115                 120

<210> SEQ ID NO 13
<211> LENGTH: 34
<212> TYPE: PRT
<213> ORGANISM: CHICK

<400> SEQUENCE: 13

Asp Tyr Val Thr Leu Gln Asp Leu His Ser His Val Tyr Arg Glu Ser
 1               5                  10                  15

Arg Asn Gly Glu Ser Gln Glu Ser His Gln Ile Met Glu Asp Gln Gly
             20                  25                  30

Gln Ala

<210> SEQ ID NO 14
<211> LENGTH: 11
<212> TYPE: PRT
<213> ORGANISM: Rat

<400> SEQUENCE: 14

Val Ser Ser Val Ile Glu Glu Glu Phe Asn Thr
 1               5                  10
```

NUCLEIC ACID MOLECULES ENCODING NRC INTERACTING FACTOR-1 (NIF-1)

This application claims the benefit of U.S. Provisional Patent Application Ser. No. 60/405,752, filed Aug. 23, 2002.

The subject matter of this application was made with support from the United States Government under The National Institutes of Health, Grant No. DK 16636. The U.S. Government may have certain rights.

FIELD OF THE INVENTION

The present invention relates to a nucleic acid molecule encoding a protein that modulates cellular transcriptional activation, and uses thereof.

BACKGROUND OF THE INVENTION

Nuclear hormone receptors comprise a family of ligand-dependent transcription factors that have a broad effect on gene expression, growth, and development (Aranda et al., "Nuclear Hormone Receptors and Gene Expression," *Physiol. Rev.* 81:1269-1304 (2001); McKenna et al., "Nuclear Receptor Coregulators: Cellular and Molecular Biology," *Endocr. Rev.* 20:321-344 (1999); McKenna et al., "Combinatorial Control of Gene Expression by Nuclear Receptors and Coregulators," *Cell* 108:465-474 (2002)). These include the thyroid hormone receptors ("TRs") for thyroid hormone ("T3"), the retinoic acid receptors ("RARs") for all trans RA, the RARs and the retinoid X receptors ("RXRs") for 9-cis RA, vitamin D receptor ("VDR") for 1, 25-(OH)$_2$ vitamin D3, glucocorticoid receptor ("GR"), progesterone receptor ("PR"), estrogen receptors ("ERs"), and peroxisome-proliferation activated receptors ("PPARs"), which are regulated by variety of lipophilic compounds. These receptors share a similar modular structure consisting of an N-terminal "A/B" domain, a DNA-binding "C" domain, and a "D, E, and F" ligand binding domain ("LBD") (Carson-Jurica et al., "Steroid Receptor Family: Structure and Functions," *Endocr. Rev.* 11:201-218 (1990); McKenna et al., "Nuclear Receptor Coregulators: Cellular and Molecular Biology," *Endocr. Rev.* 20:321-344 (1999)). The LBDs of nuclear receptors are organized into twelve helical regions and the binding of ligand to the LBD of DNA bound receptor mediates a conformational change which recruits co-activators or co-regulators leading to transcriptional activation (McKenna et al., "Nuclear Receptor Coregulators: Cellular and Molecular Biology," *Endocr. Rev.* 20:321-344 (1999); Toney et al., "Conformational Changes in Chicken Thyroid Hormone Receptor al Induced by Binding to Ligand or to DNA," *Biochemistry* 32:2-6 (1993)).

Co-activators which have been identified include members of the p160 family (SRC-1/NCoA-1) (Kamei et al., "A CBP Integrator Complex Mediates Transcriptional Activation and AP-1 Inhibition by Nuclear Receptors," *Cell* 85:403-414 (1996); Onate et al., "Sequence and Characterization of a Coactivator of the Steroid Hormone Receptor Superfamily," *Science* 270:1354-1357 (1995)); TIF-2/GRIP-1/NCoA-2 (Hong et al., "GRIP1, A Novel Mouse Protein that Serves as a Transcriptional Coactivator in Yeast for the Hormone Binding Domains of Steroid Receptors," *Proc. Natl. Acad. Sci. USA* 93:4948-4952 (1996); Torchia et al., "The Transcriptional Co-Activator p/CIP Binds CBP and Mediates Nuclear-Receptor Function," *Nature* 387:677-684 (1997); Voegel et al., "TIF2, a 160 kDa Transcriptional Mediator for the Ligand-Dependent Activation Function AF-2 of Nuclear Receptors," *EMBO J.* 15:3667-3675 (1996)); AIB1/p/CIP/ACTR/RAC3/ TRAM-1 (Anzick et al., "AIB1, A Steroid Receptor Coactivator Amplified in Breast and Ovarian Cancer," *Science* 277:965-968 (1997); Chen et al., "Nuclear Receptor Coactivator ACTR is a Novel Histone Acetyltransferase and Forms a Multimeric Activation Complex with P/CAF and CBP/p300," *Cell* 90:569-580 (1997); Li et al., "RAC3, A Steroid/Nuclear Receptor-Associated Coactivator that is Related to SRC-1 and TIF2," *Proc. Natl. Acad. Sci. USA* 94:8479-8484 (1997); Takeshita et al., "TRAM-1, A Novel 1 60-kDa Thyroid Hormone Receptor Activator Molecule, Exhibits Distinct Properties from Steroid Receptor Coactivator-1," *J. Biol. Chem.* 272:27629-27634 (1997); Torchia et al., "The Transcriptional Co-Activator p/CIP Binds CBP and Mediates Nuclear-Receptor Function," *Nature* 387:677-684 (1997)), the CBP/p300 family (Chakravarti et al., "Role of CBP/P300 in Nuclear Receptor Signalling," *Nature* 383:99-103 (1996); Hanstein et al., "p300 is a Component of an Estrogen Receptor Coactivator Complex," *Proc. Natl. Acad. Sci. USA* 93:11540-11545 (1996); Kamei et al., "A CBP Integrator Complex Mediates Transcriptional Activation and AP-1 Inhibition by Nuclear Receptors," *Cell* 85:403-414 (1996)); RIP140 (Cavailles et al., "Nuclear Factor RIP140 Modulates Transcriptional Activation by the Estrogen Receptor," *EMBO J.* 14:3741-3751 (1995)); NRC/ASC-2/PRIP/RAP250/TRBP (Caira et al., "Cloning and Characterization of RAP250, A Novel Nuclear Receptor Coactivator," *J. Biol. Chem.* 275:5308-5317 (2000); Ko et al., "Thyroid Hormone Receptor-Binding Protein, an LXXLL Motif-Containing Protein, Functions as a General Coactivator," *Proc. Natl. Acad. Sci. USA* 97:6212-6217 (2000); Lee et al., "A Nuclear Factor, ASC-2, is a Cancer-Amplified Transcriptional Coactivator Essential for Ligand-Dependent Transactivation by Nuclear Receptors in vivo," *J. Biol. Chem.* 274:34283-34293 (1999); Mahajan et al., "A New Family of Nuclear Receptor Coregulators That Integrate Nuclear Receptor Signaling Through CREB-Binding Protein," *Mol. Cell. Biol.* 20:5048-5063 (2000); Zhu et al., "Isolation and Characterization of Peroxisome Proliferator-Activated Receptor (PPAR) Interacting Protein (PRIP) as a Coactivator for PPAR," *J. Biol. Chem.* 275:13510-13516 (2000)); PGC-1 (Puigserver et al., "A Cold-Inducible Coactivator of Nuclear Receptors Linked to Adaptive Thermogenesis," *Cell* 92:829-839 (1998)), ARA70 (Yeh et al., "Cloning and Characterization of a Specific Coactivator, ARA70, for the Androgen Receptor in Human Prostate Cells," *Proc. Natl. Acad. Sci. USA* 93:5517-5521 (1996)); p/CAF (Blanco et al., "The Histone Acetylase PCAF is a Nuclear Receptor Coactivator," *Genes Dev.* 12:1638-1651 (1998); Yang et al., "A p300/CBP-Associated Factor that Competes with the Adenoviral Oncoprotein E1A," *Nature* 382:319-324 (1996)); and NRIF3, which exhibits specificity for only the TRs and the RXRs (Li et al., "NRIF3 is a Novel Coactivator Mediating Functional Specificity of Nuclear Hormone Receptors," *Mol. Cell. Biol.* 19:7191-7202 (1999)). In addition to mediating effects of nuclear hormone receptors, certain co-activators also appear to enhance the activity of other transcription factors such as NF-kB, cFos, and cJun (Ko et al., "Thyroid Hormone Receptor-Binding Protein, an LXXLL Motif-Containing Protein, Functions as a General Coactivator," *Proc. Natl. Acad. Sci. USA* 97:6212-6217 (2000)).

The DRIPs/TRAPs (vitamin D receptor interacting proteins/thyroid receptor-associated proteins) are another class of factors which are recruited to ligand-bound nuclear hormone receptors (e.g., VDR and TR) (Fondell et al., "Ligand Induction of a Transcriptionally Active Thyroid Hormone Receptor Coactivator Complex," *Proc. Natl. Acad. Sci. USA* 93:8329-8333 (1996); Rachez et al., "Ligand-Dependent Transcription Activation by Nuclear Receptors Requires the DRIP Complex," *Nature* 398:824-828 (1999)). The DRIPs and TRAPs are multi-protein complexes which appear to be similar, if not identical, and are devoid of the p160 type of co-activators. Some of the polypeptides of the DRIP/TRAP complex also appear to be a part of the SMCC, CRSP (co-factor required for promoter specificity protein ("Sp1")) and ARC complexes (Ito et al., "Identity Between TRAP and SMCC Complexes Indicates Novel Pathways for the Function of Nuclear Receptors and Diverse Mammalian Activators," *Mol. Cell* 3:361-370 (1999); Naar et al., "Composite Co-Activator ARC Mediates Chromatin-Directed Transcriptional Activation," *Nature* 398:828-832 (1999); Ryu et al., "Purification of Transcription Cofactor Complex CRSP," *Proc. Natl. Acad. Sci. USA* 96:7137-7142 (1999)). The DRIP/TRAP complexes associate with ligand-bound TR or VDR via a ~220-kDa component referred to as PBP/TRAP220/DRIP205 (Fondell et al., "Ligand Induction of a Transcriptionally Active Thyroid Hormone Receptor Coactivator Complex," *Proc. Natl. Acad. Sci. USA* 93:8329-8333 (1996); Rachez et al., "Ligand-Dependent Transcription Activation by Nuclear Receptors Requires the DRIP Complex," *Nature* 398:824-828 (1999); Zhu et al., "Isolation and Characterization of PBP, A Protein That Interacts with Peroxisome Proliferator-Activated Receptor," *J. Biol. Chem.* 272:25500-25506 (1997)) and other components of the complex interact with other transcription factors (Ito et al., "Identity Between TRAP and SMCC Complexes Indicates Novel Pathways for the Function of Nuclear Receptors and Diverse Mammalian Activators," *Mol. Cell* 3:361-370 (1999); Malik et al., "The USA-Derived Transcriptional Coactivator PC2 is a Submodule of TRAP/SMCC and Acts Synergistically With Other PCs," *Mol. Cell* 5:753-760 (2000); Naar et al., "Composite Co-Activator ARC Mediates Chromatin-Directed Transcriptional Activation," *Nature* 398:828-832 (1999); Rachez et al., "Ligand-Dependent Transcription Activation by Nuclear Receptors Requires the DRIP Complex," *Nature* 398:824-828 (1999); Ryu et al., "Purification of Transcription Cofactor Complex CRSP," *Proc. Natl. Acad. Sci. USA* 96:7137-7142 (1999)).

The association of co-activators with receptors occurs through receptor-interacting LxxLL modules of the co-activator (Darimont et al., "Structure and Specificity of Nuclear Receptor-Coactivator Interactions," *Genes Dev.* 12:3343-3356 (1998); Heery et al., "A Signature Motif in Transcriptional Co-Activators Mediates Binding to Nuclear Receptors," *Nature* 387:733-736 (1997); Mahajan et al., "A New Family of Nuclear Receptor Coregulators That Integrate Nuclear Receptor Signaling Through CREB-Binding Protein," *Mol. Cell. Biol.* 20:5048-5063 (2000); McInerney et al., "Determinants of Coactivator LXXLL Motif Specificity in Nuclear Receptor Transcriptional Activation," *Genes Dev.* 12:3357-3368 (1998)), which bind to a hydrophobic cleft in the ligand-bound receptor formed by several regions of the LBD (Darimont et al., "Structure and Specificity of Nuclear Receptor-Coactivator Interactions," *Genes Dev.* 12:3343-3356 (1998); Feng et al., "Hormone-Dependent Coactivator Binding to a Hydrophobic Cleft on Nuclear Receptors," *Science* 280:1747-1749 (1998); Nolte et al., "Ligand Binding and Co-activator Assembly of the Peroxisome Proliferator-Activated Receptor-γ," *Nature* 395:137-143 (1998)). The p160 family of co-activators, RIP140, and TRAP220/DRIP205 contain multiple LxxLL motifs (Heery et al., "A Signature Motif in Transcriptional Co-Activators Mediates Binding to Nuclear Receptors," *Nature* 387:733-736 (1997)) which is consistent with the idea that a single molecule of the co-activator can bind a nuclear receptor dimer in vivo (Darimont et al., "Structure and Specificity of Nuclear Receptor-Coactivator Interactions," *Genes Dev.* 12:3343-3356 (1998); McInerney et al., "Determinants of Coactivator LXXLL Motif Specificity in Nuclear Receptor Transcriptional Activation," *Genes Dev.* 12:3357-3368 (1998)).

The cloning and characterization of NRC (Nuclear Receptor Co-activator) (Mahajan et al., "A New Family of Nuclear Receptor Coregulators That Integrate Nuclear Receptor Signaling Through CREB-Binding Protein," *Mol. Cell. Biol.* 20:5048-5063 (2000)) (also referred to as ASC-2/PRIP/RAP250/TRBP) from rat and human cells which acts as a potent co-activator for nuclear hormone receptors (Mahajan et al., "A New Family of Nuclear Receptor Coregulators That Integrate Nuclear Receptor Signaling Through CREB-Binding Protein," *Mol. Cell. Biol.* 20:5048-5063 (2000)) and other transcription factors such as cFos, cJun, and NF-kB (Ko et al., "Thyroid Hormone Receptor-Binding Protein, an LXXLL Motif-Containing Protein, Functions as a General Coactivator," *Proc. Natl. Acad. Sci. USA* 97:6212-6217 (2000)) was previously reported. NRC is organized into several modular domains which appear to play an important role in its function as a co-activator/co-regulator for nuclear hormone receptors. NRC contains one functional LxxLL motif (LxxLL-1) that binds all nuclear receptors with high affinity. This appears to occur through the formation of NRC dimers, thereby contributing two LxxLL motifs to bind nuclear receptor dimers (Mahajan et al., "A New Family of Nuclear Receptor Coregulators That Integrate Nuclear Receptor Signaling Through CREB-Binding Protein," *Mol. Cell. Biol.* 20:5048-5063 (2000)). A region containing a second LxxLL motif (LxxLL-2) appears to be highly selective for estrogen-bound ER. NRC harbors a potent N-terminal activation domain ("AD1"), which is as active as VP16 activation domain, and a second activation domain ("AD2") which overlaps with the receptor interacting LxxLL-1 region. Receptor binding mediates a conformational change in NRC, resulting in enhanced activity of the co-activator (Mahajan et al., "A New Family of Nuclear Receptor Coregulators That Integrate Nuclear Receptor Signaling Through CREB-Binding Protein," *Mol. Cell. Biol.* 20:5048-5063 (2000)). The C-terminal region of NRC appears to function as a modulatory domain which influences the overall activity of NRC. NRC binds CBP/p300 with high affinity in vivo (Mahajan et al., "A New Family of Nuclear Receptor Coregulators That Integrate Nuclear Receptor Signaling Through CREB-Binding Protein," *Mol. Cell. Biol.* 20:5048-5063 (2000)) and in vitro (Ko et al., "Thyroid Hormone Receptor-Binding Protein, an LXXLL Motif-Containing Protein, Functions as a General Coactivator," *Proc. Natl. Acad. Sci. USA* 97:6212-6217 (2000)) suggesting that NRC may be an important functional component of CBP/p300 complexes in the cell.

CBP and p300, which exhibit intrinsic histone acetyl transferase activity ("HAT'), function as transcriptional integrators for multiple factors including p/CAF (a HAT) (Yang et al., "A p300/CBP-Associated Factor that Competes With the Adenoviral Oncoprotein E1A," *Nature* 382:319-324 (1996)), NF-kB (Perkins et al., "Regulation of NF-kappaB by Cyclin-Dependent Kinases Associated With the p300 Coactivator," *Science* 275:523-527 (1997)), the STATs (Zhang et al., "Two Contact Regions Between Stat1 and CBP/p300 in Interferon Gamma Signaling," *Proc. Natl.*

Acad. Sci. USA 93:15092-15096 (1996)), nuclear hormone receptors (Chakravarti et al., "Role of CBP/P300 in Nuclear Receptor Signalling," Nature 383:99-103 (1996); Hanstein et al., "p300 is a Component of an Estrogen Receptor Coactivator Complex," Proc. Natl. Acad. Sci. USA 93:11540-11545 (1996); Kamei et al., "A CBP Integrator Complex Mediates Transcriptional Activation and AP-1 Inhibition by Nuclear Receptors," Cell 85:403-414 (1996)), the p160 family (Torchia et al., "The Transcriptional Co-Activator p/CIP Binds CBP and Mediates Nuclear-Receptor Function," Nature 387:677-684 (1997); Voegel et al., "The Coactivator TIF2 Contains Three Nuclear Receptor-Binding Motifs and Mediates Transactivation Through CBP Binding-Dependent and -Independent Pathways," EMBO J. 17:507-519 (1998)), E1A (Chakravarti et al., "A Viral Mechanism for Inhibition of p300 and PCAF Acetyltransferase Activity," Cell 96:393-403 (1999)), p53, (Lill et al., "Binding and Modulation of p53 by p300/CBP Coactivators," Nature 387:823-827 (1997)), and NRC (Ko et al., "Thyroid Hormone Receptor-Binding Protein, an LXXLL Motif-Containing Protein, Functions as a General Coactivator," Proc. Natl. Acad. Sci. USA 97:6212-6217 (2000); Mahajan et al., "A New Family of Nuclear Receptor Coregulators That Integrate Nuclear Receptor Signaling Through CREB-Binding Protein," Mol. Cell. Biol. 20:5048-5063 (2000)). Although NRC appears to associate With CBP in vivo (Mahajan et al., "A New Family of Nuclear Receptor Coregulators That Integrate Nuclear Receptor Signaling Through CREB-Binding Protein," Mol. Cell. Biol. 20:5048-5063 (2000)), the identity of other factors that are part of this or other NRC complexes that play a role in the action of NRC are unknown. NRC Interacting Factor-1 ("NIF-1"), which associates with and enhances the activity of NRC in vivo, is a novel nuclear protein of the recently proposed BED-finger domain family (Aravind, "The BED Finger, A Novel DNA-Binding Domain in Chromatin-Boundary-Element-Binding Proteins and Transposases," Trends Biochem. Sci. 25:421-423 (2000)) containing six zinc-fingers which directly interacts with NRC but not with nuclear hormone receptors. Although NIF-1 does not bind directly to nuclear hormone receptors, it markedly enhances their ligand-dependent transcriptional activity in vivo. In addition, like NRC, NIF-1 also enhances the activities of cFos and cJun in vivo. Because nuclear hormone receptors are involved in human gene expression, and growth and development, the ability to regulate hormone receptors at the cellular level would provide a powerful tool for diagnosis and treatment in a wide variety of human disease conditions. What is needed now is the isolation and characterization of the nucleotide sequence of a factor which regulates nuclear hormone receptors at the molecular level. Also needed are methods using such a factor for the modulation of transcription factors in human cells, so that endocrine function and cell growth and development can be manipulated for the prevention and treatment of human disease.

The present invention is directed to overcoming these and other deficiencies in the art.

SUMMARY OF THE INVENTION

The present invention relates to an isolated human nucleic acid molecule encoding a protein or polypeptide that modulates transcriptional activation in a cell with or without collaboration with a nuclear hormone receptor transcriptional co-activator.

The present invention also relates to an antisense nucleic acid molecule derived from a nucleic acid molecule encoding for a protein or polypeptide that modulates transcriptional activation in a cell with or without collaboration with a nuclear hormone receptor transcriptional co-activator.

Another aspect of the present invention is an isolated protein or polypeptide that modulates transcriptional activation in a cell with or without collaboration with a nuclear hormone receptor transcriptional co-activator.

The present invention also relates to an isolated antibody or binding portion thereof raised against a protein or polypeptide that modulates transcriptional activation in a cell with or without collaboration with a nuclear hormone receptor transcriptional co-activator.

Another aspect of the present invention is a method of regulating cell proliferation. This method involves transfecting a cell with the isolated human nucleic acid molecule encoding a protein or polypeptide that modulates transcriptional activation in a cell with or without collaboration with a nuclear hormone receptor transcriptional co-activator, under conditions effective to regulate cell proliferation.

The present invention also relates to a method of regulating differentiation of a cell. This method involves transfecting a cell with the isolated human nucleic acid molecule encoding a protein or polypeptide that modulates transcriptional activation in a cell with or without collaboration with a nuclear hormone receptor transcriptional co-activator under conditions effective to regulate differentiation of the cell.

Yet another aspect of the present invention is a method of regulating development of a cell. This method involves transfecting a cell with the isolated human nucleic acid molecule encoding a protein or polypeptide that modulates transcriptional activation in a cell with or without collaboration with a nuclear hormone receptor transcriptional co-activator under conditions effective to regulate development of the cell.

The present invention also relates to a method of modulating activity of a transcriptional co-activator complex in a cell. This method involves transfecting a cell with an isolated human nucleic acid molecule encoding a protein or polypeptide that modulates transcriptional activation in a cell with or without collaboration with a nuclear hormone receptor transcriptional co-activator, or a fragment thereof, under conditions effective to modulate activity of a transcriptional co-activator complex in the cell.

The present invention also relates to another method of modulating activity of a transcriptional co-activator complex in a cell. This method involves transfecting a cell with an antisense nucleic acid molecule that is derived from the isolated human nucleic acid molecule encoding a protein or polypeptide which modulates transcriptional activation in a cell with or without collaboration with a nuclear hormone receptor transcriptional co-activator, under conditions effective to modulate activity of a transcriptional co-activator complex in the cell.

The present invention also relates to yet another method of modulating activity of a transcriptional co-activator complex in a cell. This method involves contacting a cell with an isolated protein or polypeptide that modulates transcriptional activation in a cell with or without collaboration with a nuclear hormone receptor transcriptional co-activator under conditions effective to modulate activity of a transcriptional co-activator complex in the cell.

The present invention relates to yet another method of modulating activity of a transcriptional co-activator complex in a cell. This method involves contacting a cell with an antibody, or a binding portion thereof, raised against a protein or polypeptide that modulates transcriptional activation in a cell with or without collaboration with a nuclear hormone receptor transcriptional co-activator, under conditions effective to modulate activity of a transcriptional co-activator complex in the cell.

The present invention also relates to a method of regulating hormone receptor activity in a cell. This method involves contacting a cell with an isolated protein or polypeptide that modulates transcriptional activation in a cell with or without collaboration with a nuclear hormone receptor transcriptional co-activator under conditions effective to regulate hormone receptor activity in the cell.

The present invention relates to yet another method of regulating hormone receptor activity in a cell. This method involves contacting a cell with an antibody, or a binding portion thereof, raised against a protein or polypeptide that modulates transcriptional activation in a cell with or without collaboration with a nuclear hormone receptor transcriptional co-activator, under conditions effective to regulate hormone receptor activity in the cell.

The present invention also relates to another method of regulating hormone receptor activity in a cell. This method involves transfecting a cell with an isolated human nucleic acid molecule encoding a protein or polypeptide that modulates transcriptional activation in a cell with or without collaboration with a nuclear hormone receptor transcriptional co-activator under conditions effective to regulate hormone receptor activity in the cell.

Another aspect of the present invention is yet another method of regulating hormone receptor activity in a cell. This method involves transfecting a cell with an antisense nucleic acid molecule that is derived from the isolated human nucleic acid molecule encoding a protein or polypeptide that modulates transcriptional activation in a cell with or without collaboration with a nuclear hormone receptor transcriptional co-activator, under conditions effective to regulate hormone receptor activity in the cell.

The present invention also relates to a method of modulating activity of a transcription factor in a cell. This method involves transfecting a cell with an isolated human nucleic acid molecule encoding a protein or polypeptide that modulates transcriptional activation in a cell with or without collaboration with a nuclear hormone receptor transcriptional co-activator under conditions effective to modulate activity of transcription factor in the cell.

The present invention also relates to another method of modulating activity of a transcription factor in a cell. This method involves transfecting a cell with an antisense nucleic acid molecule that is derived from the isolated human nucleic acid molecule encoding a protein or polypeptide that modulates transcriptional activation in a cell with or without collaboration with a nuclear hormone receptor transcriptional co-activator, under conditions effective to modulate activity of transcription factor in the cell.

The present invention also relates to a method of modulating endocrine function in a subject. This method involves treating a subject with an isolated human nucleic acid molecule encoding a protein or polypeptide which modulates transcriptional activation in a cell with or without collaboration with a nuclear hormone receptor transcriptional co-activator under conditions effective to modulate endocrine function in the subject.

Another aspect of the present invention relates to another method of modulating endocrine function in a subject. This method involves treating a subject with an antisense nucleic acid molecule that is derived from the isolated human nucleic acid molecule encoding a protein or polypeptide which modulates transcriptional activation in a cell with or without collaboration with a nuclear hormone receptor transcriptional co-activator, under conditions effective to modulate endocrine function in the subject.

The present invention also relates to yet another method of modulating endocrine function in a subject. This method involves treating a subject with a protein or polypeptide that modulates transcriptional activation in a cell with or without collaboration with a nuclear hormone receptor transcriptional co-activator under conditions effective to modulate endocrine function in the subject.

The present invention relates to another method of modulating endocrine function in a subject. This method involves contacting a cell with an antibody, or a binding portion thereof, raised against a protein or polypeptide that modulates transcriptional activation in a cell with or without collaboration with a nuclear hormone receptor transcriptional co-activator, under conditions effective to modulate endocrine function in the subject.

The present invention also relates to a method of treating diabetes. This method involves treating a subject having diabetes with a protein or polypeptide that modulates transcriptional activation in a cell with or without collaboration with a nuclear hormone receptor transcriptional co-activator, under conditions effective to treat diabetes.

The present invention also relates to another method of treating diabetes. This method involves treating a subject having diabetes with an antibody, or a binding portion thereof, raised against a protein or polypeptide which modulates transcriptional activation in a cell with or without collaboration with a nuclear hormone receptor transcriptional co-activator, under conditions effective to treat diabetes.

The present invention also relates to a method of treating insulin resistance in a subject. This method involves treating a subject having insulin resistance with a protein or polypeptide that modulates transcriptional activation in a cell with or without collaboration with a nuclear hormone receptor transcriptional co-activator under conditions effective to treat insulin resistance.

Another aspect of the present invention is a rat nucleic acid molecule encoding a protein or polypeptide that modulates transcriptional activation in a cell with or without collaboration with a nuclear hormone receptor transcriptional co-activator.

The present invention also relates to nucleic acid constructs, expression vectors, and host cells having an isolated human nucleic acid molecule encoding a protein or polypeptide that modulates transcriptional activation in a cell with or without collaboration with a nuclear hormone receptor transcriptional co-activator.

The present invention also relates to nucleic acid constructs, expression vectors, and host cells having an isolated rat nucleic acid molecule encoding a protein or polypeptide that modulates transcriptional activation in a cell with or without collaboration with a nuclear hormone receptor transcriptional co-activator.

The present invention discloses and characterizes the nucleotide and protein sequences of the novel nuclear protein, NIF-1, which is an example of an emerging new class of co-regulators (also referred to herein as "co-transducers"). Co-transducers such as NIF-1 act as part of a complex in vivo to modulate nuclear hormone receptor co-activator activity. Nuclear hormone receptors are involved in the development and differentiation of skin, bone, and behavioral centers in the brain. Nuclear receptors are also involved in maintaining the homeostasis of bile acids, cholesterol, and lipid metabolism. The present invention provides probes and other tools useful for investigating endocrine function at the cellular level and for use as therapeutic tools for the manipulation of cellular functions related to a variety of normal or disease conditions in mammals, including humans.

BRIEF DESCRIPTION OF THE DRAWINGS

FIGS. 1A-C show the sequence and predicted domain structure of NIF proteins. FIG. 1A shows the amino acid sequence (SEQ ID NO: 2) encoded by NIF-1 (SEQ. ID. NO: 1), including the partially translated region upstream of the encoded NIF-1 protein. The functional domains of the human NIF-1 protein (SEQ ID NO: 3) are designated. NIF-1 mRNA contains an open reading frame of 1342 amino acids. The initiator Met, indicated by the arrow head, is preceded by a short open reading frame and an inframe stop codon. DE, an acidic region rich in Asp and Glu, is underlined. Zinc-fingers 1 through 6 are boxed. Leucine zipper-like motif is indicated in bold and boxed. The LxxLL motif is boxed and lightly shaded. The leucine zipper-like motif is indicated in bold and boxed. The amino acid sequence within the arrows (which includes the DE stretch and zinc-fingers 1 through 4) is absent in NIF-2, an isoform of NIF-1. The nucleotide and amino acid sequences of NIF-1 and NIF-2 have been deposited in the GenBank under Accession No. AF395833. FIG. 1B shows the similarity of the zinc-fingers, LxxLL, and leucine zipper-like domains in human (SEQ ID NO: 12), rat (SEQ ID NO: 13), and chicken (SEQ ID NO: 14) NIFs. The region of comparison include amino acids between 592 and 1172 containing zinc-fingers 5 and 6, and the LxxLL and leucine zipper regions. FIG. 1C is a comparison of schematic representations of the functional domains identified in human NIF-1, NIF-2, and the partial rat NIF clone. D/E represents an Asp and Glu rich acidic amino acid stretch of ~35 amino acids. The LxxLL motif corresponds to the amino acids, LDLLL (SEQ ID NO: 11). Zinc-fingers of C2H2 type are dispersed and are represented by numbers 1 through 6. LZ indicates a leucine zipper-like motif localized at the C-terminus. NIF-2 was identified by sequencing an EST clone (BE29723 1) and appears to be an alternatively spliced isoform of human NIF-1. Rat NIF is a partial clone isolated from the GH4C1 pJG4-5 cDNA library deposited to GenBank under Accession Nos. AF309071 and AY079168.

In FIG. 2A, GFP-NIF-1 was transfected into COS1 cells and GFP fluorescence was detected in the nucleus (green). In FIG. 2B, the nucleus was also stained with Hoechst stain (blue). FIG. 2C shows the GFP-NIF-1 fluorescence overlapped with nuclear Hoechst stain.

FIG. 5, row "a", is a schematic representation of the functional domains identified in human NIF-1. Various NIF constructs, shown in FIGS. 5, rows "b-g", were generated as B42 fusions and tested against each of the LexA-fusions of NRC shown in FIG. 6A (NRC, rows "a-g"), in two-hybrid interaction assays. Rat NIF is the original isolate from the GH4C1 library, while NIF-2 is an isoform of human NIF-1 that lacks amino acids 185 to 743 which include the DE region and zinc-fingers 1-4. The numbers correspond to amino acids. All the NIF fragments containing the NRC interaction domain (NRC-ID) interacted with NRC in two hybrid assays.

FIG. 6A shows the interaction of NIF-1 with NRC in yeast. Each of the LexA-NRC fusions was tested for interaction with various constructs of NIF-1 (as described in FIG. 5 as "a-g") expressed as B42 fusions. All the fragments of NRC (labeled "a-g") containing the NIF-ID interact with NIF-1 clones containing the NRC Interacting Domain (NRC-ID). Mutant fragments depicted are NRC clones containing mutations in the LxxLL-1 receptor interaction motif in which LVNLL (SEQ ID NO: 9) was changed to AVNAA (SEQ ID NO: 10). FIG. 6B is picture of an agarose gel showing the binding of NIF-1 with NRC in vitro. NIF-1 was labeled with $^{35}$S-L-methionine by in vitro transcription/translation using reticulocyte lysates. Bacterially expressed and purified GST-NRC.1a (a 147 amino acid region of NRC that contains the NIF-1 interaction domain) bound to glutathione-agarose beads was incubated with $^{35}$S-labeled NIF-1. The samples were then electrophoresed in SDS gels and the $^{35}$S-NIF-1 bound to GST or GST-NRC.1a was visualized by autoradiography. One fifth of the amount of $^{35}$S-labeled NIF-1 used in the incubation was also electrophoresed in the same gel.

In FIG. 9A, HeLa cells were transfected with the ΔMTV-IR-CAT reporter and expression vectors for cTRα or hRARα and NIF-1, as indicated. The cells were incubated with T3 at 1 µM and the RAR-specific ligand TTNPB at 200 nM. All samples were analyzed in duplicate, and the experiment was repeated at least two times. In FIG. 9B, conditions were the same as for FIG. 9A, except that the MMTV-LTR-CAT reporter and an hGR expression vector were co-transfected with (+) or without (−) 500 nM dexamethasone ("Dex").

In FIG. 10A, cells were co-transfected with the μMTV-IR-CAT reporter alone and with (+) or without (−) the NIF-1 or NRC expression plasmids at various concentrations. T3 ligand was at 1 μM. Each sample was analyzed in duplicate, and the experiment was repeated at least two times with similar results. FIG. 10B conditions were the same as for FIG. 10A, except that the RXR-specific ligand LG100153 and the RXR/RAR ligand 9-cis RA were each used at 200 nM.

FIG. 11A shows the results of transfecting the −73 collagenase-CAT reporter plasmid driven by AP1 (cFos and/or cJun) with 1 μg and 3 μg of the expression plasmids for NRC or NIF-1. The samples were analyzed in duplicate, and the experiment was repeated at least twice with similar results. FIG. 11B shows the results when the expression vector for NRC was 0.7 μg. The NIF-1 expression plasmid was 0.7 μg in lane 3 and at 1.2 μg in lanes 5-7. The vector control was used at 0.7 μg.

DETAILED DESCRIPTION OF THE INVENTION

Figure 1C:
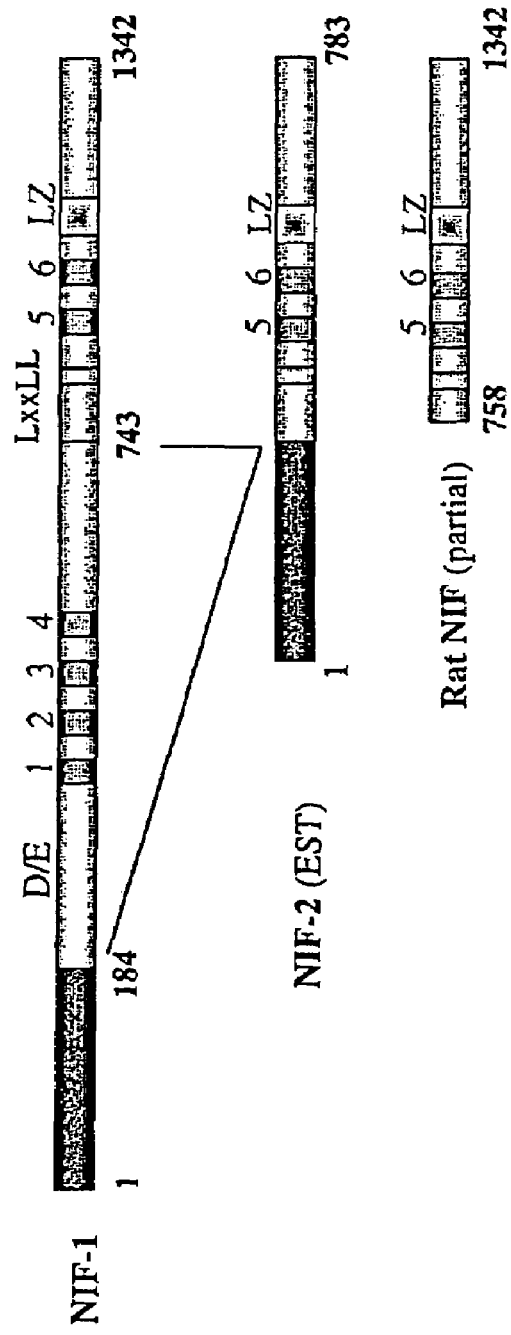

The present invention relates to an isolated human nucleic acid molecule encoding a protein or polypeptide that modulates transcriptional activation in a cell with or without collaboration with a nuclear hormone receptor transcriptional co-activator.

One suitable form of the nucleic acid of the present invention is the nucleic acid molecule having a nucleotide sequence of SEQ ID NO: 1, as follows:

```
gacctcgtcg atgccggagt cagagaggaa cgtggctacg aaagcctcgg agtgaagttc   60
ccagacccta cgccccgctg tcaggcagcc cgccgatcag atggaggaga acgaggtgga  120
gagcagcagc gacgcggccc ctgggcctgg ccgccccgag gagccctctg agagcggcct  180
gggtgtgggc acctcagaag ccgtgtccgc cgacagcagc gacgccgcgg ccgccccggg  240
gcaggcagag gccgatgact ctggcgtggg gcaaagctcg gaccgcggca gccgttctca  300
ggaggaggta tctgagagca gctcgagcgc agacccctg cctaatagct acctccctga  360
ttcatcgtct gtgtctcatg ggccagtggc aggggtgaca ggcggtcccc cagcacttgt  420
gcactctagt gcactcccag accccaacat gctggtgtcc gactgcacag cttcctcctc  480
ggacctgggc tcggccatcg acaagatcat cgagtccacc atcgggcccg acctcatcca  540
gaactgcatc actgtgacca gtgctgagga tggcggggcc gagaccacac ggtacctgat  600
cctacagggc ccagatgatg agcccccat gacatcacca atgtccagtt ccaccttggc  660
ccacagccta gcagccattg aggccctggc agatggcccc acatccacat ccacatgcct  720
ggaggcacag ggtgggccca gctcccggt gcagctgccc ccagcctccg gtgccgaaga  780
gccggacctg cagagcctgg aggccatgat ggaggtggtg gtggtgcagc agttcaaatg  840
caagatgtgc cagtaccgga gcagcaccaa ggccacactg ctgcgccaca tgcgggaacg  900
ccacttccgt ccagtagcag cagccgcagc agcagctggt aaaaaaggac gtctacggaa  960
gtggagcacc tccaccaaga gccaagagga gagggacca gaggaggagg acgatgatga 1020
cattgtagac gctggagcca ttgatgacct ggaggaggat agcgactata atccagctga 1080
ggatgagccc cgaggccggc agcttcggct ccagcgcccc acccccagta ccccaaggcc 1140
ccgaaggaga cctggccggc cccggaagct gccccgcctg gagatctcag acctcccaga 1200
tggtgtggaa ggagagcctc tagtgagttc ccagagtgga cagagccctc cagagccaca 1260
ggatcccgag gctcccagct cctcaggccc aggacacctg gtggccatgg gcaaggtgag 1320
caggacccct gtggaagctg gtgtgagcca gtcagatgca gagaacgcag cccctcctg 1380
cccggatgag catgacactc tgcccggcg ccgaggtcga ccttccaggc gcttcctagg 1440
caagaaatac cgcaagtact attacaagtc gcccaaacca cttttgaggc ccttcctgtg 1500
ccgcatctgt ggttctcgct ttctgtccca cgaggacctg cgcttccacg tcaactccca 1560
tgaggctggc gatccccagc tcttcaagtg cctgcagtgc agctatcgtt cccgccgctg 1620
```

-continued

```
gtcctcgctc aaggagcaca tgttcaacca cgtgggcagc aagccctaca agtgtgacga   1680
gtgcagctac accagtgtct accggaagga cgtcattcgg cacgccgctg tgcacagccg   1740
ggaccggaag aagaggccag atccgactcc aaagctgagc tctttcccct gccctgtgtg   1800
tggccgtgtg tacccatgc agaaaagact cacgcagcac atgaagacgc acagcactga   1860 gaagcccac atgtgtgaca agtgtggaaa gtccttaag aagcgctaca ccttcaaaat    1920
gcacctgctc acgcacatcc aggctgttgc caaccgcagg ttcaagtgtg agttctgtga   1980
gtttgtttgt gaagacaaga aggcactgct gaaccaccag ttgtcccacg tcagtgacaa   2040
gcccttcaaa tgcagctttt gtccctaccg caccttccga gaggacttct tgctgtccca   2100
tgtggctgtc aagcacacag gggccaagcc cttcgcctgt gagtactgcc acttcagcac   2160
acggcacaag aagaacctgc gcctgcacgt acggtgccga cacgcaagca gcttcgagga   2220
atgggggagg cgccaccctg aggagccccc ctcccgccgt cgccccttct tctctctgca   2280
gcagattgag gagctgaagc agcagcacag tgcggcccct ggaccacctc ccagttcccc   2340
aggacctcct gagataccccc cagaggcgac aactttccag tcatctgagg ctccctcatt   2400
gctctgttct gacaccctgg gcggcgccac catcatctac cagcaaggag ctgaggagtc   2460
gacagcgatg gccacgcaga cagccttgga tcttctgctg aacatgagtg ctcagcggga   2520 actgggggc acagccctgc aggtggctgt ggtgaagtcg gaagatgtgg aagcagggtt    2580
agcatcccct ggtgggcagc cctcccctga aggtgccact ccacaggtgg tcaccctcca   2640
cgtggcagag ccaggggcg gtgcagcagc cgagagccag ctaggccctc ctgacctacc    2700
gcagatcacc ctggcacctg gtccatttgg tgggactggc tacagtgtca tcacagcacc   2760
ccctatggag gagggaacat cagctcctgg cacaccttac agcgaggagc ccgcaggaga   2820
ggcagcccag gctgtggttg tgagtgacac cctaaaagaa gctggcaccc actacatcat   2880
ggctactgat ggtacccagt tgcaccacat tgagctcacc gcagatggct ccatctcctt   2940
cccaagtcca gatgctctgg cctctggtgc caaatggccc ctgctgcagt gtgggggact   3000
gcccagagac ggccctgagc ccccatctcc agccaagacc cactgcgtag gggactccca   3060
gagctctgcc tcctcacctc ctgcaaccag caaagccctg gcctggcag tgccccgtc    3120 accgccatct gcagccactg ctgcatcaaa gaagttttcc tgcaagatct gtgccgaggc   3180
cttccctggc cgagctgaga tggagagtca caagcgggcc cacgctgggc ctggtgcctt   3240
caagtgcccc gactgcccct tcagtgcccg ccagtggccc gaggtccggg cgcacatggc   3300
acagcactca agcctacggc cccaccagtg tagccagtgc agctttgcct ccaagaacaa   3360
gaaggacctg cgtcggcaca tgctgactca cacaaaggag aagcctttg catgccacct    3420 ctgcgggcag cgtttcaacc gtaacgggca cctcaagttc cacatccagc ggctgcacag   3480
tcctgatggg aggaagtcag gaaccctac agcccgggcc cctacccaga ccccaaccca    3540
gaccatcatc ctgaacagtg atgacgaaac actggccacc ctgcacactg cactccagtc   3600
cagtcacggg gtcctgggcc cagagcggct acagcaggca ctgagccagg aacacatcat   3660
cgttgcccag aacagacag tgaccaatca ggaggaagcc gcctacatcc aagagatcac    3720
cacggcagat ggccagaccg tacagcacct ggtgacctcc gacaaccagg tgcagtatat   3780
catctcccag gatggtgtcc agcacctgct cccccaggaa tatgttgtgg tccctgaagg   3840
ccatcacatc caggtacagg agggccagat cacacacatc cagtatgaac aaggagcccc   3900
gttccttcag gagtcccaga tccagtatgt gcctgtgtcc ccaggccagc agcttgtcac   3960
acaggctcaa cttgaggctg cagcacactc agctgtcaca gcagtggctg atgctgccat   4020
```

-continued

```
ggcccaagcc cagggcctgt ttggtacaga cgagacagtg cccgaacaca ttcaacagct  4080
gcagcaccag ggcatcgagt acgacgtcat caccctggcc gatgactgag ccccgagggc  4140
ccaacacaga tcatggattt gcggccagct ctcctggggg tagggggcca ccaggactca  4200
cctccctctt catttaggat ctccagatac tggatagcca gcatcctctc attcccaggg  4260
agccagacct gtgctgttgg ggttaggggc agccatgggc cccagccagg acatgctggg  4320
tgccccagcc tgcaggcagg ctttgggaga gaaatttatt tttgtttggg tggacccact  4380
ggcctgtcag tctcaataaa gggaccggag tccagtcctg aacagcttaa aaaaaaaaa   4439
```

SEQ ID NO: 1 encodes a novel nuclear protein of the recently proposed BED-finger domain family, referred to herein as NRC Interacting Factor-1 (NIF-1). As shown in FIG. 1A, the start site for the NIF-1 protein, indicated by the arrow head, is preceded by a short open reading frame and an inframe stop codon. The complete amino acid sequence as shown in FIG. 1A is designated as SEQ ID NO: 2.

The present invention also relates to the NIF-1 protein, encoded by SEQ ID NO: 1, where the encoded protein has an amino acid sequence corresponding to SEQ ID NO: 3, as follows:

```
Met Glu Glu Asn Glu Val Glu Ser Ser Ser Asp Ala Ala Pro Gly Pro
 1               5                  10                  15
Gly Arg Pro Glu Glu Pro Ser Glu Ser Gly Leu Gly Val Gly Thr Ser
                20                  25                  30
Glu Ala Val Ser Ala Asp Ser Ser Asp Ala Ala Ala Ala Pro Gly Gln
            35                  40                  45
Ala Glu Ala Asp Asp Ser Gly Val Gly Gln Ser Ser Asp Arg Gly Ser
        50                  55                  60
Arg Ser Gln Glu Glu Val Ser Glu Ser Ser Ser Ala Asp Pro Leu
65                  70                  75              80
Pro Asn Ser Tyr Leu Pro Asp Ser Ser Val Ser His Gly Pro Val
                85                  90                  95
Ala Gly Val Thr Gly Gly Pro Pro Ala Leu Val His Ser Ser Ala Leu
            100                 105                 110
Pro Asp Pro Asn Met Leu Val Ser Asp Cys Thr Ala Ser Ser Ser Asp
        115                 120                 125
Leu Gly Ser Ala Ile Asp Lys Ile Ile Glu Ser Thr Ile Gly Pro Asp
130                 135                 140
Leu Ile Gln Asn Cys Ile Thr Val Thr Ser Ala Glu Asp Gly Gly Ala
145                 150                 155                 160
Glu Thr Thr Arg Tyr Leu Ile Leu Gln Gly Pro Asp Asp Gly Ala Pro
                165                 170                 175
Met Thr Ser Pro Met Ser Ser Ser Thr Leu Ala His Ser Leu Ala Ala
            180                 185                 190
Ile Glu Ala Leu Ala Asp Gly Pro Thr Ser Thr Ser Thr Cys Leu Glu
        195                 200                 205
Ala Gln Gly Gly Pro Ser Ser Pro Val Gln Leu Pro Pro Ala Ser Gly
    210                 215                 220
Ala Glu Glu Pro Asp Leu Gln Ser Leu Glu Ala Met Met Glu Val Val
225                 230                 235                 240
Val Val Gln Gln Phe Lys Cys Lys Met Cys Gln Tyr Arg Ser Ser Thr
                245                 250                 255
Lys Ala Thr Leu Leu Arg His Met Arg Glu Arg His Phe Arg Pro Val
            260                 265                 270
Ala Ala Ala Ala Ala Ala Gly Lys Lys Gly Arg Leu Arg Lys Trp
        275                 280                 285
```

-continued

```
Ser Thr Ser Thr Lys Ser Gln Glu Glu Gly Pro Glu Glu Asp
    290                 295                 300
Asp Asp Asp Ile Val Asp Ala Gly Ala Ile Asp Asp Leu Glu Glu Asp
305                 310                 315                 320
Ser Asp Tyr Asn Pro Ala Glu Asp Glu Pro Arg Gly Arg Gln Leu Arg
                325                 330                 335
Leu Gln Arg Pro Thr Pro Ser Thr Pro Arg Pro Arg Arg Pro Gly
            340                 345                 350
Arg Pro Arg Lys Leu Pro Arg Leu Glu Ile Ser Asp Leu Pro Asp Gly
            355                 360                 365
Val Glu Gly Glu Pro Leu Val Ser Ser Gln Ser Gly Gln Ser Pro Pro
    370                 375                 380
Glu Pro Gln Asp Pro Glu Ala Pro Ser Ser Ser Gly Pro Gly His Leu
385                 390                 395                 400
Val Ala Met Gly Lys Val Ser Arg Thr Pro Val Glu Ala Gly Val Ser
                405                 410                 415
Gln Ser Asp Ala Glu Asn Ala Ala Pro Ser Cys Pro Asp Glu His Asp
            420                 425                 430
Thr Leu Pro Arg Arg Gly Arg Pro Ser Arg Arg Phe Leu Gly Lys
            435                 440                 445
Lys Tyr Arg Lys Tyr Tyr Lys Ser Pro Lys Pro Leu Leu Arg Pro
    450                 455                 460
Phe Leu Cys Arg Ile Cys Gly Ser Arg Phe Leu Ser His Glu Asp Leu
465                 470                 475                 480
Arg Phe His Val Asn Ser His Glu Ala Gly Asp Pro Gln Leu Phe Lys
                485                 490                 495
Cys Leu Gln Cys Ser Tyr Arg Ser Arg Arg Trp Ser Ser Leu Lys Glu
            500                 505                 510
His Met Phe Asn His Val Gly Ser Lys Pro Tyr Lys Cys Asp Glu Cys
    515                 520                 525
Ser Tyr Thr Ser Val Tyr Arg Lys Asp Val Ile Arg His Ala Ala Val
    530                 535                 540
His Ser Arg Asp Arg Lys Lys Arg Pro Asp Pro Thr Pro Lys Leu Ser
545                 550                 555                 560
Ser Phe Pro Cys Pro Val Cys Gly Arg Val Tyr Pro Met Gln Lys Arg
                565                 570                 575
Leu Thr Gln His Met Lys Thr His Ser Thr Glu Lys Pro His Met Cys
            580                 585                 590
Asp Lys Cys Gly Lys Ser Phe Lys Lys Arg Tyr Thr Phe Lys Met His
            595                 600                 605
Leu Leu Thr His Ile Gln Ala Val Ala Asn Arg Arg Phe Lys Cys Glu
    610                 615                 620
Phe Cys Glu Phe Val Cys Glu Asp Lys Lys Ala Leu Leu Asn His Gln
625                 630                 635                 640
Leu Ser His Val Ser Asp Lys Pro Phe Lys Cys Ser Phe Cys Pro Tyr
                645                 650                 655
Arg Thr Phe Arg Glu Asp Phe Leu Leu Ser His Val Ala Val Lys His
            660                 665                 670
Thr Gly Ala Lys Pro Phe Ala Cys Glu Tyr Cys His Phe Ser Thr Arg
            675                 680                 685
His Lys Lys Asn Leu Arg Leu His Val Arg Cys Arg His Ala Ser Ser
    690                 695                 700
Phe Glu Glu Trp Gly Arg Arg His Pro Glu Glu Pro Pro Ser Arg Arg
```

-continued

```
            705                 710                 715                 720
        Arg Pro Phe Phe Ser Leu Gln Gln Ile Glu Glu Leu Lys Gln Gln His
                            725                 730                 735
        Ser Ala Ala Pro Gly Pro Pro Ser Ser Pro Gly Pro Pro Glu Ile
                            740                 745                 750
        Pro Pro Glu Ala Thr Thr Phe Gln Ser Ser Glu Ala Pro Ser Leu Leu
                        755                 760                 765
        Cys Ser Asp Thr Leu Gly Gly Ala Thr Ile Ile Tyr Gln Gln Gly Ala
                        770                 775                 780
        Glu Glu Ser Thr Ala Met Ala Thr Gln Thr Ala Leu Asp Leu Leu Leu
        785                 790                 795                 800
        Asn Met Ser Ala Gln Arg Glu Leu Gly Gly Thr Ala Leu Gln Val Ala
                            805                 810                 815
        Val Val Lys Ser Glu Asp Val Glu Ala Gly Leu Ala Ser Pro Gly Gly
                        820                 825                 830
        Gln Pro Ser Pro Glu Gly Ala Thr Pro Gln Val Val Thr Leu His Val
                        835                 840                 845
        Ala Glu Pro Gly Gly Gly Ala Ala Ala Glu Ser Gln Leu Gly Pro Pro
        850                 855                 860
        Asp Leu Pro Gln Ile Thr Leu Ala Pro Gly Pro Phe Gly Gly Thr Gly
        865                 870                 875                 880
        Tyr Ser Val Ile Thr Ala Pro Pro Met Glu Glu Gly Thr Ser Ala Pro
                        885                 890                 895
        Gly Thr Pro Tyr Ser Glu Glu Pro Ala Gly Glu Ala Ala Gln Ala Val
                        900                 905                 910
        Val Val Ser Asp Thr Leu Lys Glu Ala Gly Thr His Tyr Ile Met Ala
                        915                 920                 925
        Thr Asp Gly Thr Gln Leu His His Ile Glu Leu Thr Ala Asp Gly Ser
        930                 935                 940
        Ile Ser Phe Pro Ser Pro Asp Ala Leu Ala Ser Gly Ala Lys Trp Pro
        945                 950                 955                 960
        Leu Leu Gln Cys Gly Gly Leu Pro Arg Asp Gly Pro Glu Pro Pro Ser
                        965                 970                 975
        Pro Ala Lys Thr His Cys Val Gly Asp Ser Gln Ser Ser Ala Ser Ser
                        980                 985                 990
        Pro Pro Ala Thr Ser Lys Ala Leu Gly Leu Ala Val Pro Pro Ser Pro
                        995                 1000                1005
        Pro Ser Ala Ala Thr Ala Ala Ser Lys Lys Phe Ser Cys Lys Ile Cys
                1010                1015                1020
        Ala Glu Ala Phe Pro Gly Arg Ala Glu Met Glu Ser His Lys Arg Ala
        1025                1030                1035                1040
        His Ala Gly Pro Gly Ala Phe Lys Cys Pro Asp Cys Pro Phe Ser Ala
                            1045                1050                1055
        Arg Gln Trp Pro Glu Val Arg Ala His Met Ala Gln His Ser Ser Leu
                        1060                1065                1070
        Arg Pro His Gln Cys Ser Gln Cys Ser Phe Ala Ser Lys Asn Lys Lys
                1075                1080                1085
        Asp Leu Arg Arg His Met Leu Thr His Thr Lys Glu Lys Pro Phe Ala
                1090                1095                1100
        Cys His Leu Cys Gly Gln Arg Phe Asn Arg Asn Gly His Leu Lys Phe
        1105                1110                1115                1120
        His Ile Gln Arg Leu His Ser Pro Asp Gly Arg Lys Ser Gly Thr Pro
                        1125                1130                1135
```

-continued

```
Thr Ala Arg Ala Pro Thr Gln Thr Pro Thr Gln Thr Ile Ile Leu Asn
            1140            1145             1150

Ser Asp Asp Glu Thr Leu Ala Thr Leu His Thr Ala Leu Gln Ser Ser
        1155             1160             1165

His Gly Val Leu Gly Pro Glu Arg Leu Gln Gln Ala Leu Ser Gln Glu
    1170             1175             1180

His Ile Ile Val Ala Gln Glu Gln Thr Val Thr Asn Gln Glu Glu Ala
1185             1190             1195             1200

Ala Tyr Ile Gln Glu Ile Thr Thr Ala Asp Gly Gln Thr Val Gln His
            1205             1210             1215

Leu Val Thr Ser Asp Asn Gln Val Gln Tyr Ile Ile Ser Gln Asp Gly
            1220             1225             1230

Val Gln His Leu Leu Pro Gln Glu Tyr Val Val Val Pro Gly His
        1235             1240             1245

His Ile Gln Val Gln Glu Gly Gln Ile Thr His Ile Gln Tyr Glu Gln
    1250             1255             1260

Gly Ala Pro Phe Leu Gln Glu Ser Gln Ile Gln Tyr Val Pro Val Ser
1265             1270             1275             1280

Pro Gly Gln Gln Leu Val Thr Gln Ala Gln Leu Glu Ala Ala His
            1285             1290             1295

Ser Ala Val Thr Ala Val Ala Asp Ala Ala Met Ala Gln Ala Gln Gly
            1300             1305             1310

Leu Phe Gly Thr Asp Glu Thr Val Pro Glu His Ile Gln Gln Leu Gln His Gln
        1315             1320             1325             1330

Gly Ile Glu Tyr Asp Val Ile Thr Leu Ala Asp Asp
        1335             1340
```

The NIF-1 protein sequence (SEQ ID NO: 3) and its functional domains are shown in FIG. 1A, beginning with the Met initiator, designated by the arrowhead. NIF-1 contains 1342 amino acids consisting of six predicted C2H2 type zinc-fingers, an LxxLL motif, a putative leucine-zipper region near its C-terminus, and a region of ~35 amino acids rich in acidic amino acids towards the N-terminus.

The nucleotide region 5' to the start codon of the protein (seen in FIG. 1A) is not required for expression of the translated protein, therefore, another suitable form of the nucleic acid of the present invention is a nucleic acid molecule having a nucleotide sequence of SEQ ID NO: 4 as follows:

```
atggaggaga acgaggtgga gagcagcagc gacgcggccc ctgggcctgg ccggcccgag    60
gagccctctg agagcggcct gggtgtgggc acctcagaag ccgtgtccgc cgacagcagc   120
gacgccgcgg ccgccccggg gcaggcagag gccgatgact ctggcgtggg gcaaagctcg   180
gaccgcggca gccgttctca ggaggaggta tctgagagca gctcgagcgc agaccccctg   240
cctaatagct acctccctga ttcatcgtct gtgtctcatg ggccagtggc aggggtgaca   300
ggcggtcccc cagcacttgt gcactctagt gcactcccag accccaacat gctggtgtcc   360
gactgcacag cttcctcctc ggacctgggc tcggccatcg acaagatcat cgagtccacc   420
atcgggcccg acctcatcca gaactgcatc actgtgacca gtgctgagga tggcggggcc   480
gagaccacac ggtacctgat cctacagggc ccagatgatg agcccccat gacatcacca   540
atgtccagtt ccaccttggc ccacagccta gcagccattg aggccctggc agatggcccc   600
acatccacat ccacatgcct ggaggcacag ggtgggccca gctccccggt gcagctgccc   660
ccagcctccg gtgccgaaga gccggacctg cagagcctgg aggccatgat ggaggtggtg   720
gtggtgcagc agttcaaatg caagatgtgc cagtaccgga gcagcaccaa ggccacactg   780
ctgcgccaca tgcgggaacg ccacttccgt ccagtagcag cagccgcagc agcagctggt   840
```

-continued

```
aaaaaaggac gtctacggaa gtggagcacc tccaccaaga gccaagagga agagggacca    900
gaggaggagg acgatgatga cattgtagac gctggagcca ttgatgacct ggaggaggat    960
agcgactata atccagctga ggatgagccc cgaggccggc agcttcggct ccagcgcccc   1020 accccccagta ccccaaggcc ccgaaggaga cctggccggc cccggaagct gccccgcctg   1080
gagatctcag acctcccaga tggtgtggaa ggagagcctc tagtgagttc ccagagtgga   1140
cagagccctc cagagccaca ggatcccgag gctcccagct cctcaggccc aggacacctg   1200
gtggccatgg gcaaggtgag caggacccct gtggaagctg gtgtgagcca gtcagatgca   1260
gagaacgcag cccctcctg cccggatgag catgacactc tgccccggcg ccgaggtcga   1320
ccttccaggc gcttcctagg caagaaatac cgcaagtact attacaagtc gcccaaacca   1380
cttttgaggc ccttcctgtg ccgcatctgt ggttctcgct ttctgtccca cgaggacctg   1440
cgcttccacg tcaactccca tgaggctggc gatccccagc tcttcaagtg cctgcagtgc   1500
agctatcgtt cccgccgctg gtcctcgctc aaggagcaca tgttcaacca cgtgggcagc   1560
aagccctaca agtgtgacga gtgcagctac accagtgtct accggaagga cgtcattcgg   1620
cacgccgctg tgcacagccg ggaccggaag aagaggccag atccgactcc aaagctgagc   1680
tctttcccct gccctgtgtg tggccgtgtg taccccatgc agaaaagact cacgcagcac   1740
atgaagacgc acagcactga gaagcccac atgtgtgaca agtgtggaaa gtcctttaag   1800
aagcgctaca ccttcaaaat gcacctgctc acgcacatcc aggctgttgc caaccgcagg   1860
ttcaagtgtg agttctgtga gtttgtttgt gaagacaaga aggcactgct gaaccaccag   1920
ttgtcccacg tcagtgacaa gcccttcaaa tgcagctttt gtccctaccg cacccttccga  1980 gaggacttct tgctgtccca tgtggctgtc aagcacacag gggccaagcc cttcgcctgt   2040
gagtactgcc acttcagcac acggcacaag aagaacctgc gcctgcacgt acggtgccga   2100
cacgcaagca gcttcgagga atgggggagg cgccaccctg aggagccccc ctcccgccgt   2160
cgccccttct tctctctgca gcagattgag gagctgaagc agcagcacag tgcggccccc   2220
ggaccacctc ccagttcccc aggacctcct gagataccc cagaggcgac aactttccag   2280
tcatctgagg ctccctcatt gctctgttct gacaccctgg gcggcgccac catcatctac   2340
cagcaaggag ctgaggagtc gacagcgatg gccacgcaga cagccttgga tcttctgctg   2400
aacatgagtg ctcagcggga actgggggc acagccctgc aggtggctgt ggtgaagtcg   2460
gaagatgtgg aagcagggtt agcatcccct ggtgggcagc cctcccctga aggtgccact   2520
ccacaggtgg tcaccctcca cgtggcagag ccagggggcg gtgcagcagc cgagagccag   2580
ctaggccctc ctgacctacc gcagatcacc ctggcacctg gtccatttgg tgggactggc   2640
tacagtgtca tcacagcacc ccctatggag gagggaacat cagctcctgg cacaccttac   2700
agcgaggagc ccgcaggaga ggcagcccag gctgtggttg tgagtgacac cctaaaagaa   2760
gctggcaccc actacatcat ggctactgat ggtacccagt tgcaccacat tgagctcacc   2820
gcagatggct ccatctcctt cccaagtcca gatgctctgg cctctggtgc caaatggccc   2880
ctgctgcagt gtgggggact gcccagagac ggccctgagc cccatctcc agccaagacc   2940 cactgcgtag gggactccca gagctctgcc tcctcacctc ctgcaaccag caaagccctg   3000
ggcctggcag tgccccgtc accgccatct gcagccactg ctgcatcaaa gaagttttcc   3060
tgcaagatct gtgccgaggc cttccctggc cgagctgaga tggagagtca caagcgggcc   3120
cacgctgggc ctggtgcctt caagtgcccc gactgcccct tcagtgcccg ccagtggccc   3180
gaggtccggg cgcacatggc acagcactca agcctacggg cccaccagtg tagccagtgc   3240
```

-continued

```
agctttgcct ccaagaacaa gaaggacctg cgtcggcaca tgctgactca cacaaaggag   3300
aagccttttg catgccacct ctgcgggcag cgtttcaacc gtaacgggca cctcaagttc   3360
cacatccagc ggctgcacag tcctgatggg aggaagtcag gaaccccctac agcccgggcc  3420 cctacccaga ccccaaccca gaccatcatc ctgaacagtg atgacgaaac actggccacc   3480
ctgcacactg cactccagtc cagtcacggg gtcctgggcc cagagcggct acagcaggca   3540
ctgagccagg aacacatcat cgttgcccag gaacagacag tgaccaatca ggaggaagcc   3600
gcctacatcc aagagatcac cacggcagat ggccagaccg tacagcacct ggtgacctcc   3660
gacaaccagg tgcagtatat catctcccag gatggtgtcc agcacctgct cccccaggaa   3720
tatgttgtgg tccctgaagg ccatcacatc caggtacagg agggccagat cacacacatc   3780
cagtatgaac aaggagcccc gttccttcag gagtcccaga tccagtatgt gcctgtgtcc   3840
ccaggccagc agcttgtcac acaggctcaa cttgaggctg cagcacactc agctgtcaca   3900
gcagtggctg atgctgccat ggcccaagcc cagggcctgt ttggtacaga cgagacagtg   3960
cccgaacaca ttcaacagct gcagcaccag ggcatcgagt acgacgtcat caccctggcc   4020
gatgactgag ccccgagggc ccaacacaga tcatggattt gcggccagct ctcctggggg   4080
taggggccca ccaggactca cctccctctt catttaggat ctccagatac tggatagcca   4140
gcatcctctc attcccaggg agccagacct gtgctgttgg ggttaggggc agccatgggc   4200
cccagccagg acatgctggg tgccccagcc tgcaggcagg cttttgggaga gaaatttatt  4260 tttgtttggg tggacccact ggcctgtcag tctcaataaa gggaccggag tccagtcctg   4320
aacagcttaa aaaaaaaa                                                  4339
```

Also suitable as a nucleic acid molecule of the present invention is the isolated human nucleic acid molecule having a nucleotide sequence of SEQ ID NO: 5, as follows:

```
atggaggaga acgaggtgga gagcagcagc gacgcggccc ctgggcctgg ccggcccgag    60
gagccctctg agagcggcct gggtgtgggc acctcagaag ccgtgtccgc cgacagcagc   120
gacgccgcgg ccgccccggg gcaggcagag gccgatgact ctggcgtggg gcaaagctcg   180
gaccgcggca gccgttctca ggaggaggta tctgagagca gctcgagcgc agacccctg   240 cctaatagct acctccctga ttcatcgtct gtgtctcatg gccagtggc agggtgaca    300 ggcggtcccc cagcacttgt gcactctagt gcactcccag accccaacat gctggtgtcc   360
gactgcacag cttcctcctc ggacctgggc tcggccatcg acaagatcat cgagtccacc   420
atcgggcccg acctcatcca gaactgcatc actgtgacca gtgctgagga tggcgggggcc  480 gagaccacac ggtacctgat cctacagggc ccagatgatg gagcccccat gacatcacca   540
atgtccagtt cccccagttc cccaggacct cctgagatac cccagaggc gacaactttc   600 cagtcatctg aggctccctc attgctctgt tctgacaccc tgggcggcgc caccatcatc   660
taccagcaag gagctgagga gtcgacagcg atggccacgc agacagcctt ggatcttctg   720
ctgaacatga gtgctcagcg ggaactgggg ggcacagccc tgcaggtggc tgtggtgaag   780
tcggaagatg tggaagcagg gttagcatcc cctggtgggc agccctcccc tgaaggtgcc   840
actccacagg tggtcaccct ccacgtggca gagccagggg gcggtgcagc agccgagagc   900
cagctaggcc ctcctgacct accgcagatc accctggcac ctggtccatt tggtgggact   960
ggctacagtg tcatcacagc acccccctatg gaggagggaa catcagctcc tggcacacct  1020
```

-continued

```
tacagcgagg agcccgcagg agaggcagcc caggctgtgg ttgtgagtga caccctaaaa   1080
gaagctggca cccactacat catggctact gatggtaccc agttgcacca cattgagctc   1140
accgcagatg gctccatctc cttcccaagt ccagatgctc tggcctctgg tgccaaatgg   1200
cccctgctgc agtgtggggg actgcccaga gacggccctg agcccccatc tccagccaag   1260
acccactgcg taggggactc ccagagctct gcctcctcac ctcctgcaac cagcaaagcc   1320
ctgggcctgg cagtgccccc gtcaccgcca tctgcagcca ctgctgcatc aaagaagttt   1380
tcctgcaaga tctgtgccga ggccttccct ggccgagctg agatggagag tcacaagcgg   1440
gcccacgctg ggcctggtgc cttcaagtgc cccgactgcc ccttcagtgc ccgccagtgg   1500
cccgaggtcc gggcgcacat ggcacagcac tcaagcctac ggccccacca gtgtagccag   1560
tgcagctttg cctccaagaa caagaaggac ctgcgtcggc acatgctgac tcacacaaag   1620
gagaagcctt ttgcatgcca cctctgcggg cagcgtttca accgtaacgg gcacctcaag   1680
ttccacatcc agcggctgca cagtcctgat gggaggaagt caggaacccc tacagcccgg   1740
gcccctaccc agaccccaac ccagaccatc atcctgaaca gtgatgacga aacactggcc   1800
accctgcaca ctgcactcca gtccagtcac ggggtcctgg gccagagcg gctacagcag   1860
gcactgagcc aggaacacat catcgttgcc caggaacaga cagtgaccaa tcaggaggaa   1920
gccgcctaca tccaagagat caccacggca gatggccaga ccgtacagca cctggtgacc   1980
tccgacaacc aggtgcagta tatcatctcc caggatggtg tccagcacct gctcccccag   2040
gaatatgttg tggtccctga aggccatcac atccaggtac aggagggcca gatcacacac   2100
atccagtatg aacaaggagc cccgttcctt caggagtccc agatccagta tgtgcctgtg   2160
tccccaggcc agcagcttgt cacacaggct caacttgagg ctgcagcaca ctcagctgtc   2220
acagcagtgg ctgatgctgc catggcccaa gcccagggcc tgtttggtac agacgagaca   2280
gtgcccgaac acattcaaca gctgcagcac cagggcatcg agtacgacgt catcaccctg   2340
gccgatgact gagccccgag ggcccaacac agatcatgga tttgcggcca gctctcctgg   2400
gggtagggg ccaccaggac tcacctccct cttcatttag gatctccaga tactggatag   2460
ccagcatcct ctcattccca gggagccaga cctgtgctgt tggggttagg ggcagccatg   2520
ggccccagcc aggacatgct gggtgcccca gcctgcaggc aggctttggg agagaaattt   2580
atttttgttt gggtggaccc actggcctgt cagtctcaat aaagggaccg gagtccagtc   2640
ctgaacagct taaaaaaaaa aa                                             2662
```

SEQ ID NO: 5, referred to herein as NIF-2, encodes a full length alternatively spliced form of NIF-1 that is referred to herein as NIF-2. NIF-2 has an amino acid sequence of SEQ ID NO: 6 as follows:

```
Met Glu Glu Asn Glu Val Glu Ser Ser Ser Asp Ala Ala Pro Gly Pro
 1               5                  10                  15

Gly Arg Pro Glu Glu Pro Ser Glu Ser Gly Leu Gly Val Gly Thr Ser
                20                  25                  30

Glu Ala Val Ser Ala Asp Ser Ser Asp Ala Ala Ala Pro Gly Gln
        35                  40                  45

Ala Glu Ala Asp Asp Ser Gly Val Gly Gln Ser Asp Arg Gly Ser
    50                  55                  60

Arg Ser Gln Glu Glu Val Ser Glu Ser Ser Ser Ala Asp Pro Leu
65                  70                  75                  80
```

-continued

```
Pro Asn Ser Tyr Leu Pro Asp Ser Ser Ser Val Ser His Gly Pro Val
                 85                  90                  95
Ala Gly Val Thr Gly Pro Pro Ala Leu Val His Ser Ser Ala Leu
            100                 105                 110
Pro Asp Pro Asn Met Leu Val Ser Asp Cys Thr Ala Ser Ser Ser Asp
            115                 120                 125
Leu Gly Ser Ala Ile Asp Lys Ile Ile Glu Ser Thr Ile Gly Pro Asp
    130                 135                 140
Leu Ile Gln Asn Cys Ile Thr Val Thr Ser Ala Glu Asp Gly Gly Ala
145                 150                 155                 160
Glu Thr Thr Arg Tyr Leu Ile Leu Gln Gly Pro Asp Asp Gly Ala Pro
                165                 170                 175
Met Thr Ser Pro Met Ser Ser Ser Pro Ser Ser Pro Gly Pro Pro Glu
            180                 185                 190
Ile Pro Pro Glu Ala Thr Thr Phe Gln Ser Ser Glu Ala Pro Ser Leu
        195                 200                 205
Leu Cys Ser Asp Thr Leu Gly Gly Ala Thr Ile Ile Tyr Gln Gln Gly
    210                 215                 220
Ala Glu Glu Ser Thr Ala Met Ala Thr Gln Thr Ala Leu Asp Leu Leu
225                 230                 235                 240
Leu Asn Met Ser Ala Gln Arg Glu Leu Gly Gly Thr Ala Leu Gln Val
                245                 250                 255
Ala Val Val Lys Ser Glu Asp Val Glu Ala Gly Leu Ala Ser Pro Gly
            260                 265                 270
Gly Gln Pro Ser Pro Glu Gly Ala Thr Pro Gln Val Val Thr Leu His
        275                 280                 285
Val Ala Glu Pro Gly Gly Gly Ala Ala Ala Glu Ser Gln Leu Gly Pro
    290                 295                 300
Pro Asp Leu Pro Gln Ile Thr Leu Ala Pro Gly Pro Phe Gly Gly Thr
305                 310                 315                 320
Gly Tyr Ser Val Ile Thr Ala Pro Pro Met Glu Glu Gly Thr Ser Ala
                325                 330                 335
Pro Gly Thr Pro Tyr Ser Glu Glu Pro Ala Gly Glu Ala Ala Gln Ala
            340                 345                 350
Val Val Val Ser Asp Thr Leu Lys Glu Ala Gly Thr His Tyr Ile Met
        355                 360                 365
Ala Thr Asp Gly Thr Gln Leu His His Ile Glu Leu Thr Ala Asp Gly
    370                 375                 380
Ser Ile Ser Phe Pro Ser Pro Asp Ala Leu Ala Ser Gly Ala Lys Trp
385                 390                 395                 400
Pro Leu Leu Gln Cys Gly Gly Leu Pro Arg Asp Gly Pro Glu Pro Pro
                405                 410                 415
Ser Pro Ala Lys Thr His Cys Val Gly Asp Ser Gln Ser Ser Ala Ser
            420                 425                 430
Ser Pro Pro Ala Thr Ser Lys Ala Leu Gly Leu Ala Val Pro Pro Ser
        435                 440                 445
Pro Pro Ser Ala Ala Thr Ala Ala Ser Lys Lys Phe Ser Cys Lys Ile
    450                 455                 460
Cys Ala Glu Ala Phe Pro Gly Arg Ala Glu Met Glu Ser His Lys Arg
465                 470                 475                 480
Ala His Ala Gly Pro Gly Ala Phe Lys Cys Pro Asp Cys Pro Phe Ser
                485                 490                 495
Ala Arg Gln Trp Pro Glu Val Arg Ala His Met Ala Gln His Ser Ser
            500                 505                 510
```

```
Leu Arg Pro His Gln Cys Ser Gln Cys Ser Phe Ala Ser Lys Asn Lys
        515                 520                 525
Lys Asp Leu Arg Arg His Met Leu Thr His Thr Lys Glu Lys Pro Phe
        530                 535                 540
Ala Cys His Leu Cys Gly Gln Arg Phe Asn Arg Asn Gly His Leu Lys
545                 550                 555                 560
Phe His Ile Gln Arg Leu His Ser Pro Asp Gly Arg Lys Ser Gly Thr
                565                 570                 575
Pro Thr Ala Arg Ala Pro Thr Gln Thr Pro Thr Gln Thr Ile Ile Leu
            580                 585                 590
Asn Ser Asp Asp Glu Thr Leu Ala Thr Leu His Thr Ala Leu Gln Ser
        595                 600                 605
Ser His Gly Val Leu Gly Pro Glu Arg Leu Gln Gln Ala Leu Ser Gln
    610                 615                 620
Glu His Ile Ile Val Ala Gln Glu Gln Thr Val Thr Asn Gln Glu Glu
625                 630                 635                 640
Ala Ala Tyr Ile Gln Glu Ile Thr Thr Ala Asp Gly Gln Thr Val Gln
                645                 650                 655
His Leu Val Thr Ser Asp Asn Gln Val Gln Tyr Ile Ile Ser Gln Asp
            660                 665                 670
Gly Val Gln His Leu Leu Pro Gln Glu Tyr Val Val Val Pro Glu Gly
        675                 680                 685
His His Ile Gln Val Gln Glu Gly Gln Ile Thr His Ile Gln Tyr Glu
    690                 695                 700
Gln Gly Ala Pro Phe Leu Gln Glu Ser Gln Ile Gln Tyr Val Pro Val
705                 710                 715                 720
Ser Pro Gly Gln Gln Leu Val Thr Gln Ala Gln Leu Glu Ala Ala Ala
                725                 730                 735
His Ser Ala Val Thr Ala Val Ala Asp Ala Ala Met Ala Gln Ala Gln
            740                 745                 750
Gly Leu Phe Gly Thr Asp Glu Thr Val Pro Glu His Ile Gln Gln Leu
        755                 760                 765
Gln His Gln Gly Ile Glu Tyr Asp Val Ile Thr Leu Ala Asp Asp
    770                 775                 780
```

NIF-2 differs from NIF-1 in lacking amino acids 185-743 of the NIF-1 protein sequence, designated by the arrows in FIG. 1A.

The present invention also relates to an isolated rat nucleic acid molecule encoding a protein or polypeptide that modulates transcriptional activation in a cell with or without collaboration with a nuclear hormone receptor transcriptional co-activator. One suitable form of this nucleic acid molecule has a nucleotide sequence of SEQ ID NO: 7, as follows:

```
atgttcaacc acgtgggcag caaaccctac aagtgtgacg aatgcagcta caccagtgtc    60
taccgcaagg atgttattcg gcatgcggcc gtgcacagcc aggaccgaaa gaagaggccg   120
gatccgaccc caaagctgag ctctttccct tgcccagtgt gtggccgtgt atacccatg    180
cagaagagac taacacagca catgaagact cacagtacgg agaagccaca catgtgcgat   240
aagtgtggaa agtcctttaa gaagcggtac accttcaaaa tgcacttgct cacacacatc   300
caggctgttg ccaaccgcag attcaagtgt gagttctgcg agtttgtttg tgaggacaag   360
aaagcactgt tgaaccacca gctgtcccat gttagcgaca agcccttcaa atgcagcttt   420
tgtccctatc gcaccttccg tgaggacttc ctgctgtctc atgtggctgt gaagcacaca   480
ggagccaagc ccttcgcctg tgagtactgc cacttcagca ctcgccacaa gaagaacctg   540
```

-continued

```
cgcctgcatg tacggtgccg acatgcgaac agctttgagg agtggggggcg gcgccaccct   600
gaggagcctc catcccgtcg ccgccccatc ttctctttgc aacagataga gaagctgaag   660
cagcagcaca gtgcggcccc tggccctccc ctcagttcag caggcccga ggccccccaa   720
gaaccagcac ctttccagtc acctgagact cccccactac tctgtcctga tgccctaggt   780
ggtgccacaa tcatctacca gcaaggcgct gaggagtcca ctgcaatggc cactcagaca   840
gccttggatc tactgttgaa catgagcgcc aacgagagc tggggccac agccttgcag   900
gtggctgtgg tgaagtcaga ggacgtggag gcagagttga catctactgc taggcagcct   960
tcctctgaag acaccactcc acgggtggtg acacttcatg tggcagagtc agggagcagt  1020
gtggcagctg agagccagct aggcccgtct gacctacagc agattgcctt gccacctggg  1080
ccattcagtg gggccagcta cagtgtcatc acagcacccc cgtggaggg gagggcatca  1140
gcttccggcc caccttacag ggaagaacct ccaggagagg cagcccaggc tgtggttgtg  1200
aacgacactc tcaaggaagc tggcacccac tatatcatgg cagctgatgg gacccagttg  1260
caccacattg agctgactgc agatggctcc atctccttcc caagcccaga tactctggcc  1320
cctggaacca agtggcccct gctgcagtgt ggagggccac ctagagatgg tcctgaggtt  1380
ctgtctccaa cgaagaccca ccatacggga ggctcccagg gctcttccac cccacccct  1440
gcaaccagcc atgccctagg cctgctagta ccccactccc caccgtctgc agcagcttca  1500
tcaacaaaga agttctcctg caaggtgtgc tcagaggcct tccctagccg tgcagagatg  1560
gagagtcaca agcgggccca tgctgggcct gctgccttca agtgccctga ctgcccttc   1620
agtgctcgcc aatggcccga ggtccgggct cacatggcac agcactccag tctgaggccc  1680
caccagtgca atcagtgtag cttcgcctcc aagaacaaga aggacctcag gcggcacatg  1740
ctgacacaca ccaatgagaa gccttttctca tgccacgtct gtgggcagcg tttcaacagg  1800
aacgggcacc tcaaattcca catccagcgg ctacatagca tcgatggtag aaagactggg  1860
acttctacag cccgagcccc agcccagacc atcatcctca atagtgaaga ggagacactg  1920
gccacactgc acactgcctt ccagtcgaat cacgggactc tggggacaga gaggctacag  1980
caggcactga gccaggagca tatcattgtg gcccaggaac agacagtggc caatcaggag  2040
gaagctacct acatccagga aatcacggca gatggccaga cggtacagca tctggtgacc  2100
tcagacaacc aggttcagta tatcatctct caggatggtg tccagcactt gctgcctcag  2160
gagtacgttg tggtccctga tggccatcac atccaggttc aggagggcca gatcacacac  2220
attcagtatg agcaaggcac cccattccta caggagtccc agatccagta tgtacctgta  2280
tcccccagcc agcagcttgt cacccaggct cagcttgaag ctgcagcaca ttctgctgtt  2340
acagtggctg atgctgccat ggcccaagcc cagggcctgt ttggcactga ggaggcagtg  2400
ccggaacaca ttcaacagct gcagcatcag ggcatcgagt acgacgtcat caccctctcg  2460
gatgactgag cctcaaaggc ccaacgctga tcgtggatat cggggccagc tctcctggag  2520
actagggact ttcctgtcct acttagggcc tccaganact ggacagttag tgtcccttga  2580
ctccaaagga gccagacctg tgctcttggg gggcagccaa gggctccagc caggacatgc  2640
tgggtgtgtc agcctgctgg caggctttgg gagagaaatt tattttgtt ttgatggacc  2700
cactggctcc tgtctcaata aagggaccag agtccagctc ttgccaaaaa aaaaaaaaa  2760
aaaaaaaaaa aaaaaaaa                                              2778
```

The present invention also relates to the rat NIF-1 protein or polypeptide encoded by SEQ ID NO: 7. This protein has an amino acid sequence of SEQ ID NO: 8, as follows:

```
Met Phe Asn His Val Gly Ser Lys Pro Tyr Lys Cys Asp Glu Cys Ser
 1               5                  10                  15

Tyr Thr Ser Val Tyr Arg Lys Asp Val Ile Arg His Ala Ala Val His
             20                  25                  30

Ser Gln Asp Arg Lys Lys Arg Pro Asp Pro Thr Pro Lys Leu Ser Ser
         35                  40                  45

Phe Pro Cys Pro Val Cys Gly Arg Val Tyr Pro Met Gln Lys Arg Leu
     50                  55                  60

Thr Gln His Met Lys Thr His Ser Thr Glu Lys Pro His Met Cys Asp
65                  70                  75                  80

Lys Cys Gly Lys Ser Phe Lys Lys Arg Tyr Thr Phe Lys Met His Leu
                 85                  90                  95

Leu Thr His Ile Gln Ala Val Ala Asn Arg Arg Phe Lys Cys Glu Phe
             100                 105                 110

Cys Glu Phe Val Cys Glu Asp Lys Lys Ala Leu Leu Asn His Gln Leu
         115                 120                 125

Ser His Val Ser Asp Lys Pro Phe Lys Cys Ser Phe Cys Pro Tyr Arg
     130                 135                 140

Thr Phe Arg Glu Asp Phe Leu Leu Ser His Val Ala Val Lys His Thr
145                 150                 155                 160

Gly Ala Lys Pro Phe Ala Cys Glu Tyr Cys His Phe Ser Thr Arg His
                 165                 170                 175

Lys Lys Asn Leu Arg Leu His Val Arg Cys Arg His Ala Asn Ser Phe
             180                 185                 190

Glu Glu Trp Gly Arg Arg His Pro Glu Glu Pro Pro Ser Arg Arg Arg
         195                 200                 205

Pro Ile Phe Ser Leu Gln Gln Ile Glu Lys Leu Lys Gln Gln His Ser
     210                 215                 220

Ala Ala Pro Gly Pro Pro Leu Ser Ser Ala Gly Pro Glu Ala Pro Gln
225                 230                 235                 240

Glu Pro Ala Pro Phe Gln Ser Pro Glu Thr Pro Pro Leu Leu Cys Pro
                 245                 250                 255

Asp Ala Leu Gly Gly Ala Thr Ile Ile Tyr Gln Gln Gly Ala Glu Glu
             260                 265                 270

Ser Thr Ala Met Ala Thr Gln Thr Ala Leu Asp Leu Leu Leu Asn Met
         275                 280                 285

Ser Ala Gln Arg Glu Leu Gly Ala Thr Ala Leu Gln Val Ala Val Val
     290                 295                 300

Lys Ser Glu Asp Val Glu Ala Glu Leu Thr Ser Thr Ala Arg Gln Pro
305                 310                 315                 320

Ser Ser Glu Asp Thr Thr Pro Arg Val Val Thr Leu His Val Ala Glu
                 325                 330                 335

Ser Gly Ser Ser Val Ala Ala Glu Ser Gln Leu Gly Pro Ser Asp Leu
             340                 345                 350

Gln Gln Ile Ala Leu Pro Pro Gly Pro Phe Ser Gly Ala Ser Tyr Ser
         355                 360                 365

Val Ile Thr Ala Pro Pro Val Glu Gly Arg Ala Ser Ala Ser Gly Pro
     370                 375                 380

Pro Tyr Arg Glu Glu Pro Pro Gly Glu Ala Ala Gln Ala Val Val Val
385                 390                 395                 400
```

```
                        -continued
Asn Asp Thr Leu Lys Glu Ala Gly Thr His Tyr Ile Met Ala Ala Asp
                405                 410                 415
Gly Thr Gln Leu His His Ile Glu Leu Thr Ala Asp Gly Ser Ile Ser
            420                 425                 430
Phe Pro Ser Pro Asp Thr Leu Ala Pro Gly Thr Lys Trp Pro Leu Leu
        435                 440                 445
Gln Cys Gly Gly Pro Pro Arg Asp Gly Pro Glu Val Leu Ser Pro Thr
    450                 455                 460
Lys Thr His His Thr Gly Gly Ser Gln Gly Ser Ser Thr Pro Pro Pro
465                 470                 475                 480
Ala Thr Ser His Ala Leu Gly Leu Leu Val Pro His Ser Pro Pro Ser
                485                 490                 495
Ala Ala Ala Ser Ser Thr Lys Lys Phe Ser Cys Lys Val Cys Ser Glu
            500                 505                 510
Ala Phe Pro Ser Arg Ala Glu Met Glu Ser His Lys Arg Ala His Ala
        515                 520                 525
Gly Pro Ala Ala Phe Lys Cys Pro Asp Cys Pro Phe Ser Ala Arg Gln
    530                 535                 540
Trp Pro Glu Val Arg Ala His Met Ala Gln His Ser Ser Leu Arg Pro
545                 550                 555                 560
His Gln Cys Asn Gln Cys Ser Phe Ala Ser Lys Asn Lys Lys Asp Leu
                565                 570                 575
Arg Arg His Met Leu Thr His Thr Asn Glu Lys Pro Phe Ser Cys His
            580                 585                 590
Val Cys Gly Gln Arg Phe Asn Arg Asn Gly His Leu Lys Phe His Ile
        595                 600                 605
Gln Arg Leu His Ser Ile Asp Gly Arg Lys Thr Gly Thr Ser Thr Ala
    610                 615                 620
Arg Ala Pro Ala Gln Thr Ile Ile Leu Asn Ser Glu Glu Thr Leu
625                 630                 635                 640
Ala Thr Leu His Thr Ala Phe Gln Ser Asn His Gly Thr Leu Gly Thr
                645                 650                 655
Glu Arg Leu Gln Gln Ala Leu Ser Gln Glu His Ile Ile Val Ala Gln
            660                 665                 670
Glu Gln Thr Val Ala Asn Gln Glu Glu Ala Thr Tyr Ile Gln Glu Ile
        675                 680                 685
Thr Ala Asp Gly Gln Thr Val Gln His Leu Val Thr Ser Asp Asn Gln
    690                 695                 700
Val Gln Tyr Ile Ile Ser Gln Asp Gly Val Gln His Leu Leu Pro Gln
705                 710                 715                 720
Glu Tyr Val Val Val Pro Asp Gly His His Ile Gln Val Gln Glu Gly
                725                 730                 735
Gln Ile Thr His Ile Gln Tyr Glu Gln Gly Thr Pro Phe Leu Gln Glu
            740                 745                 750
Ser Gln Ile Gln Tyr Val Pro Val Ser Pro Ser Gln Leu Val Thr
        755                 760                 765
Gln Ala Gln Leu Glu Ala Ala His Ser Ala Val Thr Val Ala Asp
    770                 775                 780
Ala Ala Met Ala Gln Ala Gln Gly Leu Phe Gly Thr Glu Glu Ala Val
785                 790                 795                 800
Pro Glu His Ile Gln Gln Leu Gln His Gln Gly Ile Glu Tyr Asp Val
                805                 810                 815
Ile Thr Leu Ser Asp Asp
            820
```

Also suitable as a nucleic acid molecule of the present invention is a nucleic acid molecule having a nucleotide sequence that is at least 85% similar to the nucleotide sequences of SEQ ID NOs: 1, 4 or 5 using an alignment program, for example, basic BLAST using default parameters analysis. Also suitable is a nucleic acid molecule which hybridizes to the nucleotide sequences of SEQ ID NOs: 1, 4, or 5 under stringency conditions characterized by a hybridization buffer of 5×SSC buffer at a temperature of 56° C. Another example of suitable high stringency conditions is 4-5×SSC/0.1% w/v SDS at 54° C. for 1-3 hours. Another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05×BLOTTO, and washing at 2×SSC, 0.1% SDS at 62° C. The skilled artisan is aware of various parameters which may be altered during hybridization and washing and which will either maintain or change the stringency conditions, including temperature, salt, the presence of organic solvents, the size (i.e., number of nucleotides) and the G-C content of the nucleic acids involved, as well as the hybridization assay employed. For the purposes of defining a suitable level of stringency, reference can conveniently be made to Sambrook et al., *Molecular Cloning: A Laboratory Manual*, Third Edition, Cold Spring Harbor: Cold Spring Harbor Laboratory Press, New York (2001); *Nucleic Acid Hybridization: A Practical Approach*, Hames and Higgins, Eds., Oxford:IRL Press (1988); and *Hybridization with cDNA Probes User Manual*, Clonetech Laboratories, CA (2000), which are hereby incorporated by reference in their entirety).

The proteins or polypeptides of the present invention are preferably produced in a substantially purified form (preferably at least about 80%, more preferably 90%, pure) by conventional techniques. Purified protein may be obtained by several methods. Typically, the proteins or polypeptides of the present invention are secreted into the growth medium of recombinant bacterium, such as *E. coli*. To isolate the desired protein, the bacterial host cell carrying a recombinant plasmid is propagated, homogenized, and the homogenate is centrifuged to remove bacterial debris. The supernatant is then subjected to sequential ammonium sulfate precipitation. The fraction containing the desired protein of the present invention is subjected to gel filtration in an appropriately sized dextran or polyacrylamide column to separate the proteins. If necessary, the protein fraction may be further purified by HPLC. Alternative methods may be used as suitable.

Mutations or variants of the above polypeptides or proteins are encompassed by the present invention.

Variants may be modified, for example, by the deletion or addition of amino acids that have minimal influence on the properties, secondary structure, and hydropathic nature of the desired polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Fragments of the above proteins are also encompassed by the present invention. Suitable fragments can be produced by several means. In the first, subclones of the gene encoding the desired protein of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the proteins of the present invention, fragments of the genes of the present invention may be synthesized by using the polymerase chain reaction (PCR) technique together with specific sets of primers chosen to represent particular portions of the protein. These then would be cloned into an appropriate vector for increased expression of an accessory peptide or protein.

Chemical synthesis can also be used to make suitable fragments. Such a synthesis is carried out using known amino acid sequences for the proteins of the present invention. These fragments can then be separated by conventional procedures (e.g., chromatography, SDS-PAGE) and used in the methods of the present invention.

Another aspect of the present invention is a nucleic acid construct having a NIF nucleic acid molecule of the present invention. The nucleic acid molecule encoding a NIF-1 or NIF-2 polypeptide or protein of the present invention can be introduced into an expression system or vector of choice using conventional recombinant technology. Generally, this involves inserting the nucleic acid molecule into an expression system to which the molecule is heterologous (i.e., not normally present). The heterologous nucleic acid molecule is inserted into the expression system or vector in proper sense (5'→3') orientation and correct reading frame. Alternatively, the nucleic acid may be inserted in the "antisense" orientation, i.e, in a 3'→5' prime direction. The vector contains the necessary elements for the transcription and translation of the inserted protein-coding sequences.

Antisense nucleic acids are DNA or RNA molecules or oligoribonucleotides or oligodeoxyribonucleotides that are derived from at least a portion of a specific mRNA molecule (Weintraub, *Scientific American* 262:40 (1990), which is hereby incorporated by reference in its entirety). In one aspect of the present invention the antisense nucleic acid molecule may be complementary to a particular mRNA sequence or a fragment thereof. In the cell, the antisense nucleic acids hybridize to a target nucleic acid. The specific hybridization of an antisense nucleic acid molecule with its target nucleic acid interferes with the normal function of the target nucleic acid. The functions of DNA to be interfered with include replication and transcription. The functions of RNA to be interfered with include all vital functions, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is the regulation of the protein expression. In the context of the present invention, "regulation" of expression means either an increase (up-regulation) or a decrease (down-regulation) in the expression of a nucleic acid encoding NIF-1 or NIF-2 (U.S. Pat. No. 6,204,374 to Sidransky; U.S. Pat. No. 6,335,194 to Bennett et al., which are hereby incorporated by reference in their entirety).

In any aspect of the present invention in which down-regulation of NIF-1 or NIF-2 expression is desired, the method may involve an RNA-based form of gene-silencing known as RNA-interference (RNAi). Numerous reports have been published on critical advances in the understanding of the biochemistry and genetics of both gene silencing and RNAi (Matzke et al., "RNA-Based Silencing Strategies in Plants," *Curr. Opin. Genet. Dev.* 11(2):221-227 (2001), which is hereby incorporated by reference in its entirety). In RNAi, the introduction of double stranded RNA (dsRNA, or iRNA, for interfering RNA) into animal or plant cells leads to the destruction of the endogenous, homologous mRNA, phenocopying a null mutant for that specific gene. In both post-transcriptional gene silencing and RNAi, the dsRNA is processed to short interfering molecules of 21-, 22-, or 23-nucleotide RNAs (siRNAs) by a putative RNAaseIII-like enzyme (Tuschl T., "RNA Interference and Small Interfering RNAs," Chembiochem 2: 239-245 (2001); Zamore et al., "RNAi: Double Stranded RNA Directs the ATP-Dependent Cleavage of mRNA at 21 to 23 Nucleotide Intervals," *Cell* 101, 25-3, (2000), which are hereby incorporated by reference in their entirety). The endogenously generated siRNAs mediate and direct the specific degradation of the target mRNA. In the case of RNAi, the cleavage site in the mRNA molecule targeted for degradation is located near the center of the region covered by the siRNA (Elbashir et al., "RNA Interference is Mediated by 21- and 22-Nucleotide RNAs," *Gene Dev.* 15(2):188-200 (2001), which is hereby incorporated by reference in its entirety). In one aspect, dsRNA for the nucleic acid molecules of the present invention can be generated by transcription in vivo. This involves modifying a nucleic acid molecule of the present invention for the production of dsRNA, inserting the modified nucleic acid molecule into a suitable expression vector having the appropriate 5' and 3' regulatory nucleotide sequences operably linked for transcription and translation, and introducing the expression vector having the modified nucleic acid molecule into a suitable host cell or subject. In another aspect of the present invention, complementary sense and antisense RNAs derived from a substantial portion of the coding region of a nucleic acid molecule of the present invention are synthesized in vitro. (Fire et al., "Specific Interference by Ingested dsRNA," *Nature* 391:806-811 (1998); Montgomery et al, "RNA as a Target of Double-Stranded RNA-Mediated Genetic Interference in Caenorhabditis elegans," *Proc. Natl Acad Sci USA* 95: 15502-15507; Tabara et al., "RNAi in C. elegans: Soaking in the Genome Sequence," *Science* 282:430-431 (1998), which are hereby incorporated by reference in their entirety). The resulting sense and antisense RNAs are annealed in an injection buffer, and dsRNA is administered to the subject using any method of administration described herein, infra.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* Third Edition, Cold Spring Harbor: Cold Spring Harbor Laboratory Press, New York (2001), which is hereby incorporated by reference in its entirety.

A variety of host-vector systems may be utilized to express the protein-encoding sequence of the present invention. Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology,* 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli,* its bacteriophages, or plasmids, promoters such as the T7 phage promoter, lac promoter, trp promoter, recA promoter, ribosomal RNA promoter, the PR and PL promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The nucleic acid molecule(s) of the present invention, a promoter molecule of choice, a suitable 3' regulatory region, and if desired, a reporter gene, are incorporated into a vector-expression system of choice to prepare the nucleic acid construct of present invention using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

Once the isolated nucleic acid molecule encoding the NIF-1 or NIF-2 protein or polypeptide has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The DNA sequences are cloned into the host cell using standard cloning procedures known in the art, as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety. Suitable hosts include, but are not limited to, bacteria, virus, yeast, mammalian cells, and the like.

Accordingly, another aspect of the present invention relates to a method of making a recombinant cell. Basically, this method is carried out by transforming a host cell with a nucleic acid construct of the present invention under conditions effective to yield transcription of the nucleic acid molecule in the host cell. Preferably, a nucleic acid construct containing the nucleic acid molecule(s) of the present invention is stably inserted into the genome of the recombinant host cell as a result of the transformation.

Transient expression in protoplasts allows quantitative studies of gene expression since the population of cells is very high (on the order of $10^6$). To deliver DNA inside protoplasts, several methodologies have been proposed, but the most common are electroporation (Neumann et al., "Gene Transfer into Mouse Lyoma Cells by Electroporation in High Electric Fields," *EMBO J.* 1: 841-45 (1982); Wong et al., "Electric Field Mediated Gene Transfer," *Biochem Biophys Res Commun* 30:107(2):584-7 (1982); Potter et al., "Enhancer-Dependent Expression of Human Kappa Immunoglobulin Genes Introduced into Mouse pre-B Lymphocytes by Electroporation," *Proc. Natl. Acad. Sci. USA* 81: 7161-65 (1984, which are hereby incorporated by reference in their entirety) and polyethylene glycol (PEG) mediated DNA uptake Sambrook et al., *Molecular Cloning: A Laboratory Manual*, Third Edition, Cold Spring Harbor: Cold Spring Harbor Laboratory Press, New York (2001), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene (Fraley et al., *Proc. Natl. Acad. Sci. USA*, 79:1859-63 (1982), which is hereby incorporated by reference in its entirety).

Stable transformants are preferable for the methods of the present invention, which can be achieved by using variations of the methods above as describe in Sambrook et al., *Molecular Cloning: A Laboratory Manual*, Third Edition, Cold Spring Harbor: Cold Spring Harbor Laboratory Press, New York (2001), which is hereby incorporated by reference in its entirety. Thereafter, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley et al., *Proc. Natl. Acad. Sci. USA* 80:4803-4807 (1983), which is hereby incorporated by reference), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression construct of the present invention, such as "reporter genes," which encode for enzymes providing for production of a compound identifiable. The most widely used reporter gene for gene fusion experiments has been uidA, a gene from *Escherichia coli* that encodes the β-glucuronidase protein, also known as GUS. Jefferson et al., "GUS Fusions: β Glucuronidase as a Sensitive and Versatile Gene Fusion Marker in Higher Plants," *EMBO J.* 6:3901-3907 (1987), which is hereby incorporated by reference. Similarly, enzymes providing for production of a compound identifiable by luminescence, such as luciferase, are useful. The selection marker employed will depend on the target species; for certain target species, different antibiotics or biosynthesis selection markers are preferred.

Cells and tissues selected by means of an inhibitory agent or other selection marker are then tested for the acquisition of the transgene, for example by Southern blot hybridization analysis, using a probe specific to the transgene(s) contained in the given cassette used for transformation (Sambrook et al., *Molecular Cloning: A Laboratory Manual,* Third Edition, Cold Spring Harbor: Cold Spring Harbor Laboratory Press, New York (2001), which is hereby incorporated by reference).

The present invention also relates to an isolated antibody or binding portion thereof raised against a NIF protein or polypeptide of the present invention. Such an antibody may be monoclonal or polyclonal. In addition, antibody fragments, half-antibodies, hybrid derivatives, and other molecular constructs may be utilized. These antibodies and binding portions recognize and bind to the human or rat NIF proteins of the present invention, respectively.

Antibodies of the present invention include those which are capable of binding to a protein or polypeptide of the present invention and inhibiting the activity of such a polypeptide or protein. The disclosed antibodies may be monoclonal or polyclonal. Monoclonal antibody production may be effected by techniques which are well-known in the art. *Monoclonal Antibodies—Production, Engineering and Clinical Applications,* Ritter et al., Eds. Cambridge University Press, Cambridge, UK (1995), which is hereby incorporated by reference in its entirety. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature,* 256:495 (1975), which is hereby incorporated by reference in its entirety.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. Milstein and Kohler, *Eur. J. Immunol.,* 6:511 (1976), which is hereby incorporated by reference in its entirety. This immortal cell line, which is preferably murine, but may also be derived from cells of other mammalian species, including, but not limited to, rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled approximately every two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow, et. al., Eds., *Antibodies: A Laboratory Manual,* Cold Springs Harbor Laboratory, New York (1988), which is hereby incorporated by reference in its entirety.

It is also possible to use the anti-idiotype technology to produce monoclonal antibodies that mimic an epitope. As used in this invention, "epitope" means any antigenic determinant on an antigen to which the paratope of an antibody binds. Epitopic determinants usually consist of chemically active surface groupings of molecules, such as amino acids or sugar side chains and usually have specific three dimensional structural characteristics, as well as specific charge characteristics. For example, an anti-idiotype monoclonal antibody made to a first monoclonal antibody will have a binding domain in the hypervariable region that is the image of the epitope bound by the first monoclonal antibody.

In addition to utilizing whole antibodies, methods of the present invention encompass use of binding portions of such antibodies. Such binding portions include Fab fragments, F(ab')2 fragments, and Fv fragments. These antibody fragments can be made by conventional procedures, such as proteolytic fragmentation procedures, as described in J. Goding, *Monoclonal Antibodies: Principles and Practice,* pp. 98-118 N.Y. Academic Press (1983), and Harlow et al., *Antibodies: A Laboratory Manual,* Cold Springs Harbor Laboratory, New York (1988), which are hereby incorporated by reference in their entirety, or other methods known in the art.

Another aspect of the present invention is a method of regulating cell proliferation. This method involves transfecting a cell with a suitable isolated nucleic acid molecule of the present invention under conditions effective to regulate cell proliferation. Preparation of a suitable nucleic acid molecule, nucleic acid constructs having such nucleic acid molecules and appropriate 5' and 3' regulatory regions for expression in a host, and transformation methods suitable for this aspect of the present invention are as described above. Suitable cells for this aspect include, without limitation, all mammalian cells, including human cells.

The present invention also relates to a method of regulating differentiation of a cell. This method involves transfecting a cell with an isolated nucleic acid molecule of the present invention under conditions effective to regulate differentiation of the cell. Preparation of a suitable nucleic acid molecule, nucleic acid constructs having such nucleic acid molecules and appropriate 5' and 3' regulatory regions for expression in a host, and transformation methods suitable for this aspect of the present invention are as described above. Suitable cells for this aspect include, without limitation, all mammalian cells, including human cells.

Yet another aspect of the present invention is a method of regulating development of a cell. This method involves transfecting a cell with an isolated nucleic acid molecule of the present invention under conditions effective to regulate development of the cell. Preparation of a suitable nucleic acid molecule, nucleic acid constructs having such nucleic acid molecules and appropriate 5' and 3' regulatory regions for expression in a host, and transformation methods suitable for this aspect of the present invention are as described above. Suitable cells for this aspect include, without limitation, all mammalian cells, including human cells.

The present invention also relates to a method of modulating activity of a transcriptional co-activator complex in a cell. This method involves transfecting a cell with an isolated nucleic acid molecule encoding a protein or polypeptide of the present invention as described above, under conditions effective to modulate activity of a transcriptional co-activator complex in the cell. Preparation of a suitable nucleic acid molecule, nucleic acid constructs having such nucleic acid molecules and appropriate 5' and 3' regulatory regions for expression in a host, and transformation methods suitable for this aspect of the present invention are as described above. Suitable cells for this aspect include, without limitation, all mammalian cells, including human cells.

The present invention also relates to another method of modulating activity of a transcriptional co-activator complex in a cell. This method involves transfecting a cell with an antisense nucleic acid molecule derived from a nucleic acid molecule of the present invention, under conditions effective to modulate activity of a transcriptional co-activator complex in the cell. Preparation of an antisense nucleic acid construct having such an antisense nucleic acid molecule and appropriate 5' and 3' regulatory regions for expression in a host, and transformation methods suitable for this aspect of the present invention are as described herein. Suitable cells for this aspect include, without limitation, mammalian cell, including human cells.

The present invention also relates to yet another method of modulating activity of a transcriptional co-activator complex in a cell. This method involves contacting a cell with an isolated protein or polypeptide of the present invention that modulates transcriptional activation in a cell with or without collaboration with a nuclear hormone receptor transcriptional co-activator, under conditions effective to modulate activity of a transcriptional co-activator complex in the cell. Suitable cells for contacting in this aspect of the present invention include, without limitation, any mammalian cell, including human. In all aspects of the present invention invention "contacting a cell" can be carried out as desired, including, but not limited to, contacting cells in culture with a protein or polypeptide of the present invention in a suitable growth medium. Alternatively, mice, rats or other mammals are injected with the protein or polypeptide of the present invention. As will be appreciated by those in the art, "contacting" conditions will be dictated by the choice of source sample, e.g., body fluid, tissue, isolated cells, and the method of detection to be used.

The present invention relates to yet another method of modulating activity of a transcriptional co-activator complex in a cell. This method involves contacting a cell with an antibody, or a binding portion thereof, raised against a protein or polypeptide that modulates transcriptional activation in a cell with or without collaboration with a nuclear hormone receptor transcriptional co-activator, under conditions effective to modulate activity of a transcriptional co-activator complex in the cell. "Contacting" is carried out as described above.

The present invention also relates to a method of regulating hormone receptor activity in a cell. This method involves contacting a cell with an isolated protein or polypeptide of the present invention under conditions effective to regulate hormone receptor activity in the cell. Suitable cells for contacting in this and all aspects involving regulating hormone receptors include, without limitation, any mammalian cell, including human. In this and all aspects of the present invention that involve regulation of hormone receptor activity, the method applies to any hormone receptors including, without limitation, an estrogen receptor, a progesterone receptor, a vitamin D receptor, a thyroid hormone receptor, a retinoic acid receptor, a retinoid X receptor, a glucocorticoid receptor, a peroxisome-proliferation activated receptor, a liver X receptor, a bile acid receptor and an orphan receptor. "Contacting" is carried out as described above.

The present invention also relates to another method of regulating hormone receptor activity in a cell. This method involves contacting a cell with an antibody, or a binding portion thereof, against a protein or polypeptide of the present invention under conditions effective to regulate hormone receptor activity in the cell. Suitable cells for contacting in this and all aspects involving regulating hormone receptors include, without limitation, any mammalian cell, including human. "Contacting" is carried out as described above.

The present invention also relates to another method of regulating hormone receptor activity in a cell. This method involves transfecting a cell with a nucleic acid molecule encoding a protein or polypeptide of the present invention under conditions effective to regulate hormone receptor activity in the cell. Preparation of a nucleic acid construct having such a nucleic acid molecule and appropriate 5' and 3' regulatory regions for expression in a host, and transformation methods suitable for this aspect of the present invention are as described above. Suitable cells for this aspect include, without limitation, all mammalian cells, including human cells.

Another aspect of the present invention is yet another method of regulating hormone receptor activity in a cell. This method involves transfecting a cell with an antisense nucleic acid molecule that is derived from an isolated human nucleic acid molecule of the present invention under conditions effective to regulate hormone receptor activity in the cell. Preparation of an antisense nucleic acid construct having such an antisense nucleic acid molecule and appropriate 5' and 3' regulatory regions for expression in a host, and transformation methods suitable for this aspect of the present invention are as described above. Suitable cells for this aspect include, without limitation, mammalian cell, including human cells. Suitable hormone receptors for this aspect are as described above.

The present invention also relates to a method of modulating activity of a transcription factor in a cell. This method involves transfecting a cell with a nucleic acid molecule encoding a protein or polypeptide of the present invention under conditions effective to modulate activity of transcription factor in the cell. Preparation of a nucleic acid construct having such a nucleic acid molecule and appropriate 5' and 3' regulatory regions for expression in a host, and transformation methods suitable for this aspect of the present invention are as described above. Suitable cells for this aspect include, without limitation, all mammalian cells, including human cells. In this and all aspects of the present invention which involve modulating activity of a transcription factor in a cell, suitable transcription factors include, without limitation, cFos, cjun, AP1, NF-κB, p53, and STATs.

The present invention also relates to another method of modulating activity of a transcription factor in a cell. This method involves transfecting a cell with an antisense nucleic acid molecule that is derived from a nucleic acid molecule of the present invention, under conditions effective to modulate activity of transcription factor in the cell. Preparation of an antisense nucleic acid construct having such an antisense nucleic acid molecule and appropriate 5' and 3' regulatory regions for expression in a host, and transformation methods suitable for this aspect of the present invention are as described above. Suitable cells for this aspect include, without limitation, all mammalian cells, including human cells. Suitable transcription factors for this aspect are as described above.

The present invention also relates to a method of modulating endocrine function in a subject. This method involves treating a subject with a nucleic acid molecule of the present invention encoding a protein or polypeptide of the present invention under conditions effective to modulate endocrine function. Preparation of a nucleic acid construct having such a nucleic acid molecule and appropriate 5' and 3' regulatory regions for expression in a host, and transformation methods suitable for this aspect of the present invention are as described above. Suitable subjects for this aspect include, without limitation, any mammal, including a human.

Another aspect of the present invention relates to another method of modulating endocrine function in a subject. This method involves treating a subject with an antisense nucleic acid molecule that is derived from a nucleic acid molecule of the present invention under conditions effective to modulate endocrine function. Preparation of an antisense nucleic acid construct having such an antisense nucleic acid molecule and appropriate 5' and 3' regulatory regions for expression in a host, and transformation methods suitable for this aspect of the present invention are as described above. Suitable subjects for this aspect include, without limitation, any mammal, including a human. Suitable hormone receptors for this aspect are as described above.

The present invention also relates to yet another method of modulating endocrine function in a subject. This method involves treating a subject with a protein or polypeptide of the present invention that modulates transcriptional activation in a cell with or without collaboration with a nuclear hormone receptor transcriptional co-activator under conditions effective to modulate endocrine function. Suitable subjects for this of the present invention include, without limitation, any mammal, including a human.

The present invention relates to yet another method of modulating endocrine function in a subject. This method involves treating a subject with an antibody, or a binding portion thereof, raised against a protein or polypeptide that modulates transcriptional activation in a cell with or without collaboration with a nuclear hormone receptor transcriptional co-activator, under conditions effective to modulate endocrine function. Suitable subjects for this aspect of the present invention include, without limitation, any mammal, including a human.

The present invention also relates to a method of treating diabetes. This method involves treating a subject having diabetes with a protein or polypeptide of the present invention under conditions effective to treat diabetes. Suitable subjects for this aspect of the present invention include, without limitation, any mammal, including a human.

The present invention relates to another method of treating diabetes. This method involves treating a subject having diabetes with an antibody, or binding portion thereof, prepared against a protein or polypeptide of the present invention under conditions effective to treat diabetes. Suitable subjects for this aspect of the present invention include, without limitation, any mammal, including a human.

The present invention also relates to a method of treating insulin resistance in a subject. This method involves treating a subject having insulin resistance with a protein or polypeptide of the present invention under conditions effective to treat insulin resistance. Suitable subjects for this aspect of the present invention include, without limitation, any mammal, including a human.

EXAMPLES

Example 1

Yeast Two-Hybrid cDNA Library from GH4C1 Cells

Poly A$^+$ RNA isolated from GH4C1 cells was used for the synthesis of cDNA using a Stratagene (LaJolla, Calif.) cDNA synthesis system. cDNA was size fractionated and ligated with EcoRI-XhoI digested pJG4-5 which conditionally expresses the cDNA as a fusion with the B42 activation domain in yeast (Gyuris et al., "Cdi1, A Human G1 and S Phase Protein Phosphatase that Associates with Cdk2," *Cell* 75:791-803 (1993), which is hereby incorporated by reference in its entirety). The construction of the cDNA library has earlier been described (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety).

Example 2

Yeast Two-Hybrid Screen

Figure 6A:
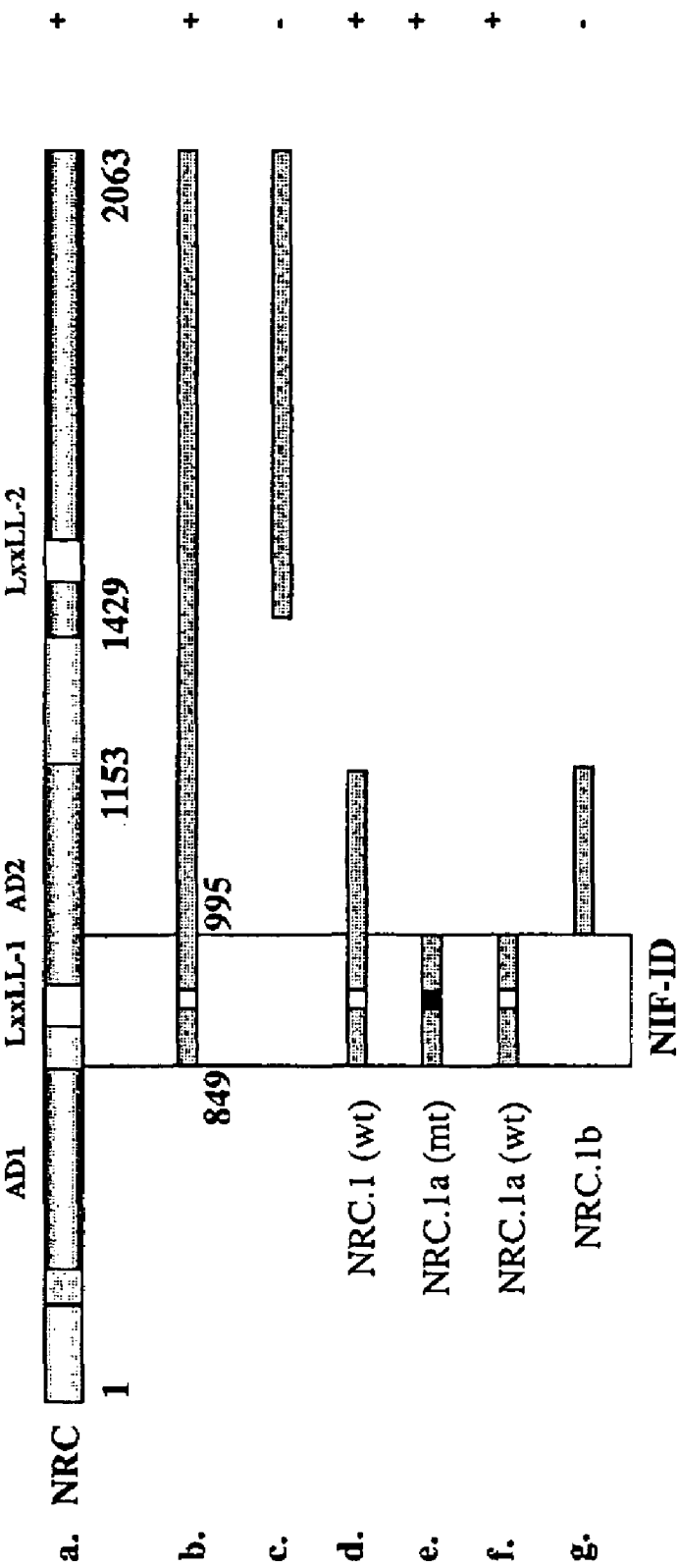
FIGS. 6A-B identify the NIF-1-Interaction Domain (NIF-ID) of NRC.

NRC-b (amino acids 849-2063), as shown in FIG. 6A, row "b," was cloned into pEG202ΔPL, a modified yeast LexA expression vector, and used as bait in a two-hybrid screen. pEG202ΔPL was derived from the parent vector, pEG202, as described earlier (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). All methods and transformation procedures have earlier been described (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). The yeast strain EGY48 harboring the LacZ reporter pSH18-34 (Gyuris et al., "Cdi1, A Human G1 and S Phase Protein Phosphatase that Associates with Cdk2," *Cell* 75:791-803 (1993), which is hereby incorporated by reference in its entirety), and pEG202ΔPL-NRC-b was transformed with the GH4C1 pJG4-5 cDNA library. Transformants were directly screened on X-gal SD-galactose-raffinose plates lacking trp, ura, his, and leu. Putative positive clones were further purified on trp$^-$, ura$^-$, his$^-$, and leu$^-$ SD-galactose-raffinose plates. The purified clones were plated on SD-dextrose/trp$^-$, ura$^-$' his$^-$ plates to repress the expression of cDNAs from pJG4-5. Galactose-inducible interactions were verified upon replica plating each clone on trp$^-$, ura$^-$, his$^-$, leu$^-$ X-gal SD-galactose-raffinose and trp$^-$, ura$^-$, his$^-$ X-gal SD-dextrose plates. Yeast clones exhibiting a positive LacZ response on galactose-raffinose and not on dextrose plates were considered to be potential NRC-interacting clones. The putative cDNAs from positive clones were further verified against several different baits. The positive interactors were then sequenced and subjected to restriction digestion, size determination, and further analysis.

Example 3

Preparation of Expression Plasmid Constructs

Expression plasmids for nuclear receptors and various reporters have been described earlier (Li et al., "NRIF3 is a Novel Coactivator Mediating Functional Specificity of Nuclear Hormone Receptors," *Mol. Cell. Biol.* 19:7191-7202 (1999); Mahajan et al., "A New Family of Nuclear Receptor Coregulators That Integrate Nuclear Receptor Signaling Through CREB-Binding Protein," *Mol. Cell. Biol.* 20:5048-5063 (2000), which are hereby incorporated by reference in their entirety). A Flag-tag sequence was introduced into the 5'-end of full length NIF-1 cDNA by PCR and cloned into a pEX vector (Li et al., "NRIF3 is a Novel Coactivator Mediating Functional Specificity of Nuclear Hormone Receptors," *Mol. Cell. Biol.* 19:7191-7202 (1999); Ito et al., "Identity Between TRAP and SMCC Complexes Indicates Novel Pathways for the Function of Nuclear Receptors and Diverse Mammalian Activators," *Mol. Cell* 3:361-370 (1999), which are hereby incorporated by reference in their entirety). Other than the Flag-tag, pEX-Flag-NIF-1 is identical to pEX-NIF-1. Gal4-LBD MOR (mouse ERα) was kindly provided by Malcom Parker (Mak et al., "Molecular Determinants of the Estrogen Receptor-Coactivator Interface," *Mol. Cell. Biol.* 19:3895-3903 (1999), which is hereby incorporated by reference in its entirety). All plasmids described below were generated by either PCR or restriction enzyme digestion and verified by sequencing and expression studies. Human pEX-NRC, various NRC fragments in pJG4-5ΔPL (B42 fusions), and pEG202ΔPL (LexA fusions) such as human NRC-c(1429-2063), NRC.1 wt. and mt. and human NRC(849-1153), analogous to the residues found in rat NRC. 1, have been previously described (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). B42 and LexA fusions of rat NRC.1a (849-995 wt. and mt.) and NRC.1b(995-1153) were amplified by PCR using specific primers and cloned into both pEG202ΔPL and/or pJG4-5ΔPL yeast vectors, sequenced and examined for protein expression. Rat NRC.1a was cloned as a GST fusion in pGEX4T (GST-NRC.1a). LexA-human ERa-LBD was produced by releasing the LBD from pJG4-5 and cloning into pEG202ΔPL.

Example 4

Cloning of Human NIF-1 and NIF-1 Expression Plasmids

Figure 5:
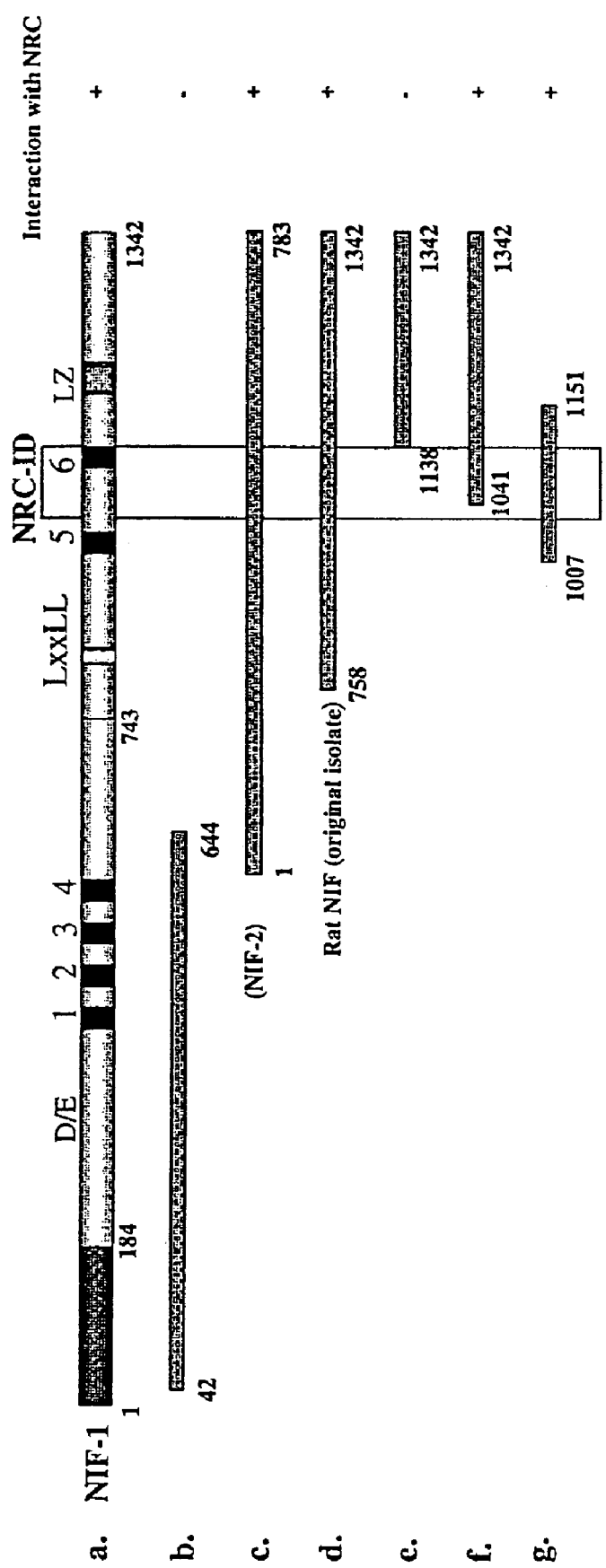
FIG. 5 shows the interaction of NIF-1 with NRC in yeast through a region containing zinc-finger 6.

Human NIF-1 was cloned by screening a λgt10 phage library derived from a human cell line, NTera-2D1. One of the positive phage clones (6B), containing a 4.5 kb cDNA insert, was identified as a near full-length NIF-1 lacking 110 bp from the 5' end. The 3' end of the 6B phage includes a stop codon and about 315 bp of 3' UTR sequence and a short poly A tail. Full-length NIF-1 was generated by ligating a 226 bp HindIII-XhoI PCR product of an EST (BE29723 1, see below) containing a consensus Kozak homology at the 5' end with an XhoI-EcoRI fragment of human NIF-1 (~4.5 kb) released from the 6B clone. The full-length NIF-1 cDNA was cloned into pEX (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety) and pcDNA3 vectors (Invitrogen, Carlsbad, Calif.) and contains coding sequences of 4029 bp with HindIII at the 5' end and EcoRI at the 3' end. GFP-NIF-1 was generated by releasing full-length NIF-1 cDNA from pEX-NIF-1 by HindIII-EcoRI and cloning into pEGFP(C3) (Clontech, Palo Alto, Calif.). Human NIF-1 (6B) was also cloned into the EcoRI site of pJG4-5ΔPL. One of the EST clones (BE297231) (IMAGE Consortium) was sequenced completely and identified as an isoform of human NIF-1 and was designated as NIF-2 (SEQ ID NO: 5). The NIF-2 cDNA lacking the first 222 nucleotides (N-terminal 74 amino acids) was released from pOTB7 with XhoI, end-filled and cloned into pJG4-5ΔPL and pEG202ΔPL yeast vectors at NcoI filled ends. The following plasmids were cloned in pJG4-5ΔPL and/or pEG202ΔPL yeast vectors, as shown in FIG. 5: 1) Human NIF-1 (FIG. 5, row "f"), the C-terminal region of human NIF-1 (representing amino acids 1043-1342) containing zinc-finger 6, the leucine zipper-like motif and the remainder of the C-terminus, was cloned into NcoI filled-XhoI sites; 2) human NIF-1, a SmaI-XhoI NIF-1 fragment representing amino acids 1138-1342 was ligated with NcoI filled-XhoI cut vectors (FIG. 5, row "e"); this clone contains the leucine-zipper like motif and remaining C-terminus of NIF-1; 3) human NIF-1, a NotI-EcoRI end filled fragment representing amino acids 42-644 of N-terminal region of NIF-1, was cloned into BamHI-end filled yeast vectors (FIG. 5, row "b"); 4) human NIF-1, representing amino acids 1007-1150, harboring zinc-fingers 5 and 6, was generated by PCR using specific primers and cloned as an XhoI-EcoRI fragment (FIG. 5, row "g").

Example 5

Mammalian Cells Transfection

Transfections in HeLa cells were performed with appropriate control vectors using calcium-phosphate co-precipitation as described earlier (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). Various ligands such as T3 for TR, 9-cis RA for RAR and RXR, and Dex for GR were used at 0.5 mM. TTNPB, which is selective for RAR, and LG100153, which is selective for RXR, were used at 200 nM unless otherwise indicated. Typically, 1 mg CAT reporter plasmid, 1-2 mg expression plasmids were used per sample unless otherwise indicated. All transfections were performed in duplicate or triplicate. The variation in CAT activity of the duplicate or triplicate samples was less than 10% and each experiment was repeated at least two times. All CAT assays were performed as described earlier (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). All transfections in GH4C1 cells were performed using the lipofectamine based reagent Geneporter 2 (GTS, San Diego Calif.) according to manufacturer's instructions. Reporter plasmids, −73 Collagenase CAT (Ways et al., "Dominant and Non-Dominant Negative c-erbAβ1 Receptors Associated with Thyroid Hormone Resistance Syndromes Augment TPA-Induction of the Collagenase Promoter and Exhibit Defective T3-Mediated Repression," *Mol. Endocrinol.* 7:1112-1120 (1993), which is hereby incorporated by reference in its entirety) and DMTV-IR-CAT (Forman et al., "Half-Site Spacing and Orientation Determines Whether Thyroid Hormone and Retinoic Acid Receptors and Related Factors Bind to DNA Response Elements as Monomers, Homodimers, or Heterodimers," *Mol. Endocrinol.* 6:429-442 (1992), which is hereby incorporated by reference in its entirety), were used at 50-100 ng/sample and other plasmids pEX-NRC, pEX-NIF-1 at 0.7-1.2 mg/sample. GFP-NIF-1 was transfected into COS 1 cells using calcium-phosphate co-precipitation. The cell distribution of GFP-NIF-1 was analyzed by fluorescent microscopy and Hoechst dye staining of the nucleus 48 h later.

Example 6

Yeast and β-Galactosidase Assays

All β-galactosidase assays were performed at least twice in duplicate or triplicate. Various ligands such as T3 for the TRs, 9-cis RA for RXR and RAR, and estradiol (E2) were used at 1 mM, while deoxycorticosterone for GR was used at 10 mM. Yeast colonies were first grown exponentially in ura$^-$, his$^-$, and trp$^-$ SD-dextrose medium, washed, diluted to the appropriate density, and incubated in ura$^-$, his$^-$ and trp$^-$ SD-galactose-raffinose medium followed by quantitation of β-galactosidase as described earlier (Li et al., "NRIF3 is a Novel Coactivator Mediating Functional Specificity of Nuclear Hormone Receptors," *Mol. Cell. Biol.* 19:7191-7202 (1999); Mahajan et al., "A New Family of Nuclear Receptor Coregulators That Integrate Nuclear Receptor Signaling Through CREB-Binding Protein," *Mol. Cell. Biol.* 20:5048-5063 (2000), which are hereby incorporated by reference in their entirety). β-galactosidase units are expressed as (O.D. 420 nm×1000)/(minutes of incubation× O.D. 600 nm of yeast suspension).

Example 7

In Vivo Association of NIF-1 With NRC

The mammalian GST expression vectors, pEBG (expressing GST) and pEBG-NRC (expressing a GST fusion of full length NRC), have been described earlier (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). pEX-FlagNIF-1 was co-transfected with pEBG or pEBG-NRC in 293T and whole cell extracts were prepared 36 h later as described (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). Proteins remaining bound to the expressed GST proteins were purified using glutathione-agarose beads and processed for SDS-gel electrophoresis followed by Western blotting as described earlier (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). The Western blot was probed with M2 anti-Flag antibody to detect FlagNIF-1.

Example 8

In Vitro Binding of NIF-1 to GST-NRC

GST-NRC.1a was expressed in SG1 1117 *E. coli* by induction with IPTG, purified, and immobilized to glutathione-agarose described previously (Hadzic et al., "A 10-Amino-Acid Sequence in the N-Terminal A/B Domain of Thyroid Hormone Receptor α is Essential for Transcriptional Activation and Interaction with the General Transcription Factor TFIIB," *Mol. Cell. Biol.* 15:4507-4517 (1995), Hadzic et al., "A Novel Multifunctional Motif in the N-Terminal A/B Domain of T3Rα Modulates DNA-Binding and Receptor Dimerization," *J. Biol. Chem.* 273:10270-10278 (1998), which are hereby incorporated by reference in their entirety). NIF-1 was labeled by in vitro transcription/translation with $^{35}$S-L-methionine using rabbit reticulocyte lysates. Typically, 200-400 ng of GST protein bound to glutathione-agarose was used per assay. $^{35}$S-labeled proteins were mixed with GST or GST-NRC.1a beads. The samples were incubated at 4° C. for 30 min in binding buffer (Tris-HCl 20 mM, pH 7.7 at 25° C., 2 mM MgCl$_2$, 100 mM NaCl, 1 mM DTT, 0.01% BSA, 0.5 mM PMSF, 0.25% NP40 and 0.25 mM zinc acetate). The samples were washed with the same incubation buffer and the bound $^{35}$S-labeled protein analyzed by SDS-gel electrophoresis followed by autoradiography.

Example 9

Identification of NIF-1, a Novel Zinc-Finger Protein that Interacts with the Nuclear Receptor Co-activator, NRC NRC interacts with CBP in vivo (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety) and binds to and enhances transcriptional activation by ligand-bound nuclear hormone receptors as well other factors such as NF-kB and cFos and cJun (Ko et al., "Thyroid Hormone Receptor-Binding Protein, an LXXLL Motif-Containing Protein, Functions as a General Coactivator," *Proc. Natl. Acad. Sci. USA* 97:6212-6217 (2000); Mahajan et al., "A New Family of Nuclear Receptor Coregulators That Integrate Nuclear Receptor Signaling Through CREB-Binding Protein," *Mol. Cell. Biol.* 20:5048-5063 (2000), which are hereby incorporated by reference in their entirety). Since the mechanism of transcriptional enhancement by NRC is not clearly understood, the identification of factors which may play a role in mediating these effects of NRC was sought. In this study, a yeast two-hybrid screen was used to identify factors that functionally interact with NRC. A yeast LexA vector that expresses a fusion of the LexA DBD with NRC (amino acids 849-2063) was used as bait to screen the pJG4-5 GH4C1 cDNA library that was used previously to identify NRC (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). pJG4-5 conditionally expresses cDNAs as a B42 activation domain fusion. This screen identified a cDNA interactor (1.8 kb) which was found to be an ortholog of a putative transcript from a gene of unknown function identified in the human genome located on chromosome 20. The assembled transcript from this human genome sequence is predicted to encode a protein of 1342 amino acids. This clone is referred to as NIF-1 for NRC Interacting Factor-1. RT-PCR with mRNA from human T-47D and MCF-7 breast cancer cells, using primers from the predicted human sequence, identified an mRNA of the same size as that assembled from the NIF-1 genomic sequence. In addition, RT-PCR with GH4C1 mRNA, using primers from the predicted human cDNA sequence, indicated that an mRNA of similar size to the assembled NIF-1 sequence is expressed in GH4C1 cells.

Example 10

Cloning, Sequence, and Predicted Domain Structure of NIF-1

A human teratocarcinoma λgt10 cDNA library was screened using a $^{32}$P-NIF-1 probe generated from MCF-7 cells by PCR. Seven independent NIF-1 cDNA clones were identified. Upon comparison with the predicted transcript from the human genomic NIF-1 sequence, the longest clone isolated from the phage library was missing 110 nucleotides of coding sequence from the 5' end, while the 3' end extended beyond the stop codon and contained a poly A tail and a 3' UTR sequence. A database search identified a number of ESTs of which 7 ESTs were sequenced completely. One of the ESTs (BE297231) was found to be a full length alternatively spliced form of NIF-1 that is referred to herein as NIF-2. The 5' end of this EST contained an authentic ATG and an inframe stop codon upstream of the ATG consistent with predicted NIF-1 mRNA sequence. A PCR product containing the 110 nucleotides missing in NIF-1 (6B) was generated from the EST DNA and ligated to NIF-1(6B) to generate a full-length NIF-1 clone. In addition to the human and rat NIFs, a GenBank search identified a NIF-related partial chicken cDNA clone (cFZF) (Accession No. U27196) of unknown function.

FIG. 1A compares the domain structure of the predicted amino acid sequence of NIF-1 with NIF-2 and the partial rat NIF cloned from GH4C1 cells with the yeast-two hybrid screen. NIF-1 contains 1342 amino acids consisting of six predicted C2H2 type zinc-fingers, an LxxLL motif, a putative leucine-zipper region near its C-terminus, and a region of ~35 amino acids rich in acidic amino acids towards the N-terminus. Motif searches also indicated several putative protein kinase A ("PKA") and tyrosine kinase phosphorylation sites. In addition, a motif search identified that the region containing the first three C2H2 zinc-fingers of NIF-1 are a component of the recently described BED finger DNA binding domain found in a number of transcriptional activators and repressors in Drosophila (Aravind, "The BED Finger, A Novel DNA-Binding Domain in Chromatin-Boundary-Element-Binding Proteins and Transposases," *Trends Biochem. Sci.* 25:421-423 (2000); Hart et al., "Evidence for an Antagonistic Relationship Between the Boundary Element-Associated Factor BEAF and the Transcription Factor DREF," *Chromosoma* 108:375-383 (1999), which are hereby incorporated by reference in their entirety). Although the function of these BED finger domains is not understood, it has been suggested that these proteins may alter local chromatin architecture through association with insulator sequences in the DNA (Aravind, "The BED Finger, A Novel DNA-Binding Domain in Chromatin-Boundary-Element-Binding Proteins and Transposases," *Trends Biochem. Sci.* 25:421-423 (2000), which is hereby incorporated by reference in its entirety).

The zinc-fingers, LxxLL, and putative leucine-zipper regions of human NIF-1, rat NIF, and the chicken NIF clone are highly conserved with some divergence of zinc-finger 5 and the leucine-zipper region. The LxxLL region is highly conserved in all three proteins, as shown in FIG. 1B. Overall, human NIF-1 and the partial rat NIF clone share 86% homology at the amino acid level while the chicken NIF clone exhibits less homology to NIF-1 (62%). The first 184 amino acids of NIF-1 are identical to that found in NIF-2. NIF-2 lacks the region of NIF-1 corresponding to amino acids 185 to 743 which harbors the DE region and zinc-fingers 1 through 4 but is otherwise identical to NIF-1. FIG. 1C illustrates the amino acid sequence and functional domains of human NIF-1. These sequences have been deposited in the GenBank (NIF-1/NIF-2, Accession No. AF395833; rat NIF, Accession Nos AF309071 and AY079168).

Example 11

Cell and Tissue Distribution of NIF-1

Figure 2:
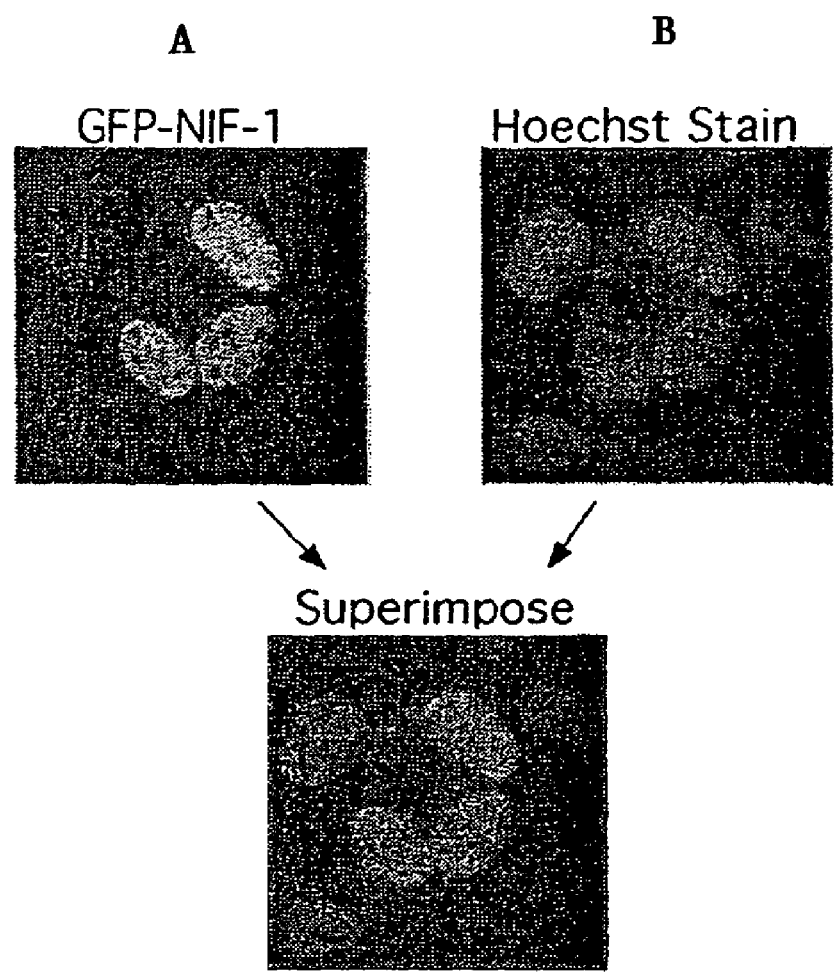
FIGS. 2A-C are fluorescent micrographs demonstrating that NIF-1 is a nuclear protein.
Figure 3:
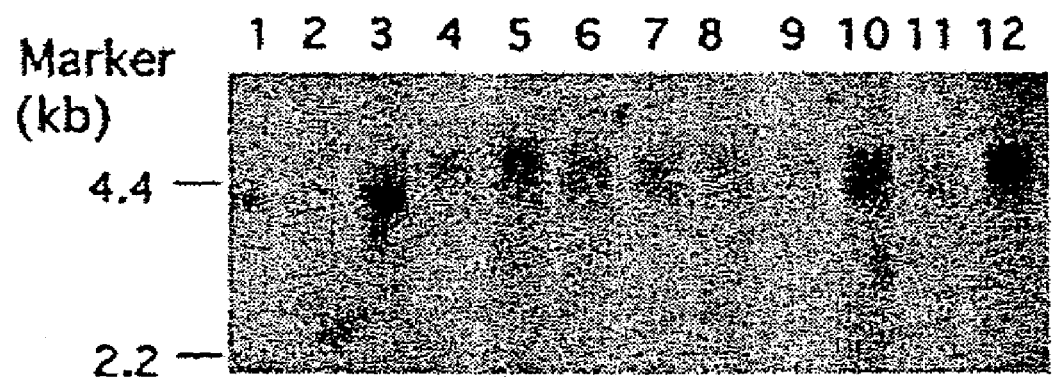
FIG. 3 is a Northern blot of NIF-1 mRNAs in different tissues. NIF-1 mRNAs were detected using an MTN blot (Stratagene, La Jolla, Calif.) containing poly A+RNAs from the various tissues indicated. A NIF-1 mRNA of ~5 kb was detected by probing the blot with $^{32}$P-labeled human NIF-1 cDNA. Lanes 1 through 12 contain RNAs from brain, heart, skeletal muscle, colon, thymus, spleen, kidney, liver, small intestine, placenta, lung, and blood, respectively. A shorter mRNA of ~2.5 kb designated as NIF-2 was detected upon longer exposure of the blot as described in Example 11.

To study the subcellular localization of NIF-1, COS1 cells were transfected with a pEGFP-NIF-1 expression vector and the cellular distribution of the GFP-NIF-1 was determined by fluorescent microscopy. As shown in FIG. 2A, GFP-NIF-1 localizes exclusively to the cell nucleus, consistent with its possible function as a transcriptional regulator. A full-length $^{32}$P-labeled NIF-1 cDNA probe, predicted to identify both NIF-1 and NIF-2 mRNAs, was used to study the tissue distribution of human NIFs, as shown in FIG. 3. A multi-tissue Northern blot (Stratagene, La Jolla, Calif.) was probed with the full-length $^{32}$P labeled NIF-1 cDNA probe. A NIF-1 mRNA of ~5 kb with relatively higher expression was detected in skeletal muscle, thymus, placenta, and blood. Colon, spleen, kidney, and lung showed moderate expression, while small intestine, heart, liver, and brain showed lower levels of expression of NIF-1 mRNA. Overexposure of the same blot detected an mRNA species of ~2.5 kb, consistent with the size of NIF-2. This transcript was detected in heart and skeletal muscle and, to a lesser extent, in thymus, spleen, kidney, liver, placenta, and blood. NIF-2 was not detected in small intestine and colon. The results of the Northern blot suggest that the NIF-1 mRNAs are of low abundance but are widely expressed.

Example 12

NRC Associates with NIF-1 in Mammalian Cells

Figure 4:
FIG. 4 is a Western blot showing that NIF-1 associates with NRC in mammalian cells. The mammalian GST (glutathione-S-transferase) expression vectors, pEBG (expressing GST) and pEBG-NRC (expressing a GST fusion of full length NRC) were co-transfected with pEX-FlagNIF-1 in 293T cells. Whole cell extracts were prepared 36 h later and the proteins remaining bound to the expressed GST proteins were purified using glutathione-agarose beads and processed for SDS-gel electrophoresis followed by Western blotting as described earlier (Mahajan et al., "A New Family of Nuclear Receptor Coregulators That Integrate Nuclear Receptor Signaling Through CREB-Binding Protein," Mol. Cell. Biol. 20:5048-5063 (2000)). The Western blot was probed with M2 anti-Flag antibody to detect FlagNIF-1. Lane 1, pEBG control (CON.), lane 2, pEBG-NRC.

To document that NIF-1 can associate with NRC in vivo, a vector expressing Flag-tagged NIF-1 was co-expressed with mammalian GST vectors expressing GST (PEBG) or GST-NRC (pEBG-NRC) in 293T cells. Thirty-six hr later, the cells were lysed and the lysates incubated with glutathione-agarose followed by SDS-gel electrophoresis and Western blotting with anti-Flag M2 antibody. The results are shown in FIG. 4. Flag-tagged NIF-1 was detected in cells expressing GST-NRC but not the GST control. These results indicate that NIF-1 can associate with NRC in mammalian cells.

Example 13

The C-terminal Region of NIF-1 Containing its Sixth Zinc-Finger Interacts with NRC Although the original NIF isolate from GH4C1 cells lacked the N-terminal region of human NIF-1, it shares amino acid identity with the corresponding region of human NIF-1, as shown in FIG. 1C, suggesting that the C-terminal region of NIF-1 is likely involved in the interaction of NIF-1 with NRC. To map the region(s) of NIF-1 which interact with NRC, various domains of NIF-1, shown in FIG. 5 as rows "b-g", were conditionally expressed in yeast as a B42-fusion from pJG4-5 and examined for interaction with a variety of LexA-NRC deletions, including the LxxLL-1 mutant of NRC which fails to bind nuclear hormone receptors (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). These studies indicated that the NRC interaction domain (NRC-ID) of NIF-1 maps to a 97 amino acid C-terminal region of NIF-1 containing zinc-finger six. A much weaker interaction (10- to 20-fold less) was also found with the N-terminal region of the protein. The precise region mediating this weaker interaction was not mapped but may be mediated by zinc-finger one which shares greater homology with zinc-finger six than any of the other zinc-finger motifs.

Example 14

Identification of the NIF-1 Interaction Domain (NIF-ID) of NRC

A yeast two-hybrid assay was also used to identify the region of NRC which interacts with NIF-1, as shown in FIG. 6A. Various regions of NRC were expressed as LexA fusions in yeast (designated as rows "a-g" in FIG. 6A) and their interaction compared with full-length NIF-1, NIF-2, and various deletions of NIF-1 conditionally expressed from pJG4-5. The NIF-ID of NRC was localized to amino acids 849 to 995 of human NRC which also contains the LxxLL-1 receptor interaction motif. To study the possible involvement or requirement of the NRC LxxLL-1 motif for direct interaction with NIF-1, yeast two hybrid assays were carried out with LexA-NRC constructs containing either the wild-type (LVNLL) (SEQ ID NO: 9) or mutated (AVNAA) (SEQ ID NO: 10) LxxLL-1 motif. The results indicate that LxxLL-1 is not required for interaction of NRC with NIFs since the LxxLL-1 mutant forms of NRC interacted with NIF-1 as efficiently as the wild-type NRC forms.

Figure 6B:
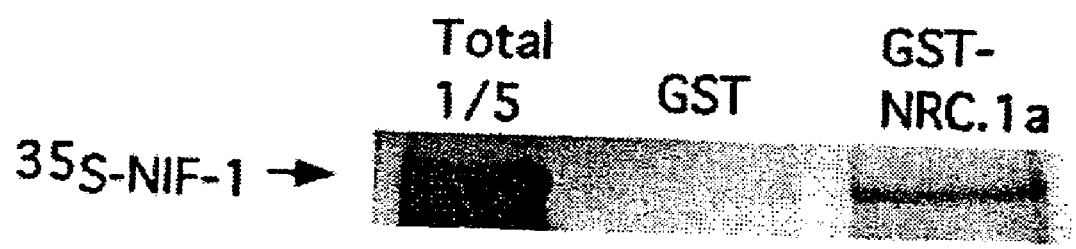

The yeast two-hybrid data suggested that residues 849-995 of human NRC and the corresponding region of rat NRC are involved in interaction with NIF-1. To document that this region of NRC binds to NIF-1 in vitro, this region of rat NRC was expressed as a GST-fusion in *E. coli*, and was purified with glutathione-agarose beads. $^{35}$S-labeled NIF-1, synthesized by in vitro transcription/translation in reticulocyte lysates, and incubated with (~200 ng) of purified GST or GST-NRC.1a at 4° C. for 30 min in binding buffer with mild shaking. The GST-glutathione-agarose beads were washed and the bound $^{35}$S-labeled proteins analyzed by SDS-gel electrophoresis followed by autoradiography. As shown in FIG. 6B, $^{35}$S-labeled NIF-1 bound to GST-NRC.1a but not to GST, indicating that NIF-1 binds to the same region of NRC in vitro as determined in FIG. 6A with the yeast two-hybrid assay.

Example 15

Figure 7:
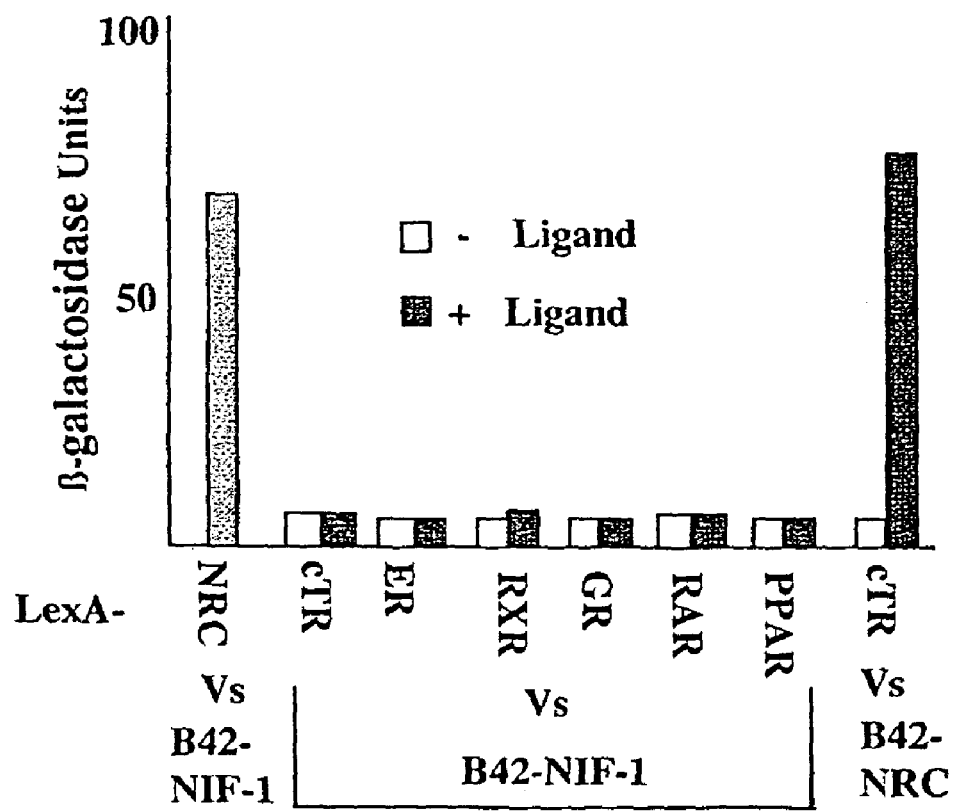
FIG. 7 is a graph showing that NIF-1 does not directly interact with nuclear receptor LBDs in yeast. NIF-1 was expressed as a B42-fusion and tested against LexA-fusions of the following receptor LBDs: cTRα, hERα, hRXRα, hGR, hRARα, hPPARα, and NRC. T3-dependent interaction of LexA-cTRα was also verified against B42-NRC in the same assay as a positive control.

NIF-1 Does Not Interact with Nuclear Hormone Receptors but Potentiates Ligand-Dependent Transcriptional Activity Since NIF-1 interacts with NRC, and NRC has been shown to be a potent co-regulator of ligand-bound nuclear hormone receptors, the next question to be determined was whether NIF-1 could modulate nuclear receptor activity. As shown in FIG. 1A, NIF-1 contains an LxxLL motif and, thus, might interact with nuclear hormone receptors directly even though it was cloned using NRC as bait. To examine for this possibility, the interaction of B42-NIF-1 (full-length), conditionally expressed from pJG4-5, was studied with LexA fusions of nuclear receptor LBDs (cTRα, ERa, RXRα, GR, RARα, and PPARα) in yeast, as shown in FIG. 7. In addition, a LexA-fusion of full-length cTRα was also tested against B42-NIF-1 (full-length) and gave similar results as with the cTRα LBD. NIF-1 did not interact with any of these receptors with or without cognate ligand, but strongly interacted with LexA-NRC. To document that the LexA-LBD fusions were expressed and responded to ligand in yeast, similar studies were carried out with B42-NRC. As expected, B42-NRC interacted with LexA-cTRα LBD in a T3 dependent manner, shown in FIG. 7. As previously described (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety), all other nuclear hormone receptors showed similar binding with B42-NRC in the presence of their cognate ligands.

Figure 8:
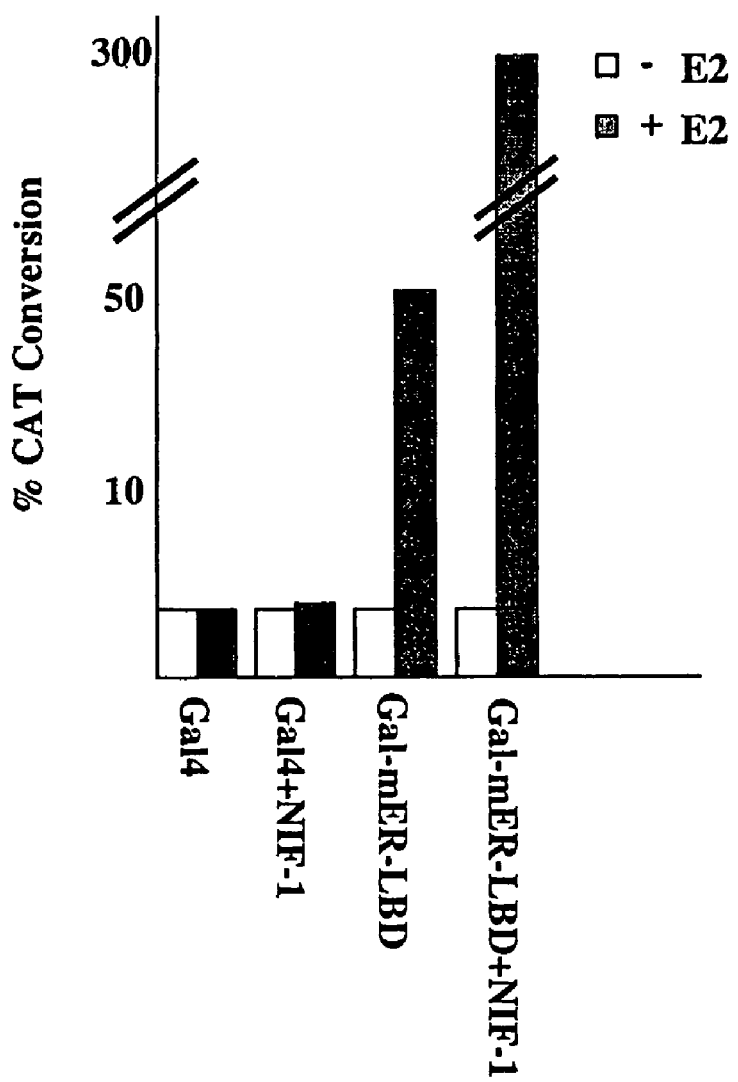
FIG. 8 is a graph showing that NIF-1 enhances ligand-dependent activation by Gal4-ER-LBD in HeLa cells. The Gal4 reporter, pBL-G5-CAT2, was co-transfected in HeLa cells with vectors expressing the Gal4-DBD or the Gal4-DBD fusion of the mER-LBD with or without NIF-1. Cells were incubated with or without ligand, E2 (100 nM), for 40 h and duplicate samples were then assayed for CAT activity. The experiment was repeated at least twice with similar results.

NIF-1 interacts with NRC but not with liganded nuclear receptors, indicating that the LxxLL motif found in NIF-1 is not a functional interaction domain for the nuclear hormone receptors tested in the present study. The possibility remains, however, that the LxxLL in NIFs may display selective interaction with other receptors/orphans not tested. Given the fact that NRC is a potent co-activator in mammalian cells for ligand-bound nuclear receptors, and that NIF-1 binds NRC in yeast and in vitro, it is likely that NIF-1 might affect the co-activator function of NRC in vivo. Transfection studies were therefore carried out to determine whether NIF-1 could enhance ligand-dependent receptor activity in mammalian cells. In the initial experiments, it was examined whether NIF-1 could alter the estradiol-mediated transcriptional activation of Gal4 fused to the mER-LBD (Gal4-mER-LBD) in HeLa cells, as shown in FIG. 8. Expression of NIF-1 did not alter transcriptional activity when expressed with the Gal4-DBD alone but enhanced the estradiol-mediated stimulation of Gal4-mER-LBD about 6-fold further indicating that receptor activity could be affected by NIF-1, albeit indirectly.

Figure 9A:
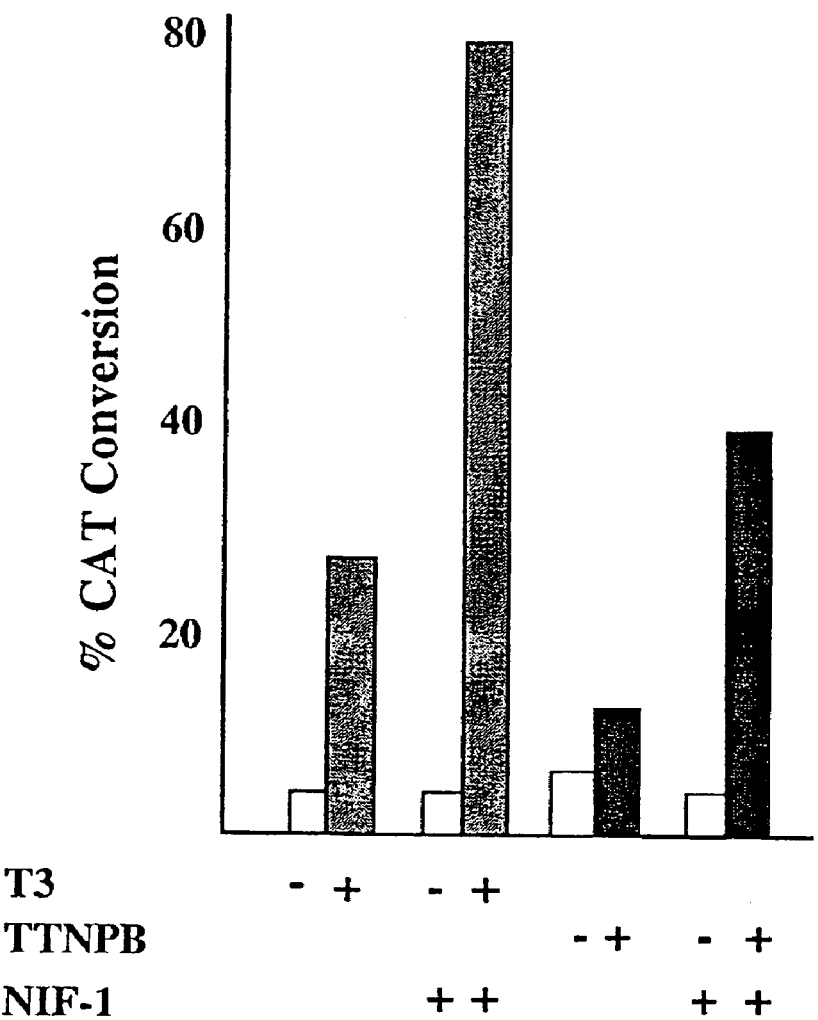
FIGS. 9A-B are the results of transfection experiments showing that NIF-1 activates TR, RAR and GR in HeLa cells.
Figure 9B:
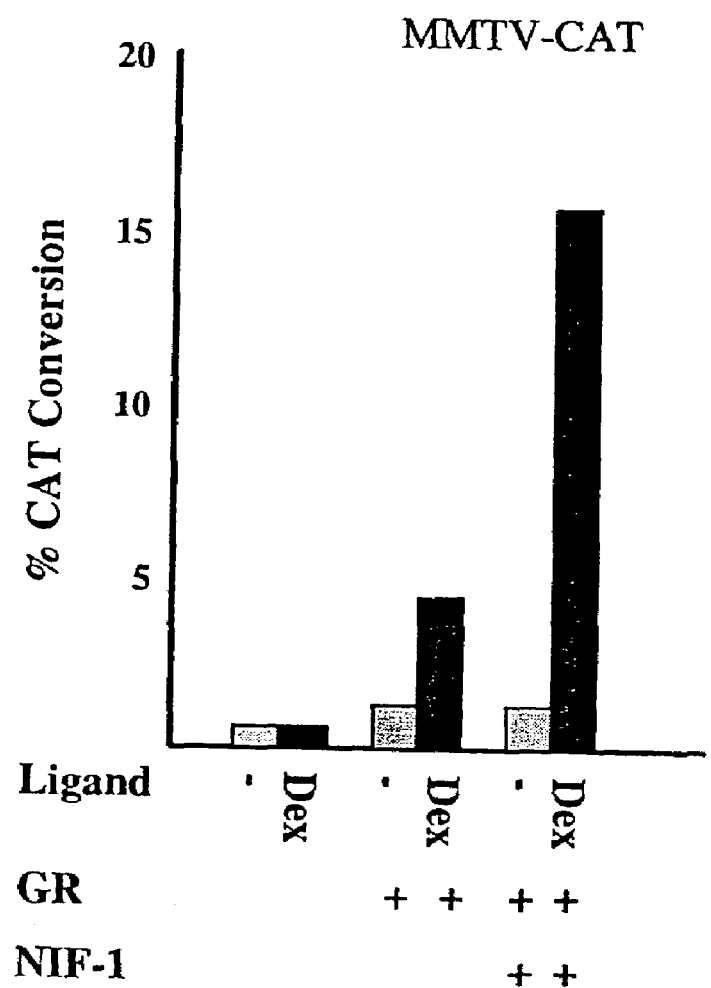

To study the effect of NIF-1 on the regulation of gene expression by wild-type receptors, the effect on NIF-1 on the ligand-dependent activity of TR, RAR, and GR were examined. Results are shown in FIGS. 9A-B. HeLa cells were transfected with appropriate CAT reporter genes, and with vectors expressing cTRα, hRARα, or hGR alone or with NIF-1. Ligand-dependent activation was studied using T3 for TR, the RAR-selective ligand TTNPB for RAR, as shown in FIG. 9A, and dexamethasone (Dex) for GR, shown in FIG. 9B. In each case, expression of NIF-1 enhanced the extent of ligand-dependent activation by these receptors about 3-fold.

Figure 10A:
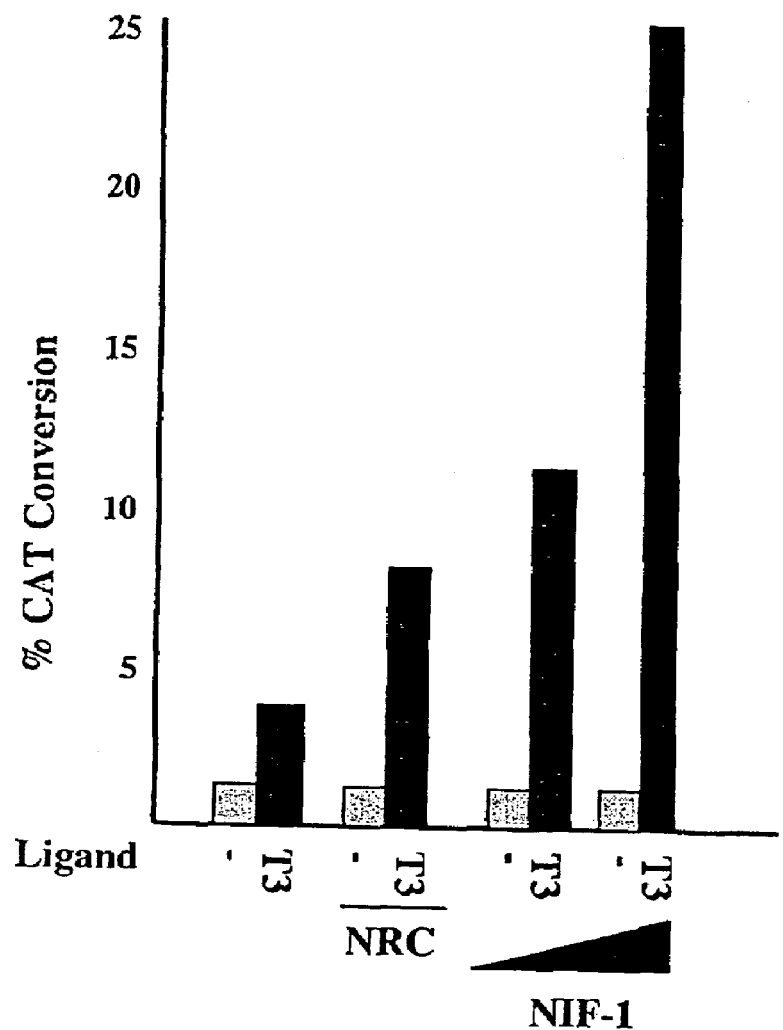
FIGS. 10A-B are the results of transfection experiments showing the ligand-dependent activation of endogenous nuclear receptors by NIF-1 in GH4C1 cells.
Figure 10B:
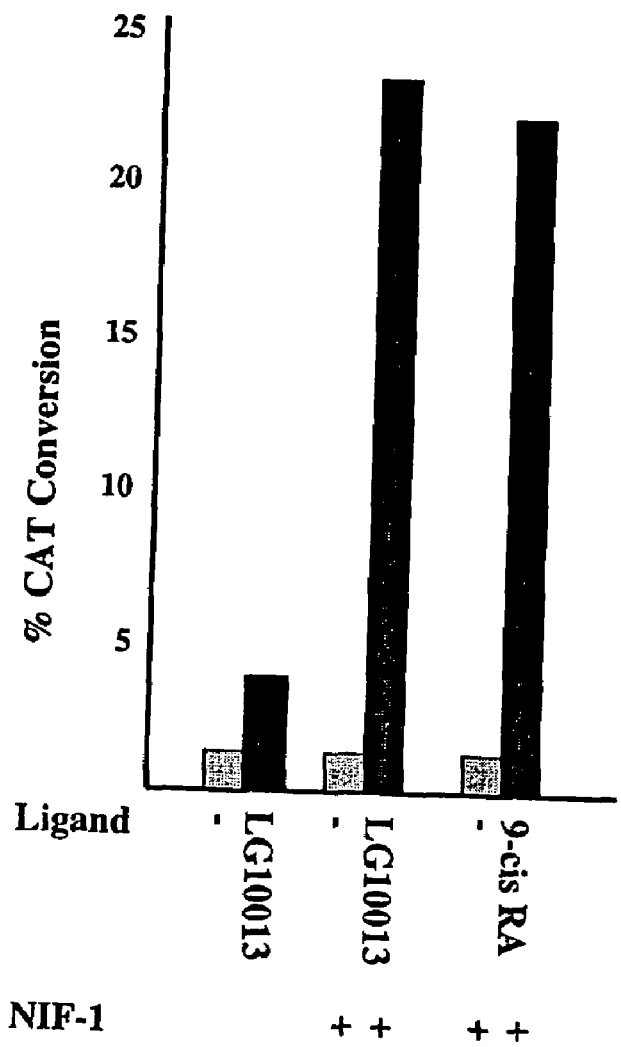

The effect of NIF-1 expression on transcriptional activation by endogenous TR and RXR was examined in GH4C1 cells. Results are shown in FIGS. 10A-B. NIF-1 enhanced T3-stimulation of endogenous TR activity about 6-fold and this effect of NIF-1 was greater than that found for NRC (about 2-fold), as shown in FIG. 10A, suggesting that NIF-1 may be more limiting for T3-stimulation in GH4C1 cells. NIF-1 also enhanced the activity of endogenous RXR about 6-fold, as assessed using LG10013 (an RXR-specific ligand) and 9-cis RA, shown in FIG. 10B.

Example 16

NIF-1 Potentiates Transcriptional Activity of AP1

Figure 11:
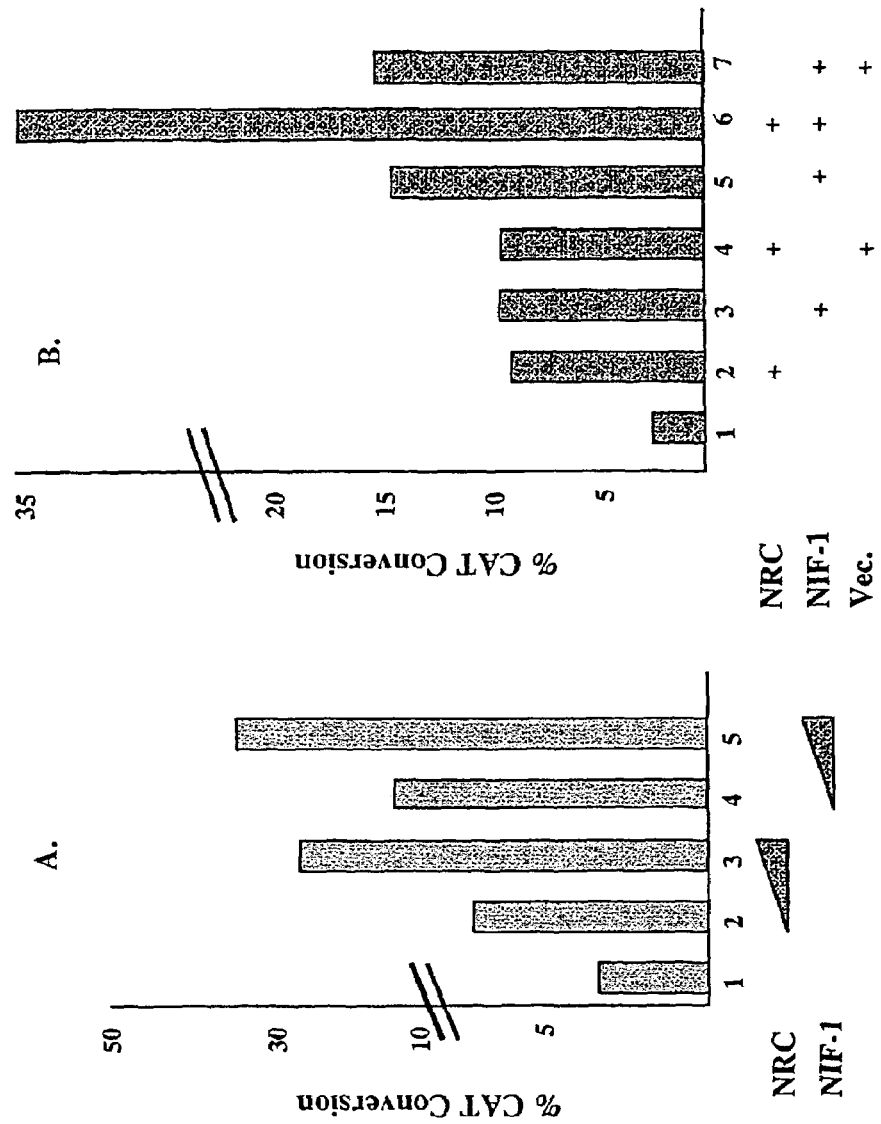
FIGS. 11A-B are the results of transfection experiments that show NIF-1 and NRC activate AP1 activity in HeLa cells.

Since NIF-1 interacts with NRC, and NRC has been shown to be a potent co-activator of cFos and cJun (AP1) (Ko et al., "Thyroid Hormone Receptor-Binding Protein, an LXXLL Motif-Containing Protein, Functions as a General Coactivator," *Proc. Natl. Acad. Sci. USA* 97:6212-6217 (2000), which is hereby incorporated by reference in its entirety), the effect of NIF-1 on the activity of endogenous AP1 in HeLa cells was examined. Results are shown in FIGS. 11A-B. HeLa cells were transfected with a CAT reporter for AP1 activity, −73 collagenase-CAT (Ways et al., "Dominant and Non-Dominant Negative c-erbAβ1 Receptors Associated with Thyroid Hormone Resistance Syndromes Augment TPA-Induction of the Collagenase Promoter and Exhibit Defective T3-Mediated Repression," *Mol. Endocrinol.* 7:1112-1120 (1993), which is hereby incorporated by reference in its entirety), with and without vectors expressing NRC and/or NIF-1. NRC increased the activity of the −73 collagenase-CAT reporter about 9-fold while NIF-1 enhanced the activity about 10-fold, shown in FIG. 11A. Expressing cFos and/or cJun in HeLa cells further enhanced the extent of activity of the −73 collagenase-CAT reporter and the expression of NRC or NIF-1 further increased the extent of activation. Since the activity of the −73 collagenase-CAT reporter gene was similarly affected by NRC or NIF-1, co-transfection studies were carried out using lower amounts of NRC or NIF-1 expression vectors to assess whether expression of both factors would lead to an effect greater than that found for each factor alone FIG. 11B. In this setting, expression of NRC resulted in a 3-fold stimulation while expression of NIF-1 led to a 5-fold increase in the activity of the −73 collagenase-CAT reporter gene. Expression of both NRC and NIF-1 resulted in a 12-fold increase further supporting the notion that NRC and NIF-1 functionally interact in the cell to enhance transcriptional activation.

Nuclear hormone receptors modulate a wide variety of developmental and physiological processes in vertebrates through the transcriptional regulation of target genes in specific tissues. A wide variety of studies indicate that the LBD of these receptors play a central role in mediating transcriptional activation as a result of ligand binding and this activity has been referred to as "activation function-2" or AF-2. In certain nuclear receptors, the variable N-terminal A/B domain also plays an important role in mediating transcriptional activation (e.g., GR, ER, PR) and this activity has been referred to as "activation function-1" or AF-1. Although AF-1 and AF-2 were defined functionally, an important question relates to defining the molecular determinants and protein-protein interactions that determine the activity of AF-1 and AF-2. Yeast two-hybrid screens and biochemical approaches have identified a number of factors which appear to function as co-activators or co-regulators of AF-2 and/or AF-1 function. Although certain nuclear receptor A/B domains appear to contain an independent activation function, the integration of the activity of the N-terminal A/B domain with the LBD in the context of full-length receptors results in a mutually dependent function of AF-1 and AF-2.

A central question is: how does co-activator binding to ligand bound receptor lead to transcriptional activation? The finding that p160 co-activators can associate with CBP/p300 suggests that transcriptional enhancement of nuclear receptors by co-activators involve the recruitment of large co-activator associated complexes to the promoter bound liganded receptor. In addition, co-activators may exist in dynamic association with different complexes, thereby leading to marked diversity in the extent of activation which may be dependent on cell type, the transcription factor, and possibly promoter context. Thus, different DRIP/TRAP complexes have been reported to contain both common and unique components, which are thought to be involved in the modulation of different transcription factors. For example, DRIP/TRAP, ARC, CRSP, SRB/mouse mediator and SMCC are related, but distinct, multiprotein complexes involved in activation of nuclear hormone receptors, SREBP-1a/Sp1, NF-kB (p65), Sp1, E1A/VP16, and p53 (Boyer et al., "Mammalian Srb/Mediator Complex is Targeted by Adenovirus E1A Protein," *Nature* 399:276-279 (1999); Ito et al., "Identity Between TRAP and SMCC Complexes Indicates Novel Pathways for the Function of Nuclear Receptors and Diverse Mammalian Activators," *Mol. Cell* 3:361-370 (1999); Naar et al., "Composite Co-Activator ARC Mediates Chromatin-Directed Transcriptional Activation," *Nature* 398:828-832 (1999); Rachez et al., "Ligand-Dependent Transcription Activation by Nuclear Receptors Requires the DRIP Complex," *Nature* 398:824-828 (1999), which are hereby incorporated by reference in their entirety). It is remarkable that most of the complexes share common polypeptides despite the fact that the transcription factors modulated by these protein complexes are structurally and functionally distinct. Interestingly, the NAT complex (Sun et al., "NAT, A Human Complex Containing Srb Polypeptides that Functions as a Negative Regulator of Activated Transcription," *Mol. Cell* 2:213-222 (1998), which is hereby incorporated by reference in its entirety), which represses activated transcription, shares components with other complexes involved in activation described above. Thus, it is becoming increasingly clear that these transcriptionally active complexes contain unique components but also share a number of common factors.

The cloning of a novel co-activator referred to as NRC which is part of a CBP complex in vivo that does not appear to include SRC-1 was recently described (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). In addition, TRBP (NRC) has also been reported to associate with DRIP130, a common component of some activator complexes including the DRIP/TRAP complex. Thus, as with other co-activators, NRC may exist as a component of distinct multiprotein complexes which may each mediate specific effects with a subset of transcriptional regulators.

Example 17

Characterization of NIF

In the present invention, the cloning and characterization of a novel factor from rat and human cells which interacts in vitro and in vivo with NRC and modulates the function of NRC in cells is described. Based on its ability to interact with NRC, this factor is referred to as NIF (NRC Interacting Factor).

Human NIF-1 is a 1342 amino acid nuclear protein containing six C2H2 zinc-finger domains, an N-terminal acidic sequence of ~35 residues rich in Glu and Asp, and an LxxLL motif and a putative leucine zipper-like motif in the C-terminal region. NIF-1 contains several putative PKA and tyrosine kinase phosphorylation sites. In addition, the first three C2H2 zinc-fingers appear to be part of the recently proposed BED finger DNA-binding domain (Aravind, "The BED Finger, A Novel DNA-Binding Domain in Chromatin-Boundary-Element-Binding Proteins and Transposases," *Trends Biochem. Sci.* 25:421-423 (2000), which is hereby incorporated by reference in its entirety). This domain is found in proteins thought to be involved in activation or repression through association with insulator sequences in the DNA (Hart et al., "Evidence for an Antagonistic Relationship Between the Boundary Element-Associated Factor BEAF and the Transcription Factor DREF," *Chromosoma* 108:375-383 (1999), which is hereby incorporated by reference in its entirety) and, thus, may act to modulate local chromatin structure. Human NIF-1 and the partial rat NIF clone identified in the yeast two-hybrid screen share 86% homology at the amino acid level. In particular, the zinc-finger domains, LxxLL region, and the leucine zipper-like motif are highly conserved. A GenBank search identified a NIF-related partial chicken cDNA clone (cFZF) of unknown function. cFZF shares 62% homology with the corresponding region of human NIF-1 with divergence of zinc-finger 5 and the leucine zipper-like regions. An LxxLL region is highly conserved in all three proteins. Although this LxxLL motif does not mediate interaction with NRC or the ligand-bound nuclear hormone receptors that were examined, its conservation implies that it may subserve an important function in mediating other protein-protein interactions.

An EST database search identified a number of human NIF ESTs. DNA sequencing indicated that one of the ESTs (BE297231) (~2.2 kb) contained the identical 5' and 3' coding sequences as found in NIF-1. This cDNA appears to reflect an alternatively spliced form of NIF-1 which is referred to herein as NIF-2. NIF-2 lacks 559 amino acids residues (185 to 743 of SEQ ID NO: 3) containing zinc-fingers 1 to 4. However, NIF-2 retains the NRC interaction region which includes zinc-finger 6. In keeping with this, NIF-2 interacts with NRC in yeast two hybrid assays. However, the role of NIF-2 with respect to NRC and its other functions remain to be elucidated. A multi-tissue Northern blot probed with full-length $^{32}$P-NIF-1 cDNA identified a widely expressed low abundant ~5 kb transcript and a less abundant ~2.5 kb transcript which appears to be more restricted in its tissue expression. It can be assumed that the ~5 kb transcript is NIF-1 and the ~2.5 kb transcript is NIF-2.

Full-length human NIF-1 binds NRC in vivo and in vitro, and extensive mapping using yeast two-hybrid assays indicate that the NRC-interacting domain of NIF-1 occurs through a region containing zinc-finger 6. Interestingly, a short region of 97 amino acids containing zinc-finger 6, which is conserved in the rat and human NIFs and in chicken c-FZF, appears to be sufficient for a strong interaction with NRC in yeast. A very weak interacting region containing zinc-finger 1 was also detected. Zinc-finger 1 shares a weak similarity with zinc-finger 6. An NIF-interaction domain in NRC was mapped by using various regions of NRC in yeast two-hybrid assays. The domain was mapped to a 146 amino acids region of NRC (amino acids 849-995) which also contains the LxxLL receptor interacting domain of NRC. However, this LxxLL motif of NRC is not directly involved in the interaction of NRC with NIF-1 since mutation of the LxxLL motif LVNLL (SEQ ID NO: 9) to AVNAA (SEQ ID NO: 10), which eliminates NRC-receptor interactions, did not alter the interaction of NRC with NIF-1. This suggests that NIF-1 and activated receptors could simultaneously interact with NRC. This finding is consistent with the observation that NIF-1 can enhance ligand-dependent transcriptional activation without directly interacting with nuclear hormone receptors.

It was previously reported that NRC can enhance the activity of a wide number of nuclear hormone receptors (Mahajan et al., "A New Family of Nuclear Receptor Coregulators That Integrate Nuclear Receptor Signaling Through CREB-Binding Protein," *Mol. Cell. Biol.* 20:5048-5063 (2000), which is hereby incorporated by reference in its entirety). The present invention now teaches that NIF-1, which does not interact with receptors, also enhances the activity of expressed ER, TR, GR, and RAR in HeLa cells, and endogenous TR and RXR in GH4C1 cells which contain NRC. In addition, the activity of cFos and cJun, which have been reported to be enhanced by NRC, are also enhanced by NIF-1. It is presumed that this modulation of ligand-bound nuclear hormone receptors by NIF-1 occurs through its interaction with NRC and not through the interaction of other factors. However, it is possible that NIF-1 could also be a component of other co-activator complexes not involving NRC. To further define whether NRC is required for the effect of NIF-1 on nuclear receptors or cFos or cJun will require cells which do not express NRC.

Recently, in addition to NIF-1, three other factors, CAPER, PIMT, and CoAA (Iwasaki et al., "Identification and Characterization of RRM-Containing Coactivator Activator (CoAA) as TRBP-Interacting Protein, and its Splice Variant as a Coactivator Modulator (CoAM)," *J. Biol. Chem.* 276:33375-33383 (2001); Jung et al., "Molecular Coning and Characterization of CAPER, A Novel Coactivator of Activating Protein-1 and Estrogen Receptors," *J. Biol. Chem.* 277:1229-1234 (2002); Zhu et al., "Cloning and Characterization of PIMT, A Protein With a Methyltransferase Domain, Which Interacts With and Enhances Nuclear Receptor Coactivator PRIP Function," *Proc. Natl. Acad. Sci. USA* 98:10380-10385 (2001), which are hereby incorporated by reference in their entirety), were reported to interact with NRC proteins (ASC-2/PRIP/TRBP). CAPER, PRIP, and CoAA are distinct proteins which each contain RNA binding motifs. In contrast, NIF-1 does not contain RNA binding motifs. CAPER was reported to interact directly with ERox and ERP but not TR, GR, RXR or PPAR and to enhance activation by ER about 3-fold. PIMT appears to contain a methyltransferase activity. However, enhancement of stimulation by RXR or PPAR (~1.6-fold) did not require methyltransferase activity. Expression of CoAA enhanced the activity of GR, TR, and ER about 3-fold. Whether these changes reflects a direct or indirect interaction of PIMT or CoAA with nuclear receptors was not examined. Since CAPER, PIMT, and CoAA were each cloned as an interactor with NRC, further studies are needed to determine whether these factors including NIF-1 are also integral components of other co-activator complexes in the cell.

Since NIF-1 does not directly associate with receptors but enhances their activities, it functions differently from previously described co-activators which exert their effects through direct association with ligand-bound receptors. Thus, it is suggested that NIF-1, and factors which behave similar to NIF-1, be referred to as co-transducers which act in vivo either as part of a co-activator complex or downstream of a co-activator complex to modulate transcriptional activity. Examples of such factors include CARM1 and PRMT1 (Chen et al., "Regulation of Transcription by a Protein Methyltransferase," *Science* 284:2174-2177 (1999); Koh et al., "Synergistic Enhancement of Nuclear Receptor Function by p160 Coactivators and Two Coactivators with Protein Methyltransferase Activities," *J. Biol. Chem.* 276: 1089-1098 (2001); Wang et al., "Methylation of Histone H4 at Arginine 3 Facilitating Transcriptional Activation by Nuclear Hormone Receptor," *Science* 293:853-857 (2001), which are hereby incorporated by reference in their entirety). How would a co-transducer such as NIF-1 enhance the activity of co-activators such as NRC? The mechanism(s) have not yet been defined but include: 1) contribution of an activation surface, 2) conformational alteration of a co-activator to expose an activation domain, 3) interaction with other proteins to stabilize a multiprotein co-activator complex, 4) direct association with the basal transcription machinery, or 5) through modification of chromatin architecture as a BED domain protein. Since the C2H2 class of zinc-finger has been reported to be involved in DNA interactions, this raises the possibility that NIF-1 may directly bind DNA. Thus, in addition to being a component of a co-activator complex recruited to a transcription factor (e.g. nuclear receptors, cFos, cjun) by a co-activator (e.g. NRC), NIF-1 might also act as a DNA binding factor that modulates transcription by recruiting a co-activator complex to a specific target gene. Thus, NIF-1 may mediated its effects by acting through multiple mechanisms in the cell.

Recent studies by the inventors indicate that NIF-1 interacts with TRAP80, a component of Mediator complex, the major multiprotein transcriptional coactivator complex in *Drosophila melanogaster*. Mediator components interact with diverse sets of transcriptional activator proteins to elicit sophisticated regulation of gene expression (Park et al., "Signal-Induced Transcriptional Activation by Dif Requires the dTRAP80 Mediator Module," *Mol. Cell. Biol.* 23(4): 1358-1367 (2003). The interaction between NIF-1 and TRAP80 may have important consequences on cell growth through the tumor suppressor, p53. In addition, it appears that NIF-1 is anti-apoptotic, i.e., is involved in preventing programmed cell death. These discoveries further implicate NIF-1 as an important, perhaps requisite, factor in cell growth and proliferation. Therefore, NIF-1 overexpression may be a factor in the etiology of some disease conditions, for example, cancer.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated nucleic acid molecule selected from the group consisting of: 1) a nucleic acid molecule comprising the nucleotide sequence of SEQ ID NO: 1; 2) a nucleic acid molecule comprising the nucleotide sequence of SEQ ID NO: 4; and 3) a nucleic acid molecule encoding a protein comprising the amino acid sequence of SEQ ID NO: 3.

2. A nucleic acid construct comprising:
   the nucleic acid molecule according to claim 1;
   a 5' regulatory region operably linked to the nucleic acid molecule; and
   a 3' regulatory region operably linked to the nucleic acid molecule.

3. An expression vector comprising:
   the nucleic acid construct according to claim 2.

4. An isolated host cell transformed with the nucleic acid molecule according to claim 1.

5. The isolated host cell according to claim 4, wherein the host cell is selected from the group consisting of a bacterial cell, a yeast cell, and a mammalian cell.

6. The isolated host cell according to claim 5, wherein the host cell is a mammalian cell.

* * * * *